(12) United States Patent
Haymore

(10) Patent No.: US 8,361,779 B2
(45) Date of Patent: Jan. 29, 2013

(54) BUFFER COMPOUNDS

(75) Inventor: Barry L. Haymore, Austin, TX (US)

(73) Assignee: Sachem, Inc., Austin, TX (US)

( * ) Notice: Subject to any disclaimer, the term of this patent is extended or adjusted under 35 U.S.C. 154(b) by 287 days.

(21) Appl. No.: 12/953,569

(22) Filed: Nov. 24, 2010

(65) Prior Publication Data

US 2012/0129240 A1    May 24, 2012

(51) Int. Cl.
  *C12N 1/20*    (2006.01)
  *C12N 1/00*    (2006.01)
  *C07D 243/08*    (2006.01)

(52) U.S. Cl. ............ 435/255.7; 435/253.6; 540/575

(58) Field of Classification Search ........... 435/253.6, 435/255.3; 540/575
See application file for complete search history.

(56) References Cited

FOREIGN PATENT DOCUMENTS
EP    494686    7/1992

OTHER PUBLICATIONS

Liu Qian et al: "Separation of acidic and basic proteins by capillary electrophoresis using gemini surfactants and gemini-capped nanoparticles as buffer additives", SCI CHINA SER B-CHEM. vol. 52, No. 10. Oct. 2009, pp. 1666-1676.
PCT/US2011/051296; PCT International Search Report and Written Opinion of the International Searching Authority dated Jun. 21, 2012.

*Primary Examiner* — Herbert J Lilling
(74) *Attorney, Agent, or Firm* — Renner, Otto, Boisselle & Sklar, LLP

(57) ABSTRACT

A method of buffering a chemical or biological composition, comprising adding to the composition an effective buffering amount of at least one protonated or un-protonated amine-quaternary ammonium compound having a general formula:

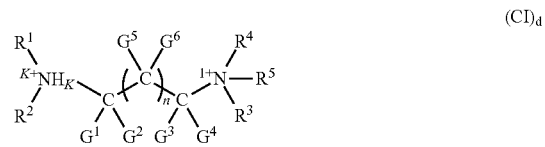

wherein the variables R, G, n and k are as defined herein.

11 Claims, 4 Drawing Sheets

BUFFER COMPOUNDS

TECHNICAL FIELD

The present invention relates to buffer compounds, especially buffer compounds for use in biological systems, in which the buffer compound comprises amine-quaternary ammonium compounds. More particularly, the invention relates to buffer compounds in which the buffer molecule contains both an amine nitrogen atom and a quaternary ammonium nitrogen atom.

BACKGROUND

Classical buffer compounds are chemical compounds or agents that resist or minimize changes in hydrogen-ion concentrations when a system of interest is placed under chemical stress or physical stress. Chemical stress includes generation or consumption of hydrogen ions, change in ionic strength and change in solvent properties. Physical stress includes changes in temperature and/or pressure. In many circumstances it is useful or necessary to keep the pH constant or within a narrow range. Buffer compounds are often used in homogeneous aqueous solution, but they may also be used in solid or semisolid mixtures, in non-aqueous polar solvents or in creams, ointments or suspensions. Natural buffer compounds are used in biological systems or living cells to maintain or modulate the proper pH conditions. Natural and synthetic buffer compounds are used commercially in water treatment and sanitation, in agents to control corrosion, in fertilizer mixtures for agriculture, in medicinal formulations and personal care products, in foods and beverages, in fermentation and brewing, in paints and coatings, in human or animal drugs and in many other applications.

pH is a measurement of solvated hydrogen-ion activity, which is directly related to hydrogen ion concentration: $-\log [H^+]$. The strength of a monoprotic neutral acid (HA) or monoprotic conjugate acid of a neutral base ($HB^+$) are measured by the $pK_a$ values for the respective reactions which are defined by:

$$HA + H_2O \rightleftharpoons OH_3^+ + A^- \quad HB^+ + H_2O \rightleftharpoons OH_3^+ + B$$

$$pK_a = -\log K_a \text{ where } K_a = [OH_3^+][A^-]/[HA] \text{ or } K_a = [OH_3^+][B]/[HB^+]$$

Rearranged, these equations give:

$$pH = pK_a + \log([A^-]/[HA]) \text{ or } pH = pK_a + \log([B]/[HB^+])$$

Each bracketed item in the above equations reflects the "activity" of the respective neutral and ionic species in solution. Activity is a defined thermodynamic term and is related to concentration. At low concentration and low ionic-strength, activity approximately equals concentration. Herein, we use concentration-based $pK_a$ values measured at 25° C. at ionic-strength ($\mu$) of 0.10, unless otherwise specified. Such $pK_a$ values are more applicable to practical conditions than are thermodynamic $pK_a$ values where $\mu \approx 0$.

The pH range and scale has particular meaning only in a specified solvent of interest and is referenced to certain defined pH standards. The solvation properties of the solvent toward the conjugate acids and bases dictate the degree of ionization and the strength of the acids and bases. Furthermore, most polar solvents have self-ionization properties that limit the strength of strong acids and strong bases dissolved in that solvent. This effect, called the "leveling effect", is readily apparent in water where the self-ionization constant, $pK_w$, is about 13.8 (25° C., $\mu$=0.1). Under these conditions, neutrality, that is when $[OH_3^+] = [OH^-]$, is defined by $pH = 0.5 \cdot pK_w = 6.9$.

When water is the solvent, the acidity ($pK_a$) of solvated $OH_3^+$ is about −1.7 while that of solvated $OH_2$ is about +15.5. Dissolved in water, bases stronger than hydroxide simply react with the water forming $OH^-$ (hydroxide ion). Similarly, acids stronger than $OH_3^+$ react with water forming $OH_3^+$. Hence, under practical conditions when the acid/base concentration is about 0.10 M and the solvent concentration ($H_2O$) is about 55.5 M, the leveling effect of water limits the useful pH range for buffering to about 1.0-12.8. Furthermore, other practical limitations in water make working with buffers inconvenient or difficult when operating outside the range 2-12.

An important property of a buffer compound is its buffering capacity, that is, how much $OH_3^+$ or $OH^-$ can be neutralized by the buffer while minimizing the pH change in solution. The equations above show that the buffering capacity is directly related to (a) the concentration of the buffer and (b) the difference ($\Delta$) between the operating pH and the $pK_a$ of the buffer. More buffering capacity can be obtained by (a) increasing the concentration of the buffer compound, (b) by finding a suitable buffer compound so that $\Delta$ is smaller or (c) by adjusting the operating pH so that $\Delta$ is smaller. A user of buffer compounds must estimate how much acid or base may be generated in the system under study and how much pH variation can be tolerated in order to choose proper buffers and concentrations. Except near the extreme ends of useful pH ranges (pH=2 or 12), the following table allows one to estimate the actual buffering capacity (mM) as a fraction of total buffer compound concentration ($C_B$, mM) at different $\Delta$ values. Useful buffering range of a buffer compound is the pH interval within which at least 50% of the maximum buffering capacity is to be maintained. As seen below, the buffering range of a typical monoprotic acid is about 0.96 pH units, that is ±0.48 pH units centered at the $pK_a$ value.

| Capacity (mM) | $\Delta$ (pH-$pK_a$) |
| --- | --- |
| $0.500 \cdot C_B$ | 0.00 |
| $0.443 \cdot C_B$ | ±0.10 |
| $0.400 \cdot C_B$ | ±0.18 |
| $0.387 \cdot C_B$ | ±0.20 |
| $0.333 \cdot C_B$ | ±0.30 |
| $0.285 \cdot C_B$ | ±0.40 |
| $0.250 \cdot C_B$ | ±0.48 |
| $0.240 \cdot C_B$ | ±0.50 |
| $0.201 \cdot C_B$ | ±0.60 |
| $0.167 \cdot C_B$ | ±0.70 |
| $0.137 \cdot C_B$ | ±0.80 |
| $0.112 \cdot C_B$ | ±0.90 |
| $0.091 \cdot C_B$ | ±1.00 |

Many buffer compounds have been developed for a multitude of uses, including in biological systems. Buffers for use in biological systems face a number of requirements, including low toxicity to living biologic organisms, low metal-binding properties, low sensitivity to pH changes caused by changes in temperature, and specific ionic-charge. Many previously known buffer compounds used in biological systems have suffered from a lack of one or more of these characteristics, and thus there has been an on-going, long-felt need for improved buffer compounds with special, predetermined and controllable properties.

In addition, known buffer compounds, particularly those for use in biological systems, have suffered from an inability to facilely cover the entire pH range. Certain portions of the pH range, for example the range from pH 11 to pH 13, have been notoriously bereft of buffers able to maintain pH within this range.

In addition, because buffer compounds prepared for use in various pH ranges were often chemically quite different, there have been compatibility problems arising from the chemical differences that were inherent in the different buffer compounds needed to obtain buffering at different pH ranges. Ideally, a buffer should control pH only and interact minimally with the constituent molecules under study or of interest in the solution. One important property is its overall charge. If the chemical substances of interest are charged, then a buffer compound of the same charge is used to minimize interaction in solution or mixture. These chemical differences introduce another variable that must be considered when selecting an appropriate buffer compound for a particular application. For these additional reasons, there has been an on-going, long-felt need for improved buffer compounds with special, predetermined and controllable properties.

SUMMARY

The present invention addresses the long-felt need for buffer compounds capable of buffering and maintaining pH across substantially the full range of pH from pH 2 to pH 13, while at the same time providing desirable properties, including one or more of selectable, predetermined charge properties, low toxicity to living biologic organisms, low metal-binding properties, and low sensitivity to pH changes caused by changes in temperature, and having sufficient chemical compatibility between substances of interest and the buffering compounds that provide buffering over a wide range of pH thus avoiding many of the problems resulting from chemical differences accompanying different buffer compounds used to obtain buffering over a wide range of pH. For biological systems, the most important pH range is from pH 4 to pH 10, and the present invention provides great versatility in selection of appropriate buffer compounds for use in this range.

The present inventors have developed a quite novel and non-obvious series of buffer compounds that are based on an amine-quaternary ammonium ("amine-quat") structure. The various substitutions on the amine and the proximity of the quaternary ammonium group to the amine allow a family of buffer molecules to be constructed that have a wide range of useful $pK_a$ values (2-13), while at the same time useful and unique chemical and physical properties (e.g., charge, solubility) can be imparted in a controllable, predetermined manner to the buffer compounds, thus enhancing their function and utility. These new buffer compounds can be used for general-purpose applications, specialty applications and/or biological applications.

The amine-quat compounds are composed of five structural types with different properties.

1. Monoamine-monoquat. These monoprotic buffer compounds are cationic under all protonation conditions.
2. Monoamine-monoquat with a single attached anionic group ($1^-$ or $2^-$) whose $pK_a$ value(s) is(are) outside the buffering range of interest. These nominally monoprotic buffer compounds have charged species in the range $2^+$ to $1^-$.
3. Monoamine-monoquat with two attached anionic groups ($1^-$ or $2^-$) whose $pK_a$ values are outside the buffering range of interest. These nominally monoprotic buffer compounds have charged species in the range $2^+$ to $3^-$.
4. Monoamine-monoquat with 1-2 attached anionic groups ($1^-$ or $2^-$) wherein at least one $pK_a$ value of an anionic group is within the buffering range of interest. These nominally diprotic or polyprotic buffer compounds have two or more overlapping $pK_a$ values that are typically spaced about 1 to about 2 log $K_a$ units apart. These wide-range buffer compounds have charged species in the range $2^+$ to $3^-$.
5. Diamine-monoquat with 0-3 attached anionic groups ($1^-$ or $2^-$). These nominally diprotic or polyprotic buffer compounds have two or more overlapping $pK_a$ values (amines and/or anions) that are typically spaced about 1 to about 2 log $K_a$ units apart. These wide-range buffer compounds have charged species in the range $3+$ to $5-$.

The foregoing amine-quat buffer compounds may be synthesized from symmetric and unsymmetric diamines and amine-guanidines where one of the amine or guanidine nitrogen atoms is quaternized leaving a positively charged mono-amine or mono-guanidine. These amine-quat buffer compounds, in their acidic and basic forms, are colorless, non-volatile, organic salts and/or zwitterions with appreciable solubility in water and in many organic solvents and solvent mixtures. The amine-quat buffer compounds are conveniently prepared in reasonable yield using one to three synthetic steps from readily available chemical starting materials. After synthesis, pure materials (>99%) are obtained after 1-3 cycles of recrystallization from common solvents.

Thus, in one embodiment, the present invention relates to a protonated or un-protonated amine-quaternary ammonium buffer compound, and to a method of buffer compounding a chemical or biological composition, comprising adding to the composition an effective buffer compounding amount of at least one protonated or un-protonated amine-quaternary ammonium buffer compound, in which the amine-quaternary ammonium buffer compound has a general formula:

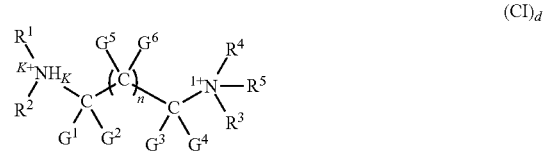

wherein:

n has integer values in the range 0-4, k is 0 for the un-protonated compound and k is 1 for the protonated compound;

each $G^1$, $G^3$ and $G^5$ is a chemical moiety independently selected from —H, —$CH_3$, —$C_2H_5$, or is a component of a cyclic chemical moiety, each $G^2$ and $G^4$ is a chemical moiety independently selected from —H, —$CH_3$, —$CH_2OH$, —$C_2H_5$, —$CO_2H$, —$SO_3H$, —$PO_3H_2$, —$CO_2^-$, —$SO_3^-$, —$PO_3H^-$ and —$PO_3^{2-}$, or is a component of the cyclic chemical moiety, each $G^6$ is a chemical moiety independently selected from —H, —$CH_3$, —$CH_2OH$, —$C_2H_5$, —OH, —$OCH_3$, —$CO_2H$, —$SO_3H$, —$PO_3H_2$, —$CO_2$, —$SO_3$, —$PO_3H^-$ and —$PO_3^2$, or is a component of the cyclic chemical moiety and each $R^1$, $R^2$, $R^3$, $R^4$ and $R^5$ is a chemical moiety independently selected from —$CH_3$, —$C_2H_5$, —$CH(CH_3)_2$, -cyclohexyl, —$C_2H_4OH$, —$C_2H_4OCH_3$, —$(CH_2)_{2-3}NHC(O)CH_3$, —$(CH_2)_{2-3}N(CH_3)C(O)CH_3$, —$(CH_2)_{1-3}C(O)NH_2$, —$(CH_2)_{1-3}C(O)NHCH_3$, —$(CH_2)_{1-3}C(O)N(CH_3)_2$, —$CH_2(CG^5G^6)_mSO_3^-$, —$CH_2(CG^5G^6)_mCO_2^-$, —$CH_2(CG^5G^6)_mCO_2H$, —$CH_2(CG^5G^6)_mPO_3^{2-}$, —$CH_2(CG^5G^6)_mPO_3H^-$, —$CH_2(CG^5G^6)_mPO_3H_2$ with m being 0, 1, 2 or 3, or is a component of the cyclic chemical moiety, or $R^5$ is a chemical moiety —$[CG^7G^8-(CG^7G^9)_r-CG^7G^8-H_jNR^6R^7]^{j+}$, wherein each $G^7$ is a chemical moiety independently selected from —H, —$CH_3$, —$C_2H_5$, each $G^8$ is a chemical moiety independently selected from —H, —CH$_3$, —CH$_2$OH, —C$_2$H$_5$, —CO$_2$H, —SO$_3$H, —PO$_3$H$_2$, —CO$_2^-$, —SO$_3^-$, —PO$_3$H$^-$, and —PO$_3^{2-}$, G$^9$ is a chemical moiety independently selected from —H, —CH$_3$, —CH$_2$OH, —C$_2$H$_5$, —OH, —OCH$_3$, —CO$_2$H, —SO$_3$H, —PO$_3$H$_2$, —CO$_2^-$, —SO$_3^-$, —PO$_3$H$^-$, and —PO$_3^{2-}$, r has integer values in the range 0-4, and j is 0 or 1, and each R$^6$ and R$^7$ is a chemical moiety independently selected from —CH$_3$, —C$_2$H$_5$, —CH(CH$_3$)$_2$, -cyclohexyl, —C$_2$H$_4$OH, —C$_2$H$_4$OCH$_3$, —(CH$_2$)$_{2-3}$NHC(O)CH$_3$, —(CH$_2$)$_{2-3}$N(CH$_3$)C(O)CH$_3$, —(CH$_2$)$_{1-3}$C(O)NH$_2$, —(CH$_2$)$_{1-3}$C(O)NHCH$_3$, —(CH$_2$)$_{1-3}$C(O)N(CH$_3$)$_2$, —CH$_2$(CG$^5$G$^6$)$_m$SO$_3^-$, —CH$_2$(CG$^5$G$^6$)$_m$CO$_2^-$, —CH$_2$(CG$^5$G$^6$)$_m$CO$_2$H, —CH$_2$(CG$^5$G$^6$)$_m$PO$_3^{2-}$, —CH$_2$(CG$^5$G$^6$)$_m$PO$_3$H$^-$, —CH$_2$(CG$^5$G$^6$)$_m$PO$_3$H$_2$ with m being 0, 1, 2 or 3;

wherein when the compound comprises the cyclic chemical moiety, the cyclic chemical moiety is one or more selected from (a), (b), (c), (d), (e), (f) and (g):

(a) one or more pair of R$^1$ and R$^2$, R$^3$ and R$^4$, R$^3$ and R$^5$, and/or R$^4$ and R$^5$, forms a single chemical moiety such that the pair is individually and independently —CH$_2$CH$_2$CH$_2$CH$_2$—, —CH$_2$CH(OH)CH(OH)CH$_2$—, —CH$_2$CH$_2$CH$_2$CH$_2$CH$_2$—, —CH$_2$CH$_2$OCH$_2$CH$_2$—, —CH$_2$CH$_2$CH(OH)CH$_2$CH$_2$—, —CH$_2$CH$_2$N(C(O)G$^1$)CH$_2$CH$_2$—, —CH$_2$C(O)N(G$^1$)CH$_2$CH$_2$—, —CH$_2$CH(OH)CH(OH)CH$_2$—, =C(NG$^1_2$)$_2$,

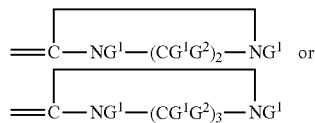

(b) one or more pair of R$^1$ and R$^3$, R$^1$ and R$^4$, R$^1$ and R$^5$, R$^2$ and R$^3$, R$^2$ and R$^4$ and/or R$^2$ and R$^5$ forms a single chemical moiety such that the pair is individually and independently —(CG$^1$G$^2$)$_g$- with n being 0 or 1 and g being 2 or 3;

(c) one or more pair of G$^1$ and G$^3$, G$^2$ and G$^4$, G$^1$ and G$^4$ and/or G$^2$ and G$^3$ forms a single chemical moiety such that the pair is individually and independently —(CG$^1$G$^6$)$_q$- with q having integer values 0-4 and the sum of q and n having integer values 3-4, and, when q=0, —(CG$^1$G$^6$)$_0$- is a single carbon-carbon bond between the carbon atoms to which the pair is attached in the general formula;

(d) one or more pair of G$^1$ and G$^2$, G$^3$ and G$^4$, and/or G$^5$ and G$^6$ forms a single chemical moiety such that the pair is individually and independently —(CG$^1$G$^6$)$_w$- with w having integer values 4-5;

(e) one or more pair of R$^1$ and G$^3$, R$^1$ and G$^4$, R$^2$ and G$^3$, R$^2$ and G$^4$, R$^3$ and G$^1$, R$^3$ and G$^2$, R$^4$ and G$^1$, R$^4$ and G$^2$, R$^5$ and G$^1$, and/or R$^5$ and G$^2$ forms a single chemical moiety such that the pair is individually and independently —(CG$^1$G$^2$)$_s$- with s having integer values 1-3, n having integer values 0-2 and the sum of s and n having integer values 2-3;

(f) one or more pair of R$^1$ and G$^5$, R$^1$ and G$^6$, R$^2$ and G$^5$, R$^2$ and G$^6$, R$^3$ and G$^5$, R$^3$ and G$^6$, R$^4$ and G$^5$, R$^4$ and G$^6$, R$^5$ and G$^5$, and/or R$^5$ and G$^6$ forms a single chemical moiety such that the pair is individually and independently —(CG$^1$G$^2$)$_v$- with v having integer values 0-3, n having integer values 1-4 and the sum of v and n having integer values 3-4 and, when v=0, —(CG$^1$G$^2$)$_0$- is a single carbon-carbon bond between the carbon atoms to which the pair is attached in the general formula; and (g) one or more pair of R$^1$ and G$^1$, R$^1$ and G$^2$, R$^2$ and G$^1$, R$^2$ and G$^2$, R$^3$ and G$^3$, R$^3$ and G$^4$, R$^4$ and G$^3$, R$^4$ and G$^4$, R$^5$ and G$^3$, and/or R$^5$ and G$^4$ forms a single chemical moiety such that the pair is individually and independently —(CG$^1$G$^2$)$_u$- with u having integer values 3-4;

wherein CI is a non-interfering counter-ion or mixture of non-interfering counter-ions as needed to maintain electroneutrality, with the charge on the amine-quaternary ammonium compound being equal to the value of quantity (j+k−z+1) wherein z equals the absolute value of the numerical sum of all negative charges on each —CO$_2^-$, —SO$_3^-$, —PO$_S$H$^-$, and —PO$_3^{2-}$ moiety contained within R$^1$, R$^2$, R$^3$, R$^4$, R$^5$, R$^6$, R$^7$, G$^2$, G$^4$, G$^6$ G$^8$ and/or G$^9$ present and wherein d equals |j+k−z−k1| for monovalent counter-ions, |j+k−z+1|/2 for divalent counter-ions, j+k−z+1|/3 for trivalent counter-ions, |j+k−z+1|/4 for tetravalent counter-ions and the sign of (z−j−k+1) reflects the charge on the counter-ion(s), except that when (j+k−z+1) is zero, d is zero and no separate counter-ion is present.

It is noted that, if there is no second amine nitrogen (i.e., when R$^5$ is not a chemical moiety —[CG$^7$G$^8$-(CG$^7$G$^9$)$_r$-CG$^7$G$^8$-H$_j$NR$^6$R$^7$]$^{j+}$), then j equals zero in the above formulas.

The foregoing amine-quaternary buffer compounds, and the method of buffer compounding a composition by use of these compounds, provides a novel and unexpectedly wide pH range of buffer compounding capability, with a consistent set of buffer compounding compounds. The present invention thereby provides a solution to the long-standing problem of providing such a versatile and wide-ranging buffer compounding system, and to the long-felt need for such buffer compounding capabilities, while at the same time affording low toxicity to living biologic organisms, low metal-binding properties, and low sensitivity to temperature change-induced pH changes, and having sufficient chemical compatibility between substances of interest and the buffering compounds, thus avoiding many of the problems resulting from chemical differences accompanying different buffer compounds used to obtain buffering over a wide range of pH.

DETAILED DESCRIPTION

Figure 1:
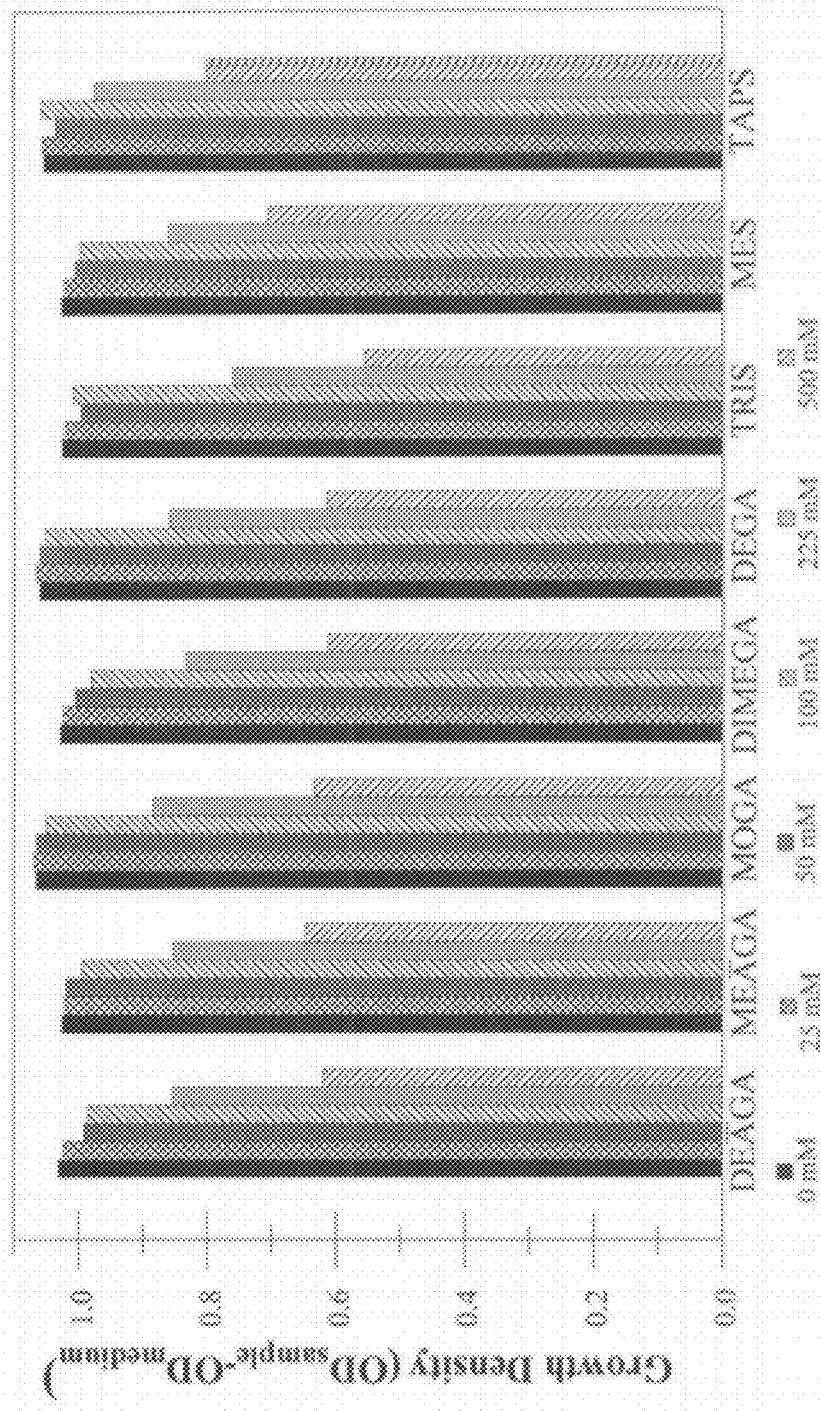
FIGS. 1-4 are graphs depicting the comparative growth of four different species of microorganisms in growth media containing buffer compounds within and not within the scope of the present invention, at various concentrations of the buffer compounds.

As used herein, reference to "buffer", "buffer compound" and use of the term "buffer" in terms including this root word, refers to a pH buffer compound.

As used herein, the term "non-interfering", when used in description of the counter-ion provided with the amine-quaternary ammonium buffer compounds to achieve electroneutrality of the overall buffer compound, means that the counter-ion does not interfere with solubility of the overall buffer compound, in that it does not result in the formation of an insoluble precipitate when in an aqueous system. It also refers to the absence of undesired interactions with other components in solution or in a mixture.

As used herein, the term "chemical bond" when used to define an optional substituent, refers to a direct, covalent bond between the atoms connected by the substituent. The term "carbon-carbon bond" means a chemical bond between two carbon atoms.

Throughout the disclosure and claims, the numerical limits of the disclosed ranges and ratios may be combined, and all intervening values are deemed to be disclosed by the disclosure of the ranges. Throughout the disclosure and claims, any member of a group may be deleted from the group. Throughout the disclosure and claims, all possible combinations of the various disclosed elements may be combined, and all such combinations are deemed to be included within the scope of the present invention. Unless otherwise specified, all temperatures are measured in degrees Celsius, all processes are conducted at room or ambient temperature, all pressures are atmospheric.

It is to be understood that unless specifically stated otherwise, reference to "a", "an", and/or "the" may include one or more than one, and that reference to an item in the singular may also include the item in the plural.

Certain buffer compounds of the present invention may exist in particular geometric or stereoisomeric forms. The present invention contemplates all such compounds, including cis and trans isomers, R and S (d & l) enantiomers including racemic mixtures thereof, diastereomers and other mixtures thereof, as falling within the scope of the invention. Additional asymmetric carbon atoms may be present in a substituent such as an alkyl group. All such isomers, as well as mixtures thereof, are intended to be included in this invention.

Particularly useful are cationic buffer compounds of the present invention in the hydroxide form, that is, with $OH^-$ as the counter-anion. The buffer compounds of the present invention in the hydroxide form have unique and useful properties in and of themselves. These buffer compounds are strong ionic hydroxides that do not contain inorganic cations and as a result have unique chemical and physical properties both in water and organic solvents.

An important issue relating to quaternary ammonium hydroxides is their stability toward dealkylation at high pH. Most of the buffer compounds disclosed herein have some high-pH stability (pH=14 in water, 23° C., 2 days), and many have substantial stability high-pH stability (pH=14 in water, 23° C., 3 months). Generally, compounds with β-hydroxyethyl groups attached to quaternary nitrogen atoms are least stable (hours to days), those with β-hydroxyethyl groups attached to tertiary nitrogen atoms are also less stable (days to weeks), and those without these groups are most stable (months), at such high pH. When high-pH stability is problematic and carbonate is an acceptable substitute for hydroxide, carbonate salts are readily prepared directly by metathesis or ion-exchange methods, or from hydroxide salts which are converted to carbonates using $CO_2$.

Some zwitterionic compounds described herein may not have counter-ions. Cationic buffer compounds described herein must contain counter-anions, and anionic buffer compounds disclosed herein must contain counter-cations. Unique counter-anions or counter-cations can impart important and useful properties to the buffer as a whole. During the synthesis of cationic buffers, various alkylating agents have been used. This leads to range of cationic buffers with different anions such as $Cl^-$, $Br^-$, $I^-$, $CH_3OSO_3^-$, $CH_3SO_3^-$, $CF_3SO_3^-$, $p\text{-}CH_3C_6H_4SO_3^-$, $CF_3CO_2^-$. The availability of the cationic buffers in the hydroxide form allows the synthesis of a wide range of buffer compounds by neutralizing the buffer hydroxide with certain acids including anions noted above: $NO_3^-$, $F^-$, $HCO_2^-$, $CH_3CO_2^-$, $SO_4^{2-}$, $HSO_4^-$, $CO_3^{2-}$, $HCO_3^-$, $PO_4^{3-}$, $HPO_4^{2-}$, $H_2PO_4^-$, $(CH_3O)_2PO_2^-$, $CH_3PO_3^{2-}$, $HPO_3^{2-}$, $CH_3PO_3H^-$, $H_2PO_3^-$, $H_2PO_2^-$, $B(OH)_4^-$ and similar anions where a methyl group is substituted with another small alkyl group ($C_1$-$C_4$). Another class of cationic buffers containing strongly hydrophobic anions are similarly prepared using acids corresponding to $CCl_3CO_2^-$, $CBr_3CO_2^-$, $BF_4^-$, $PF_6^-$, $ClO_4^-$. Yet another class of cationic buffers contain lipophillic anions which contain linear and branched aliphatic and aromatic groups (R=$C_4$-$C_{18}$). Buffers become more soluble in polar and nonpolar organic solvents as ionic species or ion-paired species when R=$C_4$-$C_{10}$. Furthermore, micelle formation and detergent properties in water can be obtained when R=$C_{12}$-$C_{18}$. These compounds are easily prepared from their acids yielding salts containing $RCO_2$, $RSO_3^-$, $ROSO_3^-$, $ROPO_3^{2-}$, $(RO)_2PO_2^-$, $RPO_3^{2-}$. In a few cases, useful anions are associated with unstable acids. In these cases, buffer compounds are prepared by ion-exchange methods forming $NO_2^-$, $HSO_3^-$, $SO_3^{2-}$, $S_2O_3^{2-}$ salts.

Anionic buffer compounds contain cationic counter-ions. Most commonly used are $Na^+$ and $K^+$ and, in some cases, $NH_4^+$ when the pH is sufficiently acidic. Organic cations are often acceptable when special solubility properties are needed: quaternary ammonium, di-quaternary ammonium, phosphonium, sulfonium, sulfoxonium salts are representative organic cations. When solubility allows and needs require, alkaline earth cations, lanthanide cations, transition metal cations and post transition metal cations may be acceptable counter-ions for anionic buffers.

Hydroxide Salts of Cationic Buffers—Acid Form of Anionic Buffers:

Particularly useful are cationic buffer compounds in the hydroxide form, that is with $OH^-$ as the counter-anion. In some cases these compounds can be prepared by metathesis reactions using $Ba(OH)_2$, $KOH$, $NaOH$, $Ag_2O$ in water or polar organic solvents. More preferably, these compounds are prepared by electrolysis/electrodialysis in water or by ion-exchange methods in water or polar organic solvents. The buffers in the hydroxide form have unique and useful properties in and of themselves. Strong ionic hydroxides not containing inorganic cations have unique chemical and physical properties both in water and organic solvents. One important use of the hydroxide salts is the convenient preparation of many different compounds by simple neutralization reactions using weak or strong acids (see below).

The acid forms of the anionic buffers allow the user to make any desired salt by using the appropriate inorganic hydroxides, $NaOH$, $KOH$, $NH_4OH$. Furthermore, anionic buffer acids and cationic buffer hydroxides can be mixed to form mixed buffering systems without producing unwanted salt.

Buffering Cations with Buffering Anions:

A very useful and unique property of the buffer compounds in accordance with another embodiment of the present invention is the combination of cationic buffer compounds with anionic buffer compounds, including in particular anionic buffer compounds in accordance with embodiments of the present invention, as well as conventional anionic buffer compounds. The results are useful buffer combinations with wide-range buffering capabilities at reasonable concentrations. In some applications, cationic buffers require a passive, unreactive anion. However, in other applications, a buffering anion is perfectly acceptable. Most of the cationic buffers described herein are compatible with many buffering anions forming salts having acceptable solubility properties in aqueous solutions. This includes formate, acetate, bicarbonate, hydrogenphosphate, dihydrogenphosphate and borate. This also includes a wide range of commonly used anionic buffers that contain aminoalkanesulfonic acids and anionic buffers of the type described here. As noted, in one embodiment, cationic buffers and anionic buffers, each within the scope of the present invention, may be combined for use to obtain buffering over an even wider range of pH. There are many useful combinations with varying concentration ratios that cannot all be listed here. The availability of the cationic buffers in hydroxide form and the anionic buffers in acid (protonated) form allows one to make many buffering combinations without generating unwanted salt (e.g., NaCl) that otherwise would lead to higher ionic-strength, higher conductivity and higher osmolality. One may select alternating combinations of cationic and anionic buffers whose $pK_a$ values are spaced about 1 to about 2 log K units apart. Initially, approximately equal concentrations are chosen. Of course, additional acids (e.g., HCl), bases (e.g., NaOH) and salts (e.g., NaCl) can be added as may be needed. Many useful binary, ternary and even higher combinations are possible. Several examples of both anionic and cationic buffers are given for illustration, in which any one of the cationic buffers may be combined with one of the anionic buffers, to provide such control of the buffering range. For well known buffers (MOPSO, MOPS, CHES, MES, TES, HEPES), consult standard compilations for chemical structures and abbreviations. For new cationic buffers described here, see the exemplary structural formulae and abbreviations near the end of the present specification.

aqueous solubility and have similar effects on the $pK_a$ of the amine, yet do not bind metals at all and are stable at high pH. In the present invention, phosphonomethyl groups and carboxymethyl groups attached to the tertiary nitrogen atom can increase metal binding, but this increase does not usually increase metal binding when these groups are attached to the quaternary ammonium nitrogen atom.

Another useful property of biological buffers is low toxicity to humans, animals and microorganisms and an absence of cellular growth inhibition. The buffer compounds in accordance with embodiments of the present invention exhibit little or no toxicity to animals and microorganisms and have shown little or no growth inhibition in such systems. Traditional growth media for microorganisms and fermentation media contain natural and added buffer compounds, usually of the anionic type. It is known that certain cationic detergents such as myristylbenzyldimethylammonium chloride, have biostatic and biocidal properties. The buffer compounds in accordance with embodiments of the present invention, when tested in microbial growth assays, show substantially no growth inhibition.

| MOGA ($CO_3^{2-}$) | MOPSO (H+) | DIMEPA (OH−) | CHES (H+) | |
|---|---|---|---|---|
| 5.6 | 6.9 | 8.1 | 9.4 | |
| CHEMP (OH−) | MES (H+) | MEEPA (OH−) | Boric Acid | TEXA (OH−) |
| 5.0 | 6.1 | 7.3 | 9.0 | 10.3 |
| MEDBOC (OH−) | Acetic Acid | DIMEQ (OH−) | TES (H+) | DIMEBA (OH−) |
| 3.0 | 4.6 | 6.1 | 7.5 | 8.9 |
| HEPES ($pK_{a1}$) | Acetic Acid | DIMEQ (OH−) | HEPES ($pK_{a2}$) | DEPA (OH−) |
| 3.0 | 4.6 | 6.1 | 7.5 | 8.7 |
| MEDBOC (OH−) | Acetic Acid | MOPA (OH−) | MOPS (H+) | DEPA (OH−) |
| 3.1 | 4.6 | 5.8 | 7.1 | 8.7 |
| Methoxyacetic Acid | TMP (OH−) | | | |
| 3.3 | 4.3 | | | |

An important property of useful biological buffer compounds is having low metal-binding properties. The buffer compounds in accordance with most embodiments of the present invention exhibit little or no metal-binding (complexing) activity. While most anionic buffers such as acetate and phosphate bind metals (alkaline earth metals and transition metals) to some extent, this is less of a problem with cationic, amine-based buffers. Such buffers have no affinity for calcium and magnesium and other alkaline earth metals. While ammonia can be a good ligand for some transition metals, tertiary amines bind much more weakly, especially those tertiary amines containing larger alkyl groups (ethyl and larger). While metal chelation can be problematic, especially for some ordinary diamines, α-aminocarboxylic acids, α-aminophosphonic acids and related compounds, this is not true for the amine-quat buffers described here because one of the two nitrogen atoms of the di-tertiary amines has been "quaternized", thereby replacing one of the amine nitrogen atoms by a quaternary nitrogen atom. Not only is chelation eliminated, but the neighboring positive charge strongly inhibits binding of metals to the remaining tertiary nitrogen. Though usually benign, contained ethanolamine groups (2-hydroxyethylamino) that are often found in common buffers (e.g., TRIS, HEPES, MOPSO and triethanolamine) can under some circumstances bind to transition metal cations (e.g., $Cu^{2+}$, $Zn^{2+}$) in aqueous solution. 2-Hydroxyethyl groups improve water solubility and bio-compatibility, and they also lower the $pK_a$ values of the attached amine; however, these groups sometimes lead to weak metal-binding and to reduced chemical stability at high pH. However, in the present invention, the 2-methoxyethyl groups also enhance As reported in more detail below, when dose-response, growth-inhibition studies are carried out for four different common microorganisms using five cationic buffers in accordance with the present invention and three standard neutral/anionic buffers (TRIS, MES, TES) under optimized growth conditions (temperature, time, medium, pH) at varying concentrations for all five cationic buffers, there is observed no evidence of acute toxicity, and at buffer concentrations of 100 mM and below, the cationic buffers show no growth inhibition. At 200-500 mM, all buffers, including the standard buffers, display some growth inhibition (see below). Thus, these buffers, in accordance with the present invention, demonstrate low toxicity to microorganisms.

It should be noted that there are no observed compatibility issues between the buffer compounds in accordance with the present invention and the growth-media used (precipitation, off-color, off-odor) either before or after sterilization.

As described in the above Summary, in various embodiments, the present invention relates to a protonated or un-protonated amine-quaternary ammonium compound, and a method of buffering a chemical or biological composition, comprising adding to the composition an effective buffering amount of at least one protonated or un-protonated amine-quaternary ammonium compound, in which the amine-quaternary ammonium compound has a general formula:

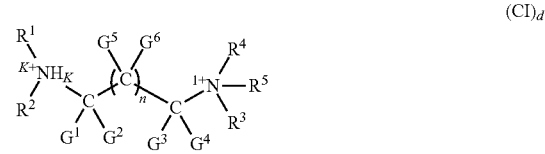

(CI)$_d$ wherein the variables are as defined above and further explained in the following.

In determining the number of carbon atoms separating the two nitrogen atoms, n has integer values in the range 0-4. Thus, the monoquaternized N-containing molecule may have a 1,2-ethylenediamine structure (n=0), a 1,3-propanediamine structure (n=1), a 1,4-butanediamine structure (n=2), a 1,5-pentanediamine structure (n=3) or a 1,6-hexanediamine structure (n=4) (in which, in each case, one of the amines is quaternary). If fewer than two carbon atoms separate the nitrogen atoms, in which one is quaternized, the $pK_a$ of the remaining tertiary nitrogen atom falls outside the range of useful values and chemical stability is decreased (hydrolysis). If more than six carbon atoms separate the nitrogen atoms, the molecular weights become overly large with little change in $pK_a$.

As noted in the preamble, the buffer compound may be protonated or un-protonated. Thus, when k or j is 0, the tertiary nitrogen atom of the buffer compound is un-protonated, and when either k or j or both is(are) 1, the tertiary nitrogen atom of the buffer compound is protonated. Of course, as will be recognized, various of the G and/or the R groups may be in a protonated or un-protonated state as well. However, when the presently disclosed and claimed buffer compounds are designated as being protonated or un-protonated, this designation refers to the state of the tertiary (e.g., amine) nitrogen atom, and whether it has been protonated. It is noted that, as in chemistry in general, when an un-protonated compound, such as an amine, becomes protonated, it is considered to be a new and different compound than was the un-protonated compound. For example, protonated and un-protonated amine compounds generally have different CAS (Chemical Abstracts) numbers.

In the buffer compounds in accordance with the present invention, each $G^1$, $G^3$ and $G^5$ is a chemical moiety independently selected from the group —H, —CH$_3$, —C$_2$H$_5$, or is a component of a cyclic chemical moiety. The present inventors have discovered that the most versatile and useful buffer compounds in accordance with the present invention are those in which each of the $G^1$, $G^3$ and $G^5$ is a relatively small group, hydrogen, methyl or ethyl. While it is possible that larger organic groups could be used, e.g., propyl or butyl, as the length or size of the organic group increases beyond the smaller groups, the utility of the buffer compounds decreases as molecular weight increases.

In the buffer compounds in accordance with the present invention, each $G^2$ and $G^4$ group present in the compound is a chemical moiety independently selected from the group —H, —CH$_3$, —CH$_2$OH, —C$_2$H$_5$, —CO$_2$H, —SO$_3$H, —PO$_3$H$_2$, —CO$_2^-$, —SO$_3^-$, —PO$_3$H$^-$ and —PO$_3^{2-}$ or is a component of a cyclic chemical moiety. The present inventors have discovered that, by providing this substituent with a greater range of variability, adverse effects on the buffering characteristics of the buffer compound can be obtained. By introducing one or more of the —H, —CH$_3$, —CH$_2$OH, —C$_2$H$_5$, —CO$_2$H, —SO$_3$H, —PO$_3$H$_2$, —CO$_2^-$, —SO$_3^-$, —PO$_3$H$^-$, and —PO$_3^{2-}$ groups, the buffer compounding properties of the compound can be precisely adjusted and controlled. The foregoing definition of $G^2$ and $G^4$ provides the possibility of some $G^2$ and $G^4$ groups in the compound being one or a mixture of the —CH$_2$OH, —CO$_2$H, —SO$_3$H, —PO$_3$H$_2$, —CO$_2^-$, —SO$_3^-$, —PO$_3$H$^-$, and —PO$_3^{2-}$ groups, while others of the $G^2$ and $G^4$ groups in the compound being one or a mixture of the —H, —CH$_3$ and —C$_2$H$_5$ groups.

In the buffer compounds in accordance with the present invention, each $G^6$ group present in the compound is a chemical moiety independently selected from the group the —H, —OH, —CH$_3$, —OCH$_3$, —CH$_2$OH, —C$_2$H$_5$, —CO$_2$H, —SO$_3$H, —PO$_3$H$_2$, —CO$_2^-$, —SO$_3^-$, —PO$_3$H$^-$, and —PO$_3^{2-}$. The present inventors have discovered that, by providing this substituent with a greater range of variability, dramatic effects on the buffering characteristics of the buffer compound can be obtained. By introducing one or more of the —H, —OH, —CH$_3$, —OCH$_3$, —CH$_2$OH, —C$_2$H$_5$, —CO$_2$H, —SO$_3$H, —PO$_3$H$_2$, —CO$_2^-$, —SO$_3^-$, —PO$_3$H$^-$, and —PO$_3^{2-}$ groups, the buffer compounding properties of the compound can be further precisely adjusted and controlled. By combining the variations provided above with the value of n, the number of $G^6$ groups in the molecule can range from zero to four, and thus the number of groups, if any, other than —H, —CH$_3$, —C$_2$H$_5$ can be controlled. The foregoing definition of $G^6$ provides the possibility of some $G^6$ groups in the compound being one or a mixture of the —OH, —CH$_2$OH, —OCH$_3$, —CO$_2$H, —SO$_3$H, —PO$_3$H$_2$, —CO$_2^-$, —SO$_3^-$, —PO$_3$H$^-$, and —PO$_3^{2-}$ groups, while others of the $G^6$ groups in the compound being one or a mixture of the —H, —CH$_3$, —C$_2$H$_5$ groups.

In the buffer compounds in accordance with the present invention, each $R^1$, $R^2$, $R^3$, $R^4$ and $R^5$ group can be independently selected to yield a variety of compounds, including one or more or combinations of acyclic structures, structures containing carbocyclic rings, heterocyclic rings, and bicyclic structures, and structures including the introduction of additional functional groups for any of the $R^1$, $R^2$, $R^3$, $R^4$ and $R^5$ groups that is not otherwise used in forming these variations, and including combinations of any of the foregoing. The following disclosure covers various options and combinations of the options, all of which can be suitably selected to obtain a very wide range of buffer compounding properties, across the entire range of pH, and including some or all of the specific benefits described above in the summary of the invention.

In the buffer compounds in accordance with the present invention, in some embodiments, each $R^1$, $R^2$, $R^3$, $R^4$ and $R^5$ is an chemical moiety independently selected from —CH$_3$, —C$_2$H$_5$, —CH(CH$_3$)$_2$, -cyclohexyl, —C$_2$H$_4$OH, —C$_2$H$_4$OCH$_3$, —(CH$_2$)$_{2-3}$NHC(O)CH$_3$, —(CH$_2$)$_{2-3}$N(CH$_3$)C(O)CH$_3$, —(CH$_2$)$_{1-3}$C(O)NH$_2$, —(CH$_2$)$_{1-3}$C(O)NHCH$_3$, —(CH$_2$)$_{1-3}$C(O)N(CH$_3$)$_2$, —CH$_2$(CG$^5$G$^6$)$_m$SO$_3^-$, —CH$_2$(CG$^5$G$^6$)$_m$CO$_2^-$, —CH$_2$(CG$^5$G$^6$)$_m$CO$_2$H, —CH$_2$(CG$^5$G$^6$)$_m$PO$_3^{2-}$, —CH$_2$(CG$^5$G$^6$)$_m$PO$_3$H$^-$, —CH$_2$(CG$^5$G$^6$)$_m$PO$_3$H$_2$ with m being 0, 1, 2 or 3, or is a component of the cyclic chemical moiety, or $R^5$ is a chemical moiety —[CG$^7$G$^8$-(CG$^7$G$^9$)$_r$-CG$^7$G$^8$-H$_j$NR$^6$R$^7$]$^{j+}$, wherein each $G^7$ is a chemical moiety independently selected from —H, —CH$_3$, —C$_2$H$_5$, each $G^8$ is a chemical moiety independently selected from —H, —CH$_3$, —CH$_2$OH, —C$_2$H$_5$, —CO$_2$H, —SO$_3$H, —PO$_3$H$_2$, —CO$_2^-$, —SO$_3^-$, —PO$_3$H$^-$ and —PO$_3^{2-}$, $G^9$ is a chemical moiety independently selected from —H, —CH$_3$, —CH$_2$OH, —C$_2$H$_5$, —OH, —OCH$_3$, —OC$_2$H, —SO$_3$H, —PO$_3$H$_2$, —CO$_2^-$, —SO$_3^-$, —PO$_3$H$^-$, and —PO$_3^{2-}$, r has integer values in the range 0-4, and j is 0 or 1, and each $R^6$ and $R^7$ is an chemical moiety independently selected from —CH$_3$, —C$_2$H$_5$, —CH(CH$_3$)$_2$, -cyclohexyl, —C$_2$H$_4$OH, —C$_2$H$_4$OCH$_3$, —(CH$_2$)$_{2-3}$NHC(O)CH$_3$, —(CH$_2$)$_{2-3}$N(CH$_3$)C(O)CH$_3$, —(CH$_2$)$_{1-3}$C(O)NH$_2$, (CH$_2$)$_{1-3}$C(O)NHCH$_3$, —(CH$_2$)$_{1-3}$C(O)N(CH$_3$)$_2$, —CH$_2$(CG$^5$G$^6$)$_m$SO$_3^-$, —CH$_2$(CG$^5$G$^6$)$_m$CO$_2^-$, —CH$_2$(CG$^5$G$^6$)$_m$CO$_2$H, —CH$_2$(CG$^5$G$^6$)$_m$PO$_3^{2-}$, —CH$_2$(CG$^5$G$^6$)$_m$PO$_3$H$^-$, —CH$_2$(CG$^5$G$^6$)$_m$PO$_3$H$_2$ with m being 0, 1, 2 or 3. In the foregoing, the $G^5$ and $G^6$ groups are defined as above in the general definitions of the other G groups. The foregoing substituents for $R^1$, $R^2$, $R^3$, $R^4$ and $R^5$ may be selected independently and combined with any of the following combinations of $R^1$, $R^2$, $R^3$, $R^4$ and $R^5$ and $G^1$, $G^2$, $G^3$, $G^4$, $R^3$, $R^4$ and $R^5$ and $G^1$, $G^5$ and $G^6$ groups, as defined herein.

Exemplary buffer compounds in accordance with the foregoing embodiments include structures as shown hereinbelow.

As noted above, in some embodiments, the various substituents G and R may be combined into cyclic chemical moieties. The following describes various cyclic chemical moieties comprised within the scope of the present invention. In embodiments in which the amine-quaternary ammonium buffer compound comprises a cyclic chemical moiety, the cyclic chemical moiety is one or more selected from (a), (b), (c), (d), (e), (f) and (g):

Cyclic Group (a):

In the buffer compounds in accordance with the present invention, in some embodiments, (a) one or more pairs of $R^1$, $R^2$, $R^3$, $R^4$, and $R^5$, forms a single chemical moiety such that the pair $R^1/R^2$ and/or the pair $R^3/R^4$ and/or the pair $R^3/R^5$ and/or the pair $R^4/R^5$ is individually and independently —CH$_2$CH$_2$CH$_2$CH$_2$—, —CH$_2$CH(OH)CH(OH)CH$_2$—, —CH$_2$CH$_2$CH$_2$CH$_2$CH$_2$—, —CH$_2$CH$_2$OCH$_2$CH$_2$—, —CH$_2$CH$_2$CH(OH)CH$_2$CH$_2$—, —CH$_2$CH$_2$N(C(O)G$^1$)CH$_2$CH$_2$—, —CH$_2$C(O)N(G$^1$)CH$_2$CH$_2$—, —CH$_2$CH(OH)CH(OH)CH$_2$—, =C(NG$^1_2$)$_2$,

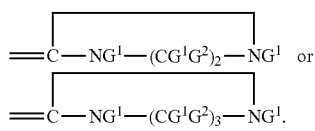

Thus, in accordance with these embodiments, the pair $R^1/R^2$ and/or the pair $R^3/R^4$ and/or the pair $R^3/R^5$ and/or the pair $R^4/R^5$ individually and independently forms a N-containing heterocyclic ring, a morpholinium ring, or a guanidinium group. In the buffer compounds in accordance with these embodiments, either or both the non-quaternized nitrogen atom or the quaternary nitrogen atom may be part of a ring structure, or may be part of a guanidinium moiety. In the buffer compounds in these embodiments, the remaining substituents for $R^1$, $R^2$, $R^3$, $R^4$ and $R^5$ may be selected independently and combined with any of the foregoing definitions of the $R^1$, $R^2$, $R^3$, $R^4$ and $R^5$ and $G^1$, $G^2$, $G^3$, $G^4$, $G^5$ and $G^6$ groups.

Exemplary buffer compounds in accordance with the foregoing embodiments include the following, in which, in the general formula for the present amine-quaternary ammonium compound, for the pair $R^1/R^2$ the un-protonated fragment:

the pair $R^1/R^2$ may form the following exemplary groups, and the remainder of the amine-quaternary ammonium compound may be as described in any of the remaining combinations:

It is recognized that the un-protonated amine nitrogen in the foregoing exemplary groups may be protonated, as described elsewhere herein.

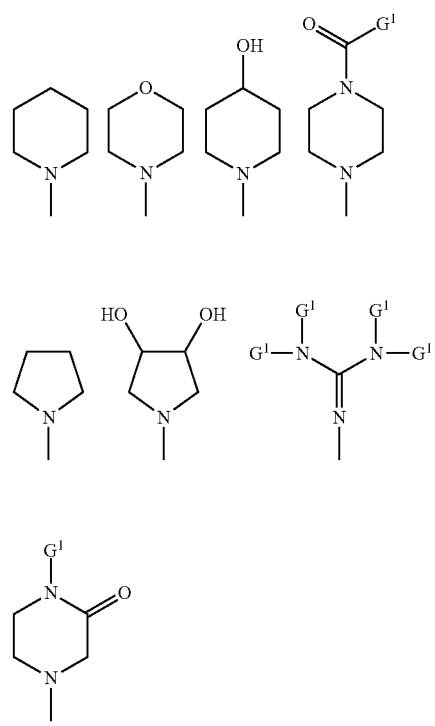

Exemplary buffer compounds in accordance with the foregoing embodiments include the following, in which, in the general formula for the present amine-quaternary ammonium compound, for the quaternary fragment:

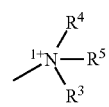

the pair $R^3/R^4$ (or, equivalently, the pair formed by $R^3/R^5$ or $R^4/R^5$) may be combined to form the following exemplary groups, and the remainder of the amine-quaternary ammonium compound may be as described in any of the remaining combinations:

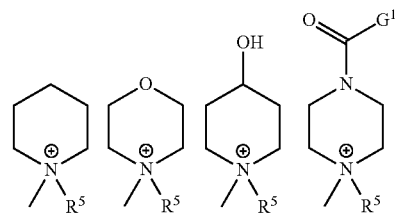

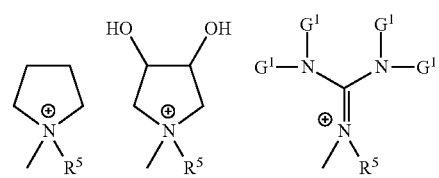

-continued

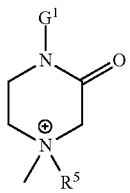

In some embodiments, in accordance with the foregoing pairing descriptions, both the pair $R^1/R^2$ and one of the pairs $R^3/R^4$, or $R^3/R^4$ or $R^3/R^4$, may form a chemical moiety such that both pairs are present in the same buffer compound. Thus, in accordance with these embodiments, both the pair $R^1/R^2$ and one of the pairs $R^3/R^4$, or $R^3/R^5$ or $R^4/R^5$, individually and independently may form multicyclic N-containing heterocyclic rings, and one or both of the two pairs may form a guanidine moiety, and when one pair forms a quanidinium group, the other pair may form any of the foregoing cyclic groups.

In all of the foregoing embodiments of the pairs $R^1/R^2$, $R^3/R^4$, $R^3/R^5$, and $R^4/R^4$, the remainder of the amine-quaternary ammonium compound may be as described elsewhere herein, i.e., any unpaired $R^1$, $R^2$, $R^3$, $R^4$ and $R^5$ and each of the $G^1, G^2, G^3, G^4, G^5$ and $G^6$ groups, and other variables, may be suitably selected as defined herein.

Cyclic Group (b):

In the buffer compounds in accordance with the present invention, in some embodiments, one or more pairs of $R^1$, $R^2$, $R^3$, $R^4$ and $R^5$ may form a single chemical moiety such that one or more of $R^1/R^3$, $R^1/R^4$, $R^1/R^5$, $R^2/R^3$, $R^2/R^4$ or $R^2/R^5$, taken as a combined group, is individually and independently —(CG$^1$G$^2$)$_g$- with g being 2 or 3 and n being 0 or 1. Thus, in accordance with these embodiments, the combined one or more pairs, together with the remainder of the molecule, form a six-membered ring (g=2, n=0) or a seven-membered ring (g=2, n=1 or g=3, n=0), or eight-membered ring (g=3, n=1) containing both the non-quaternary-nitrogen atom and the quaternary-nitrogen atom in the ring or rings thus formed. Furthermore, in one embodiment, when both the combined $R^1/R^3$ and the combined $R^2/R^4$ (or the combined $R^1/R^4$ and the combined $R^2/R^3$) groups are —(CG$^1$G$^2$)$_g$-, a bicyclic buffer compound is formed which can contain 6-, 7- or 8-membered rings. In the buffer compounds in accordance with these embodiments, both nitrogen atoms are included in the ring or rings. In the buffer compounds in accordance with these embodiments, the remaining substituents for $R^1$, $R^2$, $R^3$, $R^4$ and $R^5$ may be selected independently and combined with any of the foregoing definitions of the $R^1$, $R^2$, $R^3$, $R^4$ and $R^5$ and $G^1, G^2, G^3, G^4, G^5$ and $G^6$ groups.

Exemplary buffer compounds in accordance with the foregoing embodiments include the following:

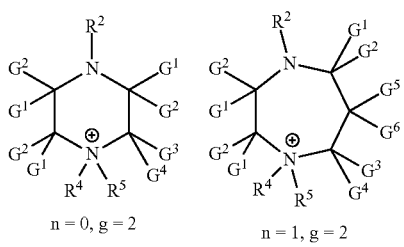

n = 0, g = 2    n = 1, g = 2

An exemplary bicyclic buffering compound in accordance with the foregoing embodiments include the following structure:

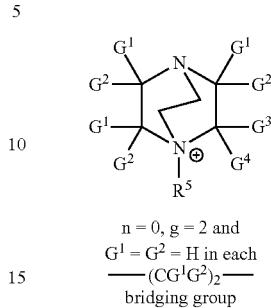

n = 0, g = 2 and
G$^1$ = G$^2$ = H in each
—(CG$^1$G$^2$)$_2$—
bridging group

In all of the foregoing embodiments of the pairs of $R^1/R^3$, $R^1/R^4$, $R^1/R^5$, $R^2/R^3$, $R^2/R^4$ or $R^2/R^5$, the remainder of the amine-quaternary ammonium compound may be as described elsewhere herein, i.e., any unpaired $R^1$, $R^2$, $R^3$, $R^4$ and $R^5$ and the $G^1, G^2, G^3, G^4, G^5$ and $G^6$ groups, and other variables, may be suitably selected as defined herein.

Cyclic Group (c):

In the buffer compounds in accordance with the present invention, in some embodiments, one pair selected from $G^1$ and $G^3$, $G^2$ and $G^4$, $G^1$ and $G^4$ or $G^2$ and $G^3$, taken as a pair, may form a single chemical moiety —(CG$^1$G$^6$)$_q$- with q having integer values 0-4, n as defined above in the general formula, and the sum of q and n having integer values 3 or 4, and when q=0, —(CG$^1$G$^6$)$_q$- is a single carbon-carbon bond. The structures formed in these embodiments are five-membered (q+n=3) or six-membered (q+n=4) carbocyclic rings. As will be observed, when n=0, the —(CG$^1$G$^6$)$_q$— group becomes a single carbon-carbon bond, the two nitrogen atoms are separated by two carbon atoms, and when n=1, the two nitrogen atoms are separated by three carbon atoms. The number of G$^6$ groups will be 3 or 4, equal to the total of (q+n). In the buffer compounds in accordance with these embodiments, the substituents for $R^1$, $R^2$, $R^3$, $R^4$ and $R^5$ may be selected independently and combined with any of the foregoing independent definitions for the remaining $G^1, G^2, G^3, G^4, G^5$ and $G^6$ groups. The $G^1$ and $G^6$ groups in the —(CG$^1$G$^6$)$_q$- group(s) are defined independently as set forth above for the $G^1$ and $G^6$ groups.

Exemplary buffer compounds in accordance with the foregoing embodiments, when $G^1$ and $G^3$, $G^2$ and $G^4$, $G^1$ and $G^4$ or $G^2$ and $G^3$ are taken as a pair as described, include the following six-membered rings:

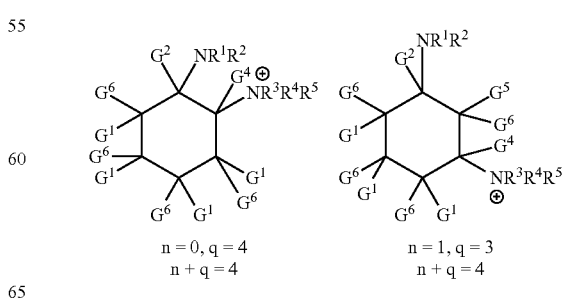

n = 0, q = 4    n = 1, q = 3
n + q = 4       n + q = 4

-continued

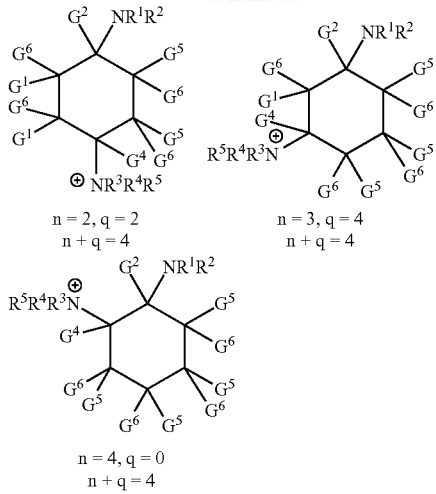

and include the following five-membered rings:

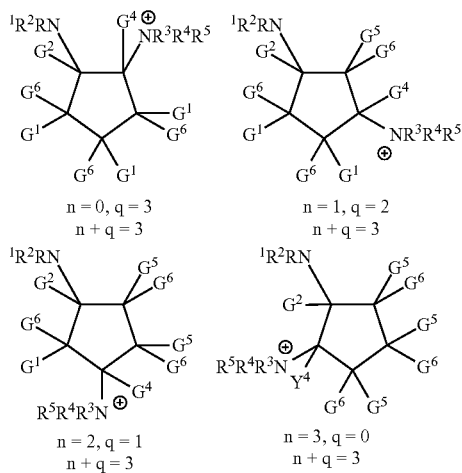

In all of the foregoing embodiments of the pairs of $G^1$ and $G^3$, $G^2$ and $G^4$, $G^1$ and $G^4$ or $G^2$ and $G^3$, the remainder of the amine-quaternary ammonium compound may be as described elsewhere herein, i.e., the $R^1$, $R^2$, $R^3$, $R^4$ and $R^5$ and the unpaired $G^1$, $G^2$, $G^3$, $G^4$, $G^5$ and $G^6$ groups, and other variables, may be suitably selected as defined herein.

Cyclic Group (d):

In the buffer compounds in accordance with the present invention, in some embodiments, one or more pair of $G^1$ and $G^2$, $G^3$ and $G^4$, and/or $G^5$ and $G^6$ forms a single chemical moiety such that the pair is individually and independently —$(CG^1G^6)_w$- with w having integer values 4-5. As will be observed, the structures formed in these embodiments are 5- or 6-membered carbocyclic rings in which neither the amine nitrogen nor the quaternary nitrogen are members of the thus-formed ring, although either nitrogen atom may be a member of another ring, depending on the definitions of the variables in the above general formula for the amine-quaternary ammonium buffer compound. As will be observed, in the $G^5$ and $G^6$ pair, n must be one or more, and if n is greater than one the possibility arises to have multiple —$(CG^1G^6)_w$- rings. In one embodiment, when n is two or more, all or less than all of the —$(CG^5G^6)_n$- groups can from the —$(CG^1G^6)_w$- ring(s).

Exemplary buffer compounds in accordance with the foregoing embodiments, when $G^1$ and $G^2$, $G^3$ and $G^4$, or $G^5$ and $G^6$ are taken as a pair as described, include the following five-membered (w=4) and six-membered (w=5) rings:

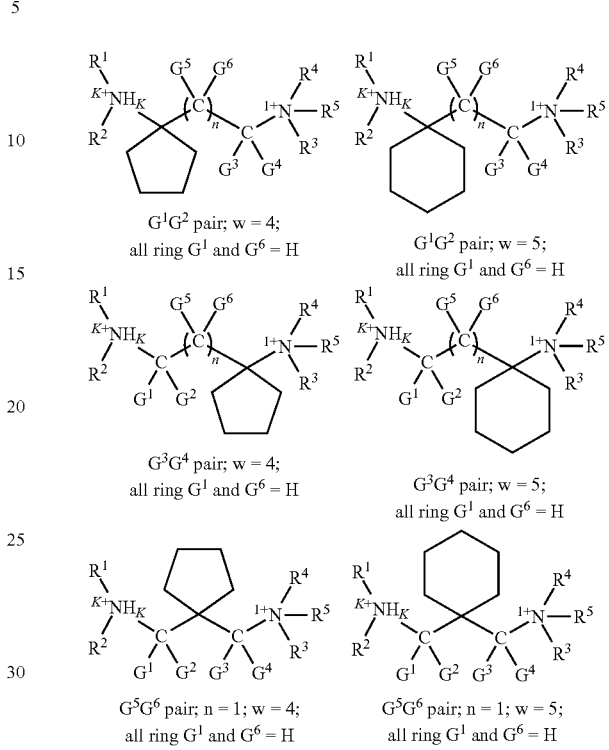

In all of the foregoing embodiments of the pairs of $G^1$ and $G^2$, $G^3$ and $G^4$, and/or $G^5$ and $G^6$, the remainder of the amine-quaternary ammonium compound may be as described elsewhere herein, i.e., the $R^1$, $R^2$, $R^3$, $R^4$ and $R^5$ and the unpaired $G^1$, $G^2$, $G^3$, $G^4$, $G^5$ and $G^6$ groups, and other variables, may be suitably selected as defined herein.

Cyclic Group (e):

In the buffer compounds in accordance with the present invention, in some embodiments, one or more pair of $R^1$ and $G^3$, $R^1$ and $G^4$, $R^2$ and $G^3$, $R^2$ and $G^4$, $R^3$ and $G^1$, $R^3$ and $G^2$, $R^4$ and $G^1$, $R^4$ and $G^2$, $R^5$ and $G^1$, and/or $R^5$ and $G^2$ forms a single chemical moiety such that the pair is individually and independently —$(CG^1G^2)_s$- with s having integer values 1-3, n having integer values 0-2 and the sum of s and n having integer values 2-3. It is noted that, in these embodiments, the range of n is restricted to 0-2, rather than 0-4 for the general formula and various other embodiments. The structures formed in these embodiments are five-membered (s+n=2) or six-membered (s+n=3) nitrogen containing heterocyclic rings, in which either but not both of the non-quaternary nitrogen atom or the quaternary nitrogen atom may be in any given ring. That is, in accordance with the embodiments of cyclic group (e), there is no embodiment in which both the non-quaternary nitrogen atom and the quaternary nitrogen atom are in the same ring. In some embodiments, when a pair from each of the two groups, e.g., both $R^1/G^3$ and $R^3/G^1$, are —$(CG^1G^2)_s$- groups, a bicyclic structure can be formed, in which the rings may be five-, six- or seven-membered, depending on the choices for the values of s and n. As will be observed, when n=0, the two nitrogen atoms are separated at a minimum by two carbon atoms, and the molecule contains no $G^6$ group, and when n=1, the two nitrogen atoms are separated at a minimum by three carbon atoms, and the molecule contains a $G^6$ group. In the buffer compounds in accordance with these embodiments, the substituents for the remaining $R^1$, $R^2$, $R^3$, $R^4$ and $R^5$ may be selected independently and combined with any of the foregoing independent definitions for the remaining $G^1$, $G^2$, $G^3$, $G^4$, $G^5$ and $G^6$ groups. The $G^1$ and $G^2$ groups in the —$(CG^1G^2)_s$- group(s) are defined independently as set forth above for all of the $G^1$, $G^2$, $G^3$, $G^4$ and $G^5$ groups.

Exemplary buffer compounds in accordance with the foregoing embodiments when one of $R^1$ and $G^3$, $R^1$ and $G^4$, $R^2$ and $G^3$, $R^2$ and $G^4$, are taken as a pair and form a chemical moiety such that the pair is a —$(CG^1G^2)_s$- group, include the following:

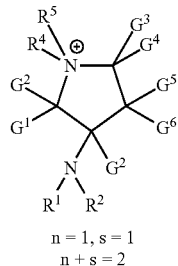
n = 1, s = 1
n + s = 2

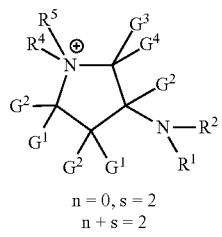
n = 0, s = 2
n + s = 2

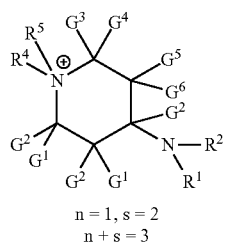
n = 1, s = 2
n + s = 3

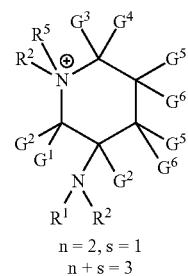
n = 2, s = 1
n + s = 3

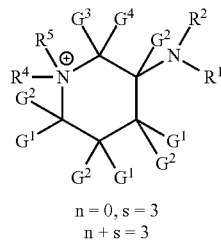
n = 0, s = 3
n + s = 3

Exemplary buffer compounds in accordance with the foregoing embodiments when one of one of $R^3$ and $G^1$, $R^3$ and $G^2$, $R^4$ and $G^1$, or $R^4$ and $G^2$, are taken as a pair and form a chemical moiety such that the pair is a —$(CG^1G^2)_s$- group, include the following:

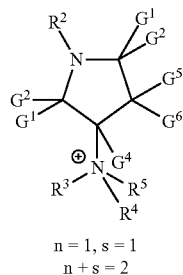
n = 1, s = 1
n + s = 2

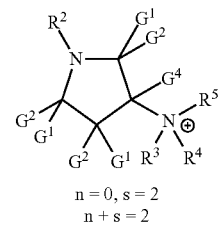
n = 0, s = 2
n + s = 2

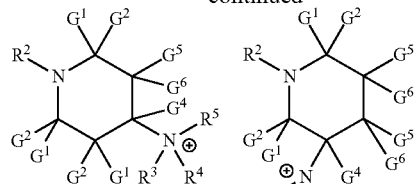
n = 1, s = 2
n + s = 3

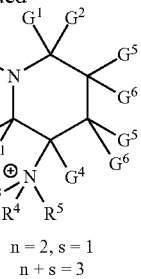
n = 2, s = 1
n + s = 3

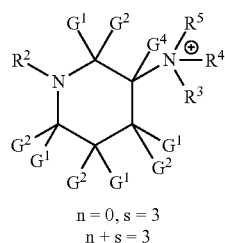
n = 0, s = 3
n + s = 3

In all of the foregoing embodiments of the pairs of $R^1$ and $G^3$, $R^1$ and $G^4$, $R^2$ and $G^3$, $R^2$ and $G^4$, and/or $R^3$ and $G^1$, $R^3$ and $G^2$, $R^4$ and $G^1$, $R^4$ and $G^2$, $R^5$ and $G^1$, or $R^5$ and $G^2$, the remainder of the amine-quaternary ammonium compound may be as described elsewhere herein, i.e., the unpaired $R^1$, $R^2$, $R^3$, $R^4$ and $R^5$ and the $G^1$, $G^2$, $G^3$, $G^4$, $G^5$ and $G^6$ groups, and other variables, may be suitably selected as defined herein.

Cyclic Group (f):

In the buffer compounds in accordance with the present invention, in some embodiments, one or more pair of $R^1$ and $G^5$, $R^1$ and $G^6$, $R^2$ and $G^5$, $R^2$ and $G^6$, $R^3$ and $G^5$, $R^3$ and $G^6$, $R^4$ and $G^5$, $R^4$ and $G^6$, $R^5$ and $G^5$, and/or $R^5$ and $G^6$ forms a single chemical moiety such that the pair is individually and independently —$(CG^1G^2)_v$- with v having integer values 0-3, n having integer values 1-4 and the sum of v and n having integer values 3-4 and, when v=0, —$(CG^1G^2)_0$- is a single carbon-carbon bond. The structures formed in these embodiments are five-membered, six-membered or larger nitrogen-containing heterocyclic rings, in which either but not both of the non-quaternary nitrogen atom or the quaternary nitrogen atom may be in any given ring. That is, in accordance with the embodiments of cyclic group (e), there is no embodiment in which both the non-quaternary nitrogen atom and the quaternary nitrogen atom are in the same ring.

Exemplary buffer compounds in accordance with the foregoing embodiments when one of one of $R^1$ and $G^5$, $R^1$ and $G^6$, $R^2$ and $G^5$, $R^2$ and $G^6$, are taken as a pair and form a chemical moiety such that the pair is a —$(CG^1G^2)_v$- group, for the pairs including $R^1$ (similar for pairs including $R^2$), include compounds having the following structures:

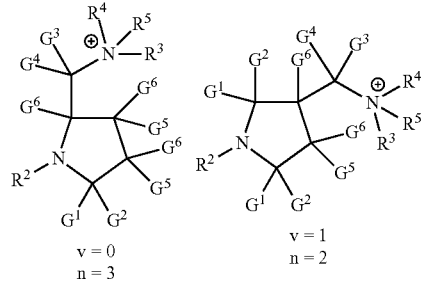

v = 0
n = 3 v = 1
n = 2

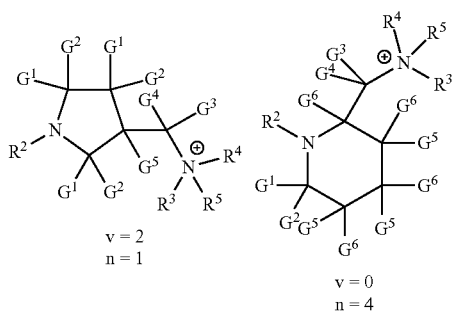
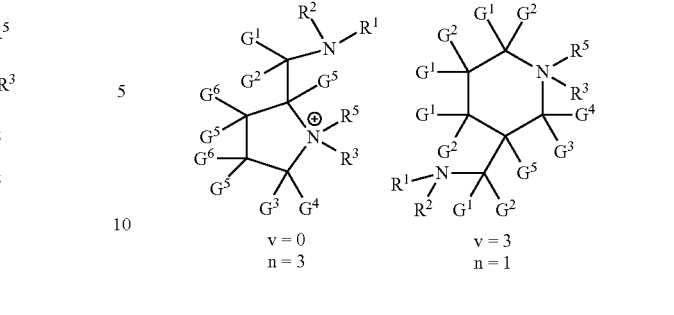

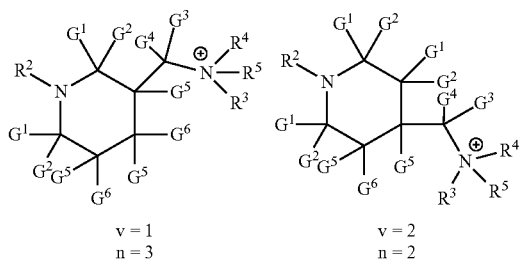
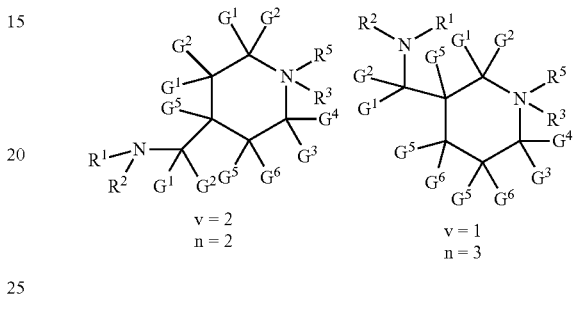

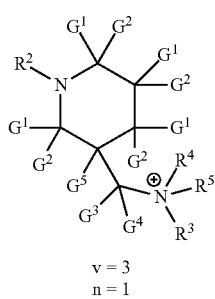
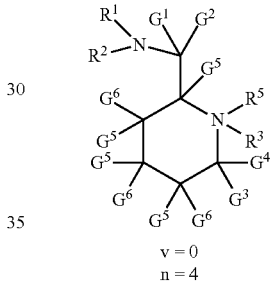

As is clear from these particular structural formulae above, in these embodiments, the tertiary nitrogen atom is in the ring, and the quaternary nitrogen is on a side chain attached to the ring.

Exemplary buffer compounds in accordance with the foregoing embodiments when one of one of $R^3$ and $G^5$, $R^3$ and $G^6$, $R^4$ and $G^5$, $R^4$ and $G^6$, $R^5$ and $G^5$, and/or $R^5$ and $G^6$, are taken as a pair and form a chemical moiety such that the pair is a $—(CG^1G^2)_z$- group, include the following:

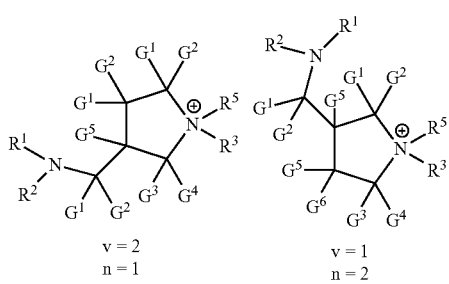

In all of the foregoing embodiments of the pairs of $R^1$ and $G^5$, $R^1$ and $G^6$, $R^2$ and $G^5$, $R^2$ and $G^6$, $R^3$ and $G^5$, $R^3$ and $G^6$, $R^4$ and $G^5$, $R^4$ and $G^6$, $R^5$ and $G^5$, and/or $R^5$ and $G^6$, the remainder of the amine-quaternary ammonium compound may be as described elsewhere herein, i.e., the unpaired $R^1$, $R^2$, $R^3$, $R^4$ and $R^5$ and the $G^1$, $G^2$, $G^3$, $G^4$, $G^5$ and $G^6$ groups, and other variables, may be suitably selected as defined herein.

Cyclic Group (g):

In the buffer compounds in accordance with the present invention, in some embodiments, one or more pair of $R^1$ and $G^1$, $R^1$ and $G^2$, $R^2$ and $G^1$, $R^2$ and $G^2$, $R^3$ and $G^3$, $R^3$ and $G^4$, $R^4$ and $G^3$, $R^4$ and $G^4$, $R^5$ and $G^3$, and/or $R^5$ and $G^4$ forms a single chemical moiety such that the pair is individually and independently $—(CG^1G^2)_u$- with u having integer values 3-4 and n having integer values 0-4.

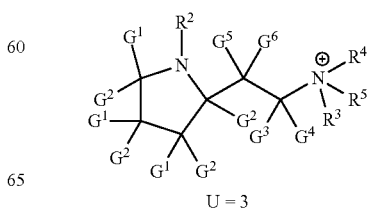

-continued

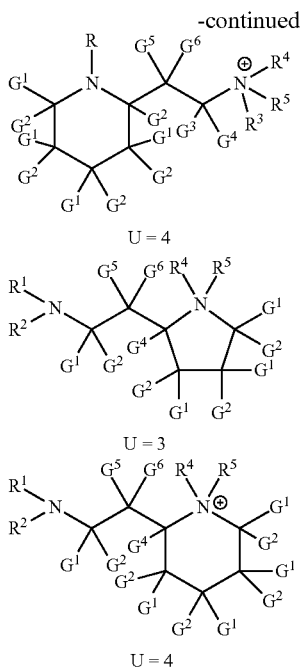

In all of the foregoing embodiments of the pairs of $R^1$ and $G^1$, $R^1$ and $G^2$, $R^2$ and $G^1$, $R^2$ and $G^2$, $R^3$ and $G^3$, $R^3$ and $G^4$, $R^4$ and $G^3$, $R^4$ and $G^4$, $R^5$ and $G^3$, and/or $R^5$ and $G^4$, the remainder of the amine-quaternary ammonium compound may be as described elsewhere herein, i.e., the unpaired $R^1$, $R^2$, $R^3$, $R^4$ and $R^5$ and the $G^1$, $G^2$, $G^3$, $G^4$, $G^5$ and $G^6$ groups, and other variables, may be suitably selected as defined herein.

The amine-quaternary ammonium compound, by definition, includes a positive charge on the quaternary nitrogen atom. This positive charge must be balanced by a negatively charged chemical moiety to obtain electroneutrality for the compound as a whole. As used herein, the term "electroneutrality" refers to the art-recognized principle that a chemical compound must have a net charge of zero, and a compound that has such net zero charge is electroneutral. Thus, the amine-quaternary ammonium compound as a whole must have electroneutrality. To obtain such electroneutrality, whatever net charge is on the amine-quaternary ammonium portion of the overall compound must either be a zero net charge, e.g., be internally electroneutral like a zwitterion, or be associated with a group herein designated "CI" ("Counter-Ion") to balance the non-zero net charge on the amine-quaternary ammonium portion of the overall compound. As will be understood, since the amine-quaternary ammonium portion may have a net positive or a net negative charge, depending on the number and type of charged substituents present, i.e., the protonation or non-protonation of the amine nitrogen atom, the number of anionic substituent groups, and whether these anionic substituent groups are protonated at the pK of the amine-quaternary ammonium compound.

Accordingly, in accordance with the present invention, CI is a non-interfering counter-ion or mixture of counter-ions as needed to maintain electroneutrality of the overall amine-quaternary ammonium compound. The overall net charge on the amine-quaternary ammonium compound is equal to the value of a quantity (j+k−z+1), in which z equals the absolute value of the numerical sum of all negative charges on each carboxylate, sulfonate and phosphonate moiety contained within $R^1$, $R^2$, $R^3$, $R^4$, $R^5$, $R^6$, $R^7$, $G^2$, $G^4$, $G^6$, $G^8$, $G^9$, and j and k are 0 for the un-protonated compound, and j and k are 1 for the fully protonated compound, as defined above.

The number of CI groups, is designated "d" in the general formula above. In accordance with the present invention, d equals |j+k−z+1| (i.e., the absolute value of the quantity (j+k−z+1) for monovalent counter-ions, |j+k−z+1|/2 for divalent counter-ions, |j+k−z+1|/3 for trivalent counter-ions, |j+k−z+1|/4 for tetravalent counter-ions. The sign (i.e., + or −) of the quantity (z−j−k−1) reflects the charge on the counter-ion, meaning that when (z−j−k−1) is negative or minus (−), CI is an anion, and when (z−j−k−1) is positive or plus (+), CI is a cation and when (z−j−k−1) is zero, then d is zero and there is no counter-ion (CI).

In one embodiment, CI is a non-interfering anion or a mixture of non-interfering anions selected from $Cl^-$, $Br^-$, $I^-$, $OH^-$, $F^-$, $OCH_3^-$, $HCO_2^-$, $CH_3CO_2^-$, $CF_3CO_2^-$, $NO_3^-$, $ClO_4^-$, $BF_4^-$, $PF_6^-$, $HSO_4^-$, $HCO_3^-$, $H_2PO_4^-$, $CH_3OCO_2^-$, $CH_3OSO_3^-$, $CH_3SO_3^-$, $CF_3SO_3^-$, $H_2PO_3^-$, $CH_3PO_3H^-$, $HPO_3^{2-}$, $CH_3PO_3^{2-}$, $CO_3^{2-}$, $SO_4^{2-}$, $HPO_4^{2-}$ and $PO_4^{3-}$.

In one embodiment, CI is a non-interfering cation or a mixture of non-interfering cations selected from: $Li^+$, $Na^+$, $K^+$, $Rb^+$, $Cs^+$, $NH_4^+$, $Ag^+$, $Tl^+$, $Mg^{2+}$, $Ca^{2+}$, $Sr^{2+}$, $Ba^{2+}$, $VO^{2+}$, $Mn^{2+}$, $Fe^{2+}$, $Co^{2+}$, $Ni^{2+}$, $Cu^{2+}$, $Zn^{2+}$, $Cd^{2+}$, $Hg^{2+}$, $Eu^{2+}$, $UO_2^{2+}$, $Pb^{2+}$, $Al^{3+}$, $Ga^{3+}$, $Sc^{3+}$, $Y^{3+}$, $BiO^+$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$ and $Th^{4+}$.

In one embodiment, CI is a non-interfering cation or a mixture of non-interfering cations selected from: a protonated primary alkyl or hydroxyalkyl amine, a protonated secondary alkyl or hydroxyalkyl amine, a protonated tertiary alkyl or hydroxyalkyl amine, a diprotonated alkyl, alkylene, hydroxyalkyl or hydroxyalkylene diamine, a quaternary alkyl or hydroxyalkyl ammonium compound, an alkyl or hydroxyalkyl sulfonium compound, an alkyl or hydroxyalkyl sulfoxonium compound, a quaternary alkyl or hydroxyalkyl phosphonium compound and a di-quaternary alkyl, alkylene, hydroxyalkyl or hydroxyalkylene ammonium compound, wherein the foregoing alkyl, alkylene, hydroxyalkyl and hydroxyalkylene groups contain one to three carbon atoms, and wherein the cation or the mixture of cations is not an amine-quaternary ammonium buffer compound as defined herein.

In one embodiment, CI is a non-interfering buffering anion, a mixture of non-interfering buffering anions, a non-interfering buffering cation or a mixture of non-interfering buffering cations, with $pK_a$ value(s) in the range 1-13, and in which CI is not an amine-quaternary ammonium buffer compound as defined herein.

In one embodiment, CI is a non-interfering buffering anion, a mixture of non-interfering buffering anions, a non-interfering buffering cation or a mixture of non-interfering buffering cations, with $pK_a$ value(s) in the range 1-13, and wherein CI is an amine-quaternary ammonium compound as defined herein, and has a charge conferring electroneutrality on the overall buffer compound.

It should be readily apparent to the skilled person that the amine-quaternary ammonium compound disclosed herein is capable of forming a number of different isomers with the same atom connectivity. Therefore, the present disclosure encompasses each diastereomeric isomer, each cis/trans isomer and each enantiomeric isomer that may be formed by the various substituents disclosed herein.

As noted, in one embodiment, the present invention relates to a method of buffering a chemical or biological composition, including adding to the composition an effective buffering amount of at least one of the above-defined amine-quaternary ammonium compounds, in which the amine nitrogen atom may be protonated or un-protonated. The above-defined amine-quaternary ammonium compounds are soluble in water and in aqueous systems, such as biological compositions, and in chemical compositions that are aqueous (water-based) or non-aqueous (polar organic solvent). In using the buffer compound compositions disclosed herein, the compound may be used substantially the same manner as any other buffer compound, as known and understood in the art.

Temperature Dependence of $pK_a$:

Because buffer compounds are often used at different temperatures, typically in the range 5-45° C., it is desirable to have a buffer whose $pK_a$ change with temperature is small so that the shift in pH is small as the temperature changes. Based on analogous systems it is expected that the buffers described here will become slightly more acidic (lower $pK_a$) at higher temperatures with $\Delta H$ of dissociation in the range of +2.5 to +6.0 Kcal/mole. This corresponds to a decrease of 0.09 to 0.22 log $K_a$ units per 15 degree increase in temperature (20° C. to 35° C.).

Statistical Effects:

In designing buffer compounds, statistical effects must be accounted for in addition to the usual issues of (a) intrinsic proton affinity and (b) selective solvation effects. This is illustrated for a series of protonated polyamine compounds below. Note that for a given molecule, the ammonium $pK_a$ values (a) are essentially the same because the acidic sites are chemically identical or related by symmetry, and (b) the amine groups are essentially isolated from each other (interaction <0.2 log $K_a$ units) because they are separated by seven carbon atoms. However, these statistical effects are still operative (a) when multiple ammonium sites are chemically different yet "accidentally" the same (very close $pK_a$ values) and (b) when the ammonium sites are spatially closer and hence may be "chemically coupled".

$K^1_a$: $CH_3CH_2CH_2CH_2NHMe_2^+ \rightarrow H^+ + CH_3CH_2CH_2CH_2NMe_2$ $K^2_{a1}$: $CH_2(CH_2CH_2CH_2NHMe_2)_2^{2+} \rightarrow H^+ + Me_2NCH_2CH_2CH_2CH_2CH_2CH_2NHMe_2^{1+}$ $K^2_{a2}$: $Me_2NCH_2CH_2CH_2CH_2CH_2CH_2NHMe_2^{1+} \rightarrow H^+ + CH_2(CH_2CH_2CH_2NMe_2)_2$ $K^3_{a1}$: $CH(CH_2CH_2CH_2NHMe_2)_3^{3+} \rightarrow H^+ + Me_2NCH_2CH_2CH(CH_2CH_2CH_2NHMe_2)_2^{2+}$ $K^3_{a2}$: $Me_2NCH_2CH_2CH_2CH(CH_2CH_2CH_2NHMe_2)_2^{2+} \rightarrow H^+ + (Me_2NCH_2CH_2CH_2)_2CHCH_2CH_2CH_2NHMe_2^{1+}$ $K^3_{a3}$: $Me_2NCH_2CH_2CH_2)_2CHCH_2CH_2CH_2NHMe_2^{1+} \rightarrow H^+ + CH(CH_2CH_2CH_2NMe_2)_3$ $K^4_{a1}$: $C(CH_2CH_2CH_2NHMe_2)_4^{4+} \rightarrow H^+ + Me_2NCH_2CH_2CH_2C(CH_2CH_2CH_2NHMe_2)_3^{3+}$ $K^4_{a2}$: $Me_2NCH_2CH_2CH_2C(CH_2CH_2CH_2NHMe_2)_3^{3+} \rightarrow H^+ + (Me_2NCH_2CH_2CH_2)_2C(CH_2CH_2CH_2NHMe_2)_2^{2+}$ $K^4_{a3}$: $(Me_2NCH_2CH_2CH_2)_2C(CH_2CH_2CH_2NHMe_2)_2^{2+} \rightarrow H^+ + (Me_2NCH_2CH_2CH_2)_3CCH_2CH_2CH_2NHMe_2^{1+}$ $K^4_{a4}$: $(Me_2NCH_2CH_2CH_2)_3CCH_2CH_2CH_2NHMe_2^{1+} \rightarrow H^+ + C(CH_2CH_2CH_2NMe_2)_4$ $pK^1_a = -\log K - \log [1/1] = pK_a$ $pK^2_{a1} = -\log K - \log [2/1] = pK_a - 0.30$ $pK^2_{a2} = -\log K - \log [1/2] = pK_a + 0.30$ $pK^3_{a1} = -\log K - \log [3/1] = pK_a - 0.48$ $pK^3_{a2} = -\log K - \log [2/2] = pK_a$ $pK^3_{a3} = -\log K - \log [1/3] = pK_a + 0.48$ $pK^4_{a1} = -\log K - \log [4/1] = pK_a - 0.60$ $pK^4_{a2} = -\log K - \log [3/2] = pK_a - 0.18$ $pK^4_{a3} = -\log K - \log [2/3] = pK_a + 0.18$ $pK^4_{a4} = -\log K - \log [1/4] = pK_a + 0.60$ In the examples given above, "K" is the acid dissociation constant for the prototypical alkyl dimethylammonium ion. Thus, in addition to other factors, statistical effects alone cause the measured $pK_a$ values to move apart for polyprotic polyammonium ions by 0.5-1 log $K_a$ units or more. In the case of the di-ammonium ions, the two $pK_a$ values will be about 0.6 log $K_a$ units apart, and the two values will move farther apart as the two ammonium groups begin to interact when they are spatially closer to each other. For di-ammonium ions, the statistical factors are maximized when the two intrinsic proton affinities are exactly the same. In this case, as the intrinsic proton affinities move apart, the statistical effects are reduced, and when the two intrinsic proton affinities differ by 2 log $K_a$ units or more, statistical effects can be ignored.

Buffer Design Principles For the Invention

The main concepts in the design of amine-quaternary ammonium pH buffer compounds are described below. The presence of a quaternary ammonium (quat) group in a molecule that also contains an amine group will reduce the $pK_a$ of the amine as measured in aqueous media and polar nonaqueous media. The causes and magnitudes of the changes are not fully understood, but the end results are predictable and useful in buffer design regardless of other theoretical considerations. The operative effects are thought to be (1) through-space electrostatic effects of the positive charge, (2) through-bond electron-withdrawing effects of the quat group and (3) a change in solvation of the free amine relative to the protonated amine. All three effects as described will generally lead to some reduction of observed $pK_a$ in the molecule of interest. Trimethylamine ($pK_a$=9.8) and pentamethylguanidine ($pK_a$=13.8) are used here as prototypical amines. The amount of reduction in $pK_a$ depends on (1) the number of quat groups, (2) the distance of the quat group(s) from the amine and (3) the rigidity of the molecule that holds the quat group and amine in more fixed position with regard to each other. The application of these principles are illustrated below for methyl amines. The given approximate numbers primarily apply to derivatives of trimethylamine in water at 25° C. at modest ionic-strength ($\mu$=0.1).

| $Me_2N-(CH_2)_n-NMe_3^+$ | Change in $pK_a$ of $Me_2N-$ (log K units) |
|---|---|
| n = 6 ($-CH_2(CH_2)_4CH_2-$) | ~−0.3 |
| n = 5 ($-CH_2(CH_2)_3CH_2-$) | ~−0.5 |
| n = 4 ($-CH_2(CH_2)_2CH_2-$) | ~−0.9 |
| n = 4 ($-CH_2CH(OH)CH(OH)CH_2-$) | ~−1.1 |
| n = 4 (trans $-CH_2CH=CHCH_2-$) | ~−1.3 |
| n = 3 ($-CH_2CH_2CH_2-$) | ~−1.7 |
| n = 3 ($-CH_2CH(OH)CH_2-$) | ~−1.9 |

| $Me_2N$—$(CH_2)_n$—$NMe_3^+$ | Change in $pK_a$ of $Me_2N$— (log K units) |
|---|---|
| n = 2 (—$CH_2CH_2$—) | ~−3.7 |
| n = 1* (—$CH_2$—) | ~−10.5 |
| | Limited hydrolytic stability |
| N,N',N'-$Me_3$-Homopiperazinium$^+$ | ~−3.6 |
| N,N',N'-$Me_3$-Piperazinium$^+$ | ~−5.5 |
| N-Me-Diazabicyclo[2.2.2]octane$^+$ | ~−6.7 |

The similar trends apply to penta-substituted guanidines, but the magnitude of the effects of a single proximal quat group on the imino-nitrogen is not as large. Although not to be bound by theory, these empirical observations are thought to result from electron distribution and resulting charge distribution over the entire $N_3C$ guanidino core in the free and protonated guanidine. Thus, a single ammoniumalkyl ($Me_3N^+(CH_2)_n$—, n=2-4) substitution on the imino-nitrogen changes the $pK_a$ values by approximately −1.9 (n=2), −0.9 (n=3) and −0.5 (n=4) log K units. Similarly, a single ammoniumalkyl substitution on the distal amino-nitrogen of a guanidine causes smaller changes in the $pK_a$ values by approximately −0.9 (n=2), −0.4 (n=3) and −0.2 (n=4) log K units. Further modulation of the $pK_a$ values of guanidines can occur by enhancing or reducing the planarity of the $C_5N_3C$ core through the use of bulky substituents or cyclic structures. The use of a five-membered, non-planar ring in 2-imino-1,3-dimethylimidazoline can cause a reduction in the $pK_a$ of the resulting guanidine. The $pK_a$ of a guanidino group can be adjusted by adding one or more ammoniumalkyl groups to a single penta-substituted guanidine either on the imino-nitrogen or on one or both amino-nitrogens. Furthermore, zwitterionic ammoniumalkyl groups ($^-X(CH_2)_kMe_2^+(CH_2)_n$—, n=2-4, k=1-3, —X=$^-O_2C$, $^-O_3S$) have effects on $pK_a$ similar to corresponding non-zwitterionic ammoniumalkyl groups yet prevent the buildup of overall charge on the molecule. In one embodiment, one may construct penta-substituted guanidines with cyclic structures which also contain quaternary ammonium groups which in turn modulate the $pK_a$ of the molecule.

Only small ring systems (6/7-membered ring) are shown in the table above. Note that the cyclic piperazine derivative (−5.5) has a much reduced $pK_a$ compared to the non-cyclic ethylenediamine derivative (−3.7), yet the cyclic homopiperazine derivative (−3.6) is not much different from the ethylenediamine derivative. Some monocyclic structures lead reduced $pK_a$ while others do not. Large and small ring sizes can be used with varying results.

Once a monoquaternized diamine or triamine structure is chosen with a $pK_a$ near the desired range, then the $pK_a$ can be further modulated by replacing one or more methyl groups on the amine nitrogen or guanidine imino-nitrogen with neutral or anionic substituents (see below). Furthermore, two methyl groups on the same amine nitrogen can be replaced with a single bifunctional group to form a cyclic structure as described above. When the groups shown below are attached to the quaternary-nitrogen rather than the amine-nitrogen, they have little if any affect on the $pK_a$ of the amine(s), and to a first approximation, their effect on the $pK_a$ value of the amine-nitrogen can be largely ignored.

| Neutral Group (R) | Change in $pK_a$ when methyl is replaced by R on N (log K units) |
|---|---|
| —H (1 only) | ~+1.0 |
| —$C_6H_{11}$(cyclohexyl, 1 only) | ~+0.9 |
| —$CH(CH_3)_2$ (1 only) | ~+0.7 |
| —$CH_2CH_3$ | ~+0.3 |
| —$CH_2CH_2CH_2OH$ | ~−0.3 |
| —$CH_2CH_2CH_2N(CH_3)_2$ | ~−0.3 (extra amine) |
| —$CH_2CH_2CH_2C(=O)NH(CH_3)$ | ~−0.4 |
| —$CH_2CH_2CH_2NHC(O)CH_3$ | ~−0.5 |
| —$CH_2CH=CH_2$ | ~−0.5 |
| —$CH_2CH_2OH$ | ~−0.6 (~−0.9*) |
| —$CH_2CH_2OCH_3$ | ~−0.7 (~−1.0*) |
| —$CH_2C_6H_5$ | ~−0.9 |
| —$CH_2CH_2N(CH_3)_2$ | ~−0.9 (extra amine) |
| —$CH_2CH_2C(=O)NH(CH_3)$ | ~−1.2 |
| —$CH_2CH_2NHC(O)CH_3$ | ~−1.4 |
| —$CH_2C(=O)N(CH_3)_2$ | ~−2.3 |
| —$CH_2CH_2CH_2$— | ~+0.8 (pyrrolidine) |
| —$CH_2CH_2CH_2CH_2$— | ~+0.4 (piperidine) |
| —$CH_2CH_2CH(OH)CH_2CH_2$— | ~+0.1 (4-hydroxy-piperidine) |
| —$CH_2CH(OH)CH(OH)CH_2$— (trans) | ~−0.6 (t-2,3-dihydroxypyrrolidine) |
| —$CH_2CH_2N(CH_3)CH_2CH_2$— | ~−1.9 (N-methyl-piperazine; extra amine) |
| —$CH_2CH_2OCH_2CH_2$— | ~−2.3 (morpholine) |
| —$CH_2CH_2N((C(O)CH_3))CH_2CH_2$— | ~−2.9 (N-acetyl-piperazine) |
| —$CH_2C(=O)NHCH_2CH2$— | ~−3.5 (2-oxopiperazine) |

*The larger value seems to be more applicable for quat-amine compounds.

A much wider range of functionalized amine-quaternary ammonium compounds can be attained by adding chemical groups that contain charges. Resulting neutral (1$^+$/0) or anionic (0/1$^-$), zwitterionic or di-zwitterionic buffer compounds are produced by attaching one or more uninegative anionic chemical groups at strategic locations. Like the groups above, when attached to the quaternary-nitrogen atom, the anionic chemical groups have little, if any, effect on the $pK_a$ of the neighboring amine-nitrogen atom. However, when attached to the amine-nitrogen itself, the anionic groups can act to reduce or increase the $pK_a$ (see below). Groups with an alkyl chain coupled with the negative charge tend to increase $pK_a$ while electron-withdrawing characteristics of the sulfonate-, carboxylate- and phosphonate-groups tend to reduce the $pK_a$. The electron-withdrawing nature of the anionic groups follow the expected order:

Sulfonate>Carboxylate>Phosphonate

Aliphatic sulfonate groups have very low $pK_a$ values (−1.5 to −2.5) and are always fully deprotonated. Similarly, the first $pK_a$ values of aliphatic phosphonates are also low (0.4-2.3, $pK_{a1}$) and are often deprotonated. Aliphatic carboxylates occur in the $pK_a$ range ~2.0 to ~4.6; while the second deprotonations of aliphatic phosphonates fall in the range ~5.2 to ~7.7 ($pK_{a2}$). The table below gives the change in the $pK_a$ of an amine when an attached methyl group is replaced by the designated anionic group. These approximate values are only valid when the anionic groups are fully deprotonated (amine $pK_a$>anionic group $pK_a$). Approximate $pK_a$ values of the anionic groups themselves are given in parentheses.

| Anionic Group | Change in $pK_a$ (log K units) |
|---|---|
| —$CH_2SO_3$— | −2.6 (<−1.0) Limited hydrolytic stability |
| —$CH_2CH_2SO_3$— | −1.5 (<−1.0) |
| —$CH_2CH_2CH_2SO_3^-$ | −0.6 (<−1.0) |
| —$CH_2CH(OH)CH_2SO_3^-$ | −0.8 (<−1.0) |

-continued

| Anionic Group | Change in pK$_a$ (log K units) |
|---|---|
| —CH$_2$CH$_2$CH$_2$CH$_2$SO$_3^-$ | +0.1 (<−1.0) |
| —CH$_2$CO$_2^-$ | 0.0 (~2.0) |
| —CH$_2$CH$_2$CO$_2^-$ | +0.1 (~3.3) |
| —CH$_2$CH$_2$CH$_2$CO$_2^-$ | +0.2 (~3.9) |
| —CH$_2$CH(OH)CH$_2$CO$_2^-$ | −0.1 (~3.8) |
| —CH$_2$CH$_2$CH$_2$CH$_2$CO$_2^-$ | +0.3 (~4.2) |
| —CH$_2$PO$_3^{2-}$ | +1.1 (~0.4, ~5.2) |
| —CH$_2$CH$_2$PO$_3^{2-}$ | +1.2 (~1.1, ~6.2) |
| —CH$_2$CH$_2$CH$_2$PO$_3^{2-}$ | +1.3 (~1.6, ~6.9) |
| —CH$_2$CH$_2$CH$_2$CH$_2$PO$_3^{2-}$ | +0.9 (~1.9, ~7.3) |

The concept of "group additivity" for estimating pK$_a$ values should be applied only to a narrow class of related compounds. The factors given here are illustrative in that they are unique to this application, are approximate, apply primarily to the simple tertiary amines, and factors themselves are not truly additive.

To illustrate inaccuracies in the group additivity concept, the table below is provided to show variations in the change in pK$_a$ factor for replacing a methyl (—CH$_3$) group with a 2-hydroxyethyl (—CH$_2$CH$_2$OH) group in different amines of the type, RNMe$_2$, for amines containing various R groups. Though a value of −0.6 is sometimes used for —CH$_2$CH$_2$OH, for amine-quat compounds a value of −0.9 seems to be more suitable.

Change in pK$_a$ for replacement of R in RN(CH$_3$)$_2$ compared to RN(CH$_3$)CH$_2$CH$_2$OH:

| R | Factor |
|---|---|
| —CH$_3$ | −0.6 |
| —CH$_2$CH$_3$ | −0.6 |
| —CH$_2$PO$_3$H$_2$ | −0.6 |
| —CH$_2$CH$_2$OH | −0.7 |
| —CH$_2$CH$_2$SO$_3$H | −0.7 |
| —CH$_2$CO$_2$H | −0.85 |
| —H | −0.9 |
| —CH$_2$CH(OH)CH$_2$NMe$_3^+$ | −0.9 |

Despite the inaccuracies, this "rule-based" system can be very useful in targeting a select group of buffer molecules of the amine-quaternary ammonium type within a desired pK$_a$ range.

Illustration of Buffer Design in Accordance With the Invention:

The design process is illustrated below for creating an anionic amine-quat buffer compound (0/1⁻) with an approximate pK$_a$ value in the range of 5.1-5.9. For buffers containing carboxylate and phosphonate residues, their estimated pK$_a$ values are also included. Note that some of the estimated pK$_a$ values are shifted somewhat owing to statistical effects when intrinsic pK$_a$ values are close. Note also that some of these putative compounds have potential, long-range buffering capacity owing to closely spaced multiple pK$_a$ values. One starts with the pK$_a$ of trimethylamine (9.8), and then appropriate change in pK$_a$ factors based on the foregoing tables of change in pK$_a$ for various groups are added or subtracted.

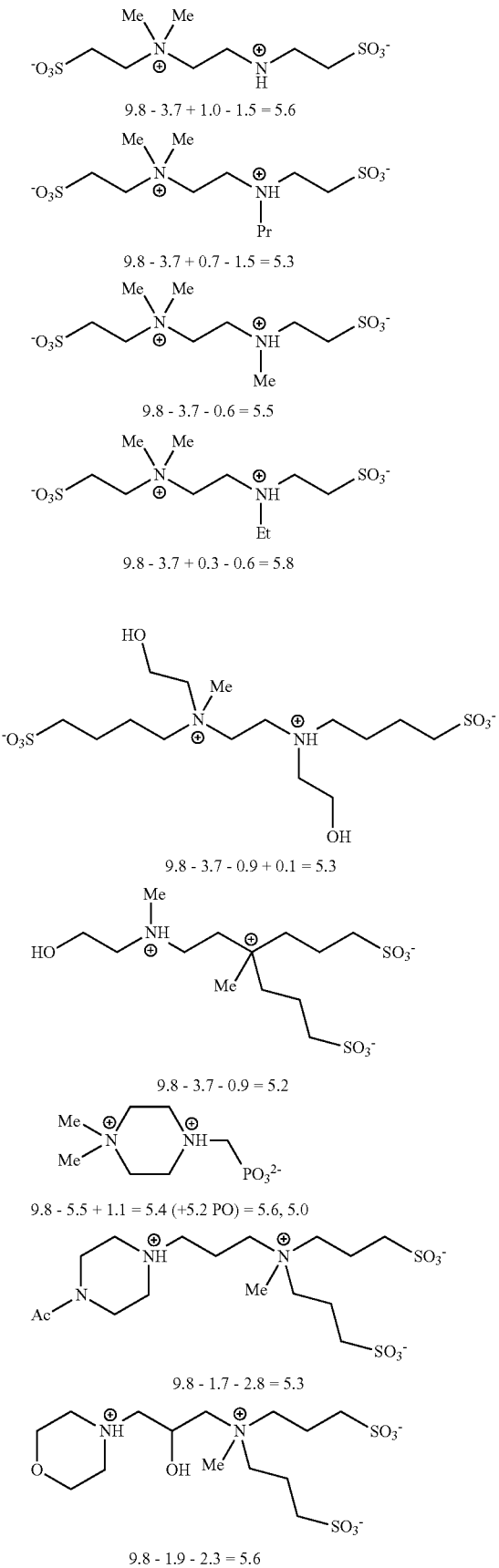

-continued

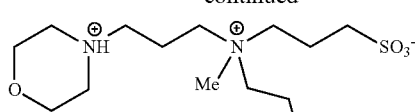

9.8 - 1.7 - 2.3 = 5.8

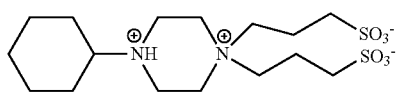

9.8 - 5.5 + 0.9 = 5.2

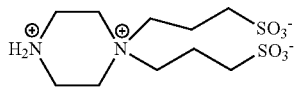

9.8 - 5.5 + 1.0 = 5.3

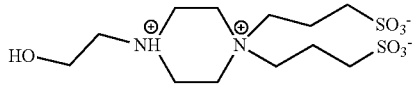

9.8 - 3.6 - 0.9 = 5.3

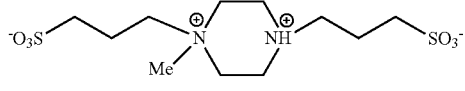

9.8 - 3.6 - 0.6 = 5.6

Cyclic Amine-Quaternary Buffers:

From the basic linear structure, many monocyclic and multicyclic structures can be created. Some are easy to synthesize; others are not. Some are more expensive to make; others are less expensive. Some are easily purified; others are not. Some have unique buffering properties; others are redundant. Some have flexible structures; others are more rigid. By way of illustration five multi-cyclic structures are shown below. "G-groups" that are not designated contain —$CH_2$— entities. For each of the following structures, two side-by-side alternate depictions of the same molecule are shown.

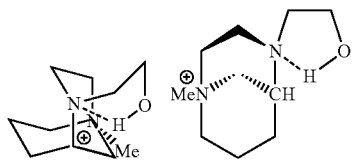

$R^3/Y^1 =$ ——$(CY^1Y^2)_s$——, s = 3
$R^1/R^4 =$ ——$(CY^1Y^2)_g$——, g = 2
n = 0, $R^2 =$ ——$CH_2CH_2OH$, $R^5 =$ Me

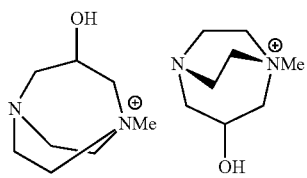

$R^1/R^3 =$ ——$(CY^1Y^2)g$——, g = 2
$R^2/R^4 =$ ——$(CY^1Y^2)g$——, g = 2
n = 1, $R^5 =$ Me, $Y^6 =$ OH

-continued

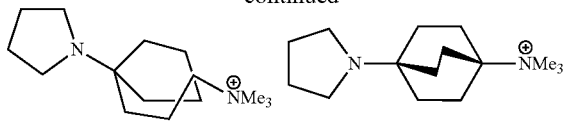

$Y^1/Y^3 =$ ——$(CY^1Y^6)_q$——, q = 2
$Y^2/Y^4 =$ ——$(CY^1Y^6)_q$——, q = 2
n = 2, $R^1/R^2 =$ ——$CH_2CH_2CH_2CH_2$——
$R^3 = R^4 = R^5 =$ Me

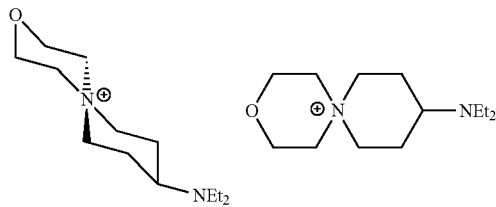

$R^3/Y^1 =$ ——$(CY^1Y^2)_s$——, s = 2
$R^4/R^5 =$ ——$CH_2CH_2OCH_2CH_2$——
n = 1, $Y^5 = Y^6 =$ Me, $R^5 =$ ——$CH_2CO_2^-$
n = 1, $R^1 = R^2 =$ Et

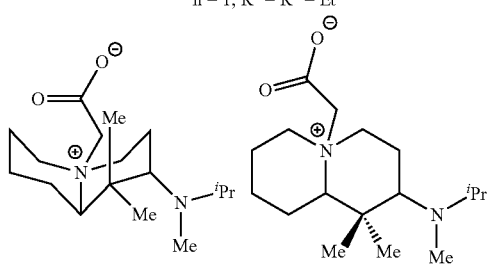

$R^3/Y^1 =$ ——$(CY^1Y^2)_s$——, s = 3
$R^4/Y^3 =$ ——$(CY^1Y^2)_u$——, u = 4
n = 1, $Y^5 = Y^6 =$ Me, $R^5 =$ ——$CH_2CO_2^-$
$R^1 =$ Me, $R^2 = ^iPr$

Wide-Range Buffer Compounds.

The amine-quaternary ammonium compounds described here can be designed with two or more acidic sites with properly-spaced, multiple $pK_a$ values. Overlapping buffering ranges allow for the construction of wide-range (about 2 to about 3 log K units) buffering compounds with variable charge properties. Using the principles described above, buffer molecules can be designed with carboxylate groups or phosphonate groups ($pK_{a2}$) or with a second amine group ($R^5$) so that multiple $pK_a$ values are approximately 1-2 log K units apart. Estimates of buffering ranges are made by subtracting 0.5 from the lower $pK_a$ and adding 0.5 to the higher $pK_a$. The following chemical structures illustrate amine-quat compounds that have useful wide-range buffering properties. Note that the monoquaternizing the central nitrogen of triamine compounds leads to wide-range buffers with few of the undesirable properties of ordinary polyamines.

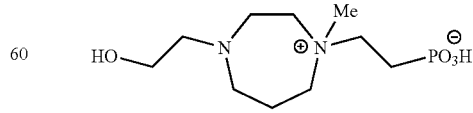

pKa = 5.2, 6.3
range = 4.7-6.8
$1^+/0/1^-$

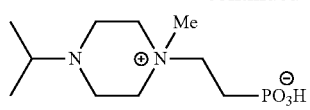

pKa = 4.9, 6.3
range = 4.4-6.8
1⁺/0/1⁻

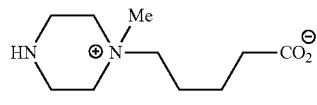

pKa = 4.1, 5.4
range = 3.6-5.9
2⁺/1⁺/0

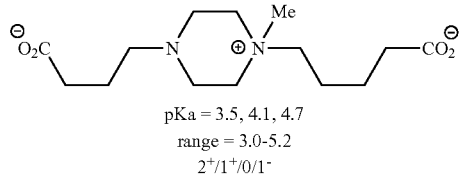

pKa = 3.5, 4.1, 4.7
range = 3.0-5.2
2⁺/1⁺/0/1⁻

Additional structures are shown below.

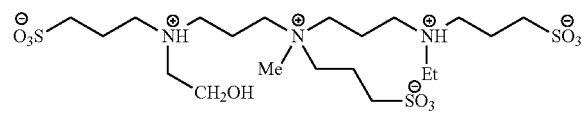

pKa = 6.5, 7.9
range = 6.0-8.4
0/1⁻/2⁻

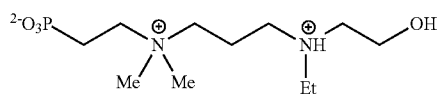

pKa = 6.1, 7.6
range = 5.6-8.1
1⁺/0/1⁻

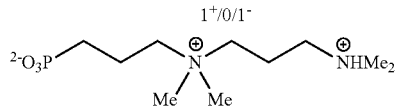

pKa = 6.8, 8.2
range = 6.3-8.7
1⁺/0/1⁻

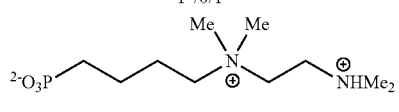

pKa = 6.0, 7.4
range = 5.5-7.9
1⁺/0/1⁻

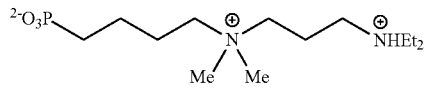

pKa = 7.2, 8.8
range = 6.8-9.3
1⁺/0/1⁻

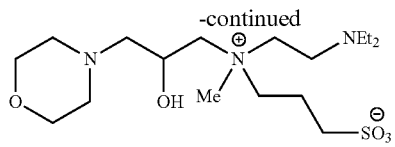

pKa = 5.5, 6.8
range = 5.0-7.3
2⁺/1⁺/0

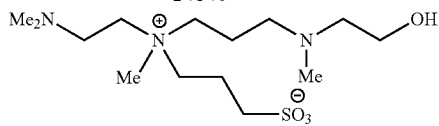

pKa = 6.0, 7.3
range = 5.5-7.8
2⁺/1⁺/0

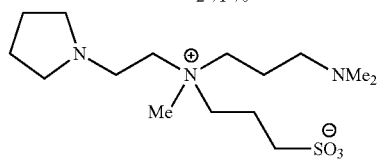

pKa = 6.8, 8.2
range = 6.3-8.7
2⁺/1⁺/0

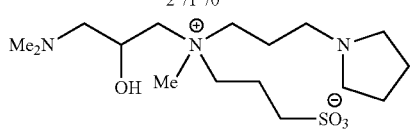

pKa = 7.8, 9.0
range = 7.3-9.5
2⁺/1⁺/0

Synthesis of Amine-Quat Buffers:

Owing to their unsymmetric structures, amine-quat compounds require special care in preparation. Nonetheless, known synthetic methods, when properly applied, can lead to the production of amine-quat compounds in reasonable yield and purity.

Monoalkylation of Symmetric Diamines:

As will be understood by those of skill in the art, the challenge with monoalkylation is to get the reaction to proceed, yet prevent dialkylation. Some experimentation may be necessary to optimize conditions for a given reaction. A solvent is chosen in which the starting materials are soluble, but in which the monoalkylated salt or zwitterion is insoluble. Slow addition of the alkylating agent to an excess of the stirring diamine, for example, starting at 1:10, or perhaps 1:3 and moving toward a 1:1.1 molar ratio will reduce the possibility of dialkylation. This addition process is particularly important when using reactive gasses. If the second alkylation reaction is sufficiently slow or inhibited, sometimes nearly 1:1 molar ratios can be used. Reasonable, not rapid, reaction times and minimal reaction temperature are chosen so that there is minimal exotherm; higher temperatures generally promote dialkylation. Proper screening of solvents can give reasonable reaction rates and reduced dialkylation. For example, solvents such as diethyl ether and/or acetone promote monoalkylation because the monoalkylated product usually precipitates from these and similar solvents. In many cases, monoalkylation inhibits dialkylation to varying degrees. For example, dimethylation of N,N,N',N'-tetramethyl-1,2-ethanediamine is strongly inhibited while dimethylation of N,N,N',N'-tetramethyl-1,6-hexanediamine is only moderately inhibited. In general, the closer together the nitrogen atoms are in the target diamine, the easier it is to obtain monoalkylation. Specific applications of these general guidelines are provided in the synthesis examples provided below. See, e.g., Example 5b.

Monoalkylation of Unsymmetric Diamines:

Unsymmetric di-tertiary diamines present an additional problem because there are two possible monoalkylated isomers. In some cases, clean monoalkylation can be carried out producing a single isomer and little dialkylation when one of the tertiary amines is sterically hindered. Regioselective alkylation of a dimethylamino- group is sufficiently faster than diethylamino- or methylcyclohexylamino- groups that clean monoalkylation can take place.

Protection/Deprotection of Unsymmetric Diamines:

Protection and deprotection of unsymmetric amine intermediates and products is a well established synthetic methodology. However, it is generally avoided because it introduces two additional synthetic steps. However, the synthesis and crystallization of benzyl quaternary ammonium compounds are so convenient, and the removal of the protecting benzyl group by catalytic hydrogenation is so efficient and convenient that this reaction sequence can be useful.

Assembly of Amine-Quat from a Quat Compound and an Amine:

Occasionally, reactive amino-quat compounds or alkylating-quat compounds are easily synthesized or purchased. In this case, the parts of the amine-quat are independently prepared and then put together forming an unsymmetric amine-quat compound.

Selective Crystallization:

The solubilities of organic dications and related organic monocations in organic solvents can be quite different. Screening of organic solvents can lead to a recrystallization medium wherein the dication crystallizes from solution while the monocation remains in solution or vice versa. This is particularly useful for zwitterionic compounds in solvents such as methanol, absolute ethanol, isopropanol or sometimes acetone and acetonitrile. The pH is adjusted (acidic, neutral, basic) so that the desired product is in its overall neutral form; this reduces solubility in organic solvents and leads to crystallization from solution while charged species (impurities) will remain in solution. This process can be a convenient way to separate the neutral monoalkylated product from the soluble charged starting materials and dialkylated product. Similarly, the pH can be readjusted to solubilize the desired product but not undesired byproducts that are then removed by filtration.

Another useful recrystallization method is to suspend the desired product in stirring, hot absolute ethanol or ethanol/isopropanol mixtures. Small amounts of distilled water are slowly added until the amine-quat compound barely dissolves in the hot solvent mixture which may be filtered and then allowed to slowly cool to room temperature and then to 4° C. Nice crystals of the purified monoquaternary product often result.

EXAMPLE 1

Preparation of 2-(3-trimethylammoniumpropyl)-1,1,3,3-tetramethylguanidine bromide hydrobromide (76, fw=376.19)

26.61 g (3-bromopropyl)trimethylammonium bromide (100 mmole, fw=261.01) is suspended in 200 mL stirring acetonitrile (magnetic stirring) in a 500 mL Erlenmeyer flask. 34.56 g freshly distilled 1,1,3,3-tetramethylguanidine (300 mmole, fw=115.18) is added and the suspension is stirred at ambient temperature overnight (18 hrs). During this time, the reaction mixture becomes homogeneous. The reaction is heated to 70° C. for two hours to drive the reaction to completion. The reaction mixture is cooled to room temperature; the inner side of the glass flask is scratched to induce crystallization, and then the mixture is stirred at ambient temperature for about three hours during which time crystals begin to form. 100 mL acetone is added to the stirring mixture, and then it is stirred overnight (18 hrs) at room temperature to complete the crystallization. The mixture is filtered, and the white crystalline product is washed with 25 mL acetonitrile followed by acetone. The hygroscopic product is dried by passing dry nitrogen through it followed by drying in a vacuum oven at 50° C. overnight (18 hrs). This process yields a product (19.6 g, 60% yield, fw=295.28) that is typically 90-92% pure by HPLC with the major impurities being the tetramethylguanidinium bromide and the "dialkylated" byproduct. The acetonitrile wash (25 mL) is added to the filtrate solution along with 125 mL acetone. This mixture is again stirred at ambient temperature for 24-36 hours to yield a second crop of crystals that is filtered, washed with acetone and dried as before yielding 10.4 g (26%) of additional product (74-76% pure by HPLC). Total isolated yield is 86%.

Recrystallization is accomplished using hot ethanol. 20.0 g of crude free base product (85-95% pure) or 25.5 g crude hydrobromide product is dissolved in 30 mL hot absolute ethanol. Gaseous HBr is carefully bubbled into the warm ethanol solution until the pH is <1.0 (pH paper), and then continued for 1-2 minutes, with associated temperature rise due to the exothermic nature of bubbling gaseous HBr into absolute ethanol. The covered flask is allowed to cool to room temperature over a period of about 3 hours. Beautiful white crystals form. If the crystals do not form, the inside of the glass flask may be briefly scratched with a metal spatula (stainless steel) to induce crystallization. The flask is then cooled overnight at 4° C. The white crystals are quickly filtered at ambient temperature using a sintered glass filter, washed with 25 mL acetone/1-propanol (50/50 v/v) and then with pure acetone. Because the product is deliquescent, it is protected from moisture in the air using dry nitrogen blanket. The product is dried in a vacuum oven overnight at 50° C. and stored over $P_2O_5$ in a glass desiccator. This recrystallization method produces 17.5 g (76% recrystallization yield) of purified product with HPLC purity of 99.0%-99.8% when initial purity is about 90%.

EXAMPLE 2 (METHOD 2)

Preparation of N(2-(1',3'-dimethylimidazoline-2'-iminato)ethyl)trimethyl-ammonium chloride hydrochloride (77, fw=271.24)

27.73 g (2-aminoethyl)trimethylammonium chloride (200 mmole, fw=138.64) is suspended in 480 mL stirring dry, cooled (10° C.) acetonitrile (magnetic stirring) in a dried, 1000 mL Erlenmeyer flask. The reaction is carried out under an atmosphere of dry $N_2$. 33.82 g 2-chloro-1,3-dimethylimidazolinium chloride (200 mmole, fw=169.06) is added as a solid in three equal portions over a period of 30 minutes. The mixture is stirred at 10° C. for 30 minutes during which time 26.11 g dry diisopropylethylamine (202 mmole, fw=129.25) is added in a dropwise fashion. The reaction mixture is stirred and slowly warmed to room temperature (23° C.) over a period of about 30 minutes. Finally, the reaction mixture is refluxed (~80° C.) for about three hours. The reaction mixture is allowed to cool to room temperature, 8.40 g LiOH.H$_2$O (200 mmole, fw=41.96) in 240 mL absolute ethanol is added to the reaction mixture which is then stirred at ambient temperature overnight. The mixture is filtered through fritted-glass, and the solvents and free amine are removed under vacuum using a rotary evaporator. The mixture is dissolved in 400 mL absolute ethanol, heated at 70° C. for 30 minutes, then cooled to room temperature and then the solvent is again removed under vacuum. Finally, the mixture is dissolved in a minimum amount of hot absolute ethanol (80-100 mL), cooled to room temperature and then gaseous HCl is carefully added until the pH is acidic (pH<1.0 using pH paper). 50 mL acetone is added and the mixture is allowed to stand at room temperature for 2 hours and then at 4° C. overnight (18 hours). The mixture is filtered, and the white crystalline product is washed with acetone followed by diethylether. The hygroscopic product is dried by passing dry nitrogen through it followed by drying in a vacuum oven at 50° C. overnight (18 hrs). This procedure yields a product (42.8 g, 79%) that is ~95% pure by HPLC.

Recrystallization is accomplished using hot ethanol. 40.0 g crude hydrochloride product is dissolved in 60 mL hot absolute ethanol. Gaseous HCl is carefully bubbled into the warm ethanol solution until the pH is <1.0 (pH paper), and then continued for 1-2 minutes. Remember that bubbling gaseous HCl into absolute ethanol is an exothermic process. The covered flask is allowed to cool to room temperature over a period of about 3 hours. White crystals form. The flask is then cooled overnight at 4° C. The white crystals are quickly filtered at ambient temperature using a sintered-glass filter, quickly washed with 50 mL acetone/1-propanol (50/50 v/v) and then with diethyl ether. Because the product is deliquescent, it is protected from moisture in the air using dry nitrogen blanket. The product is dried in a vacuum oven overnight at 50° C. and stored over P$_2$O$_5$ in a glass desiccator. This recrystallization method produces 31.5 g (83% recrystallization yield) purified product with HPLC purity of 98.5%-99.5% when initial purity is about 95%.

EXAMPLE 3 (METHOD 3)

Preparation of N,N',N'-trimethyl-N,N'-bis(3-sulfopropyl)ethylenediammonium di-inner salt (66, fw=346.47)

20.44 g freshly distilled N,N,N'-trimethylethylenediamine (200 mmole, fw=102.18) and 120 mL dry reagent-grade acetonitrile are placed in a capped 250 mL Erlenmeyer flask with a magnetic stirring bar. The reaction mixture is cooled to about 10° C. 49.32 g 1,3-Propanesultone (404 mmole, fw=122.14) is separated into four equal portions of 12.33 g each, and the first portion is added portionwise to the cooled, stirring, reaction mixture at such a rate that the temperature does not rise over 20° C. (about 30 min.). Then the mixture is stirred at room temperature for 120 minutes. A small sample (10 µL) of the reaction mixture is taken for HPLC analysis, and then the second 12.33 g portion of the propanesultone is added using the same procedure. The reaction mixture is stirred again at ambient temperature for 120 minutes during which time the reaction mixture separates into two layers. The reaction mixture is shaken to create a homogeneous suspension, and a second 10 µL representative sample of the reaction mixture is taken for HPLC analysis. The stirring reaction mixture becomes completely homogeneous after 26.11 g dry diisopropylethylamine (202 mmole, fw=129.25) is added. The third 12.33 g portion of propanesultone is added to the cooled, stirring reaction mixture again using the same method of addition. Again, the mixture is stirred for 120 minutes at ambient temperature. A third 10 µL sample of the reaction mixture is taken for HPLC analysis. The fourth 12.33 g portion of propanesultone is added all at once to the reaction mixture at room temperature and them it is then stirred at ambient temperature for about 22 hours. Finally, the reaction mixture is briefly heated at 50° C. (about 20 minutes), cooled and sampled for the fourth time for HPLC analysis. At this stage, 200 mL absolute ethanol and 3.5 g activated carbon (Darco KB, 100 mesh) are added to the reaction mixture that is stirred for one additional hour at ambient temperature. This mixture is filtered through paper into a 2 L flask containing 830 mL absolute ethanol. The filter is washed with 150 mL absolute ethanol. The reaction mixture with ethanol in the 2 L flask is magnetically stirred while methanesulfonic acid (about 19.7 g, fw=96.10) is slowly added dropwise until the mixture is acidic (pH=1-2 using pH paper). During the acid addition, copious amounts of a white solid forms. This mixture is vigorously stirred at room temperature for about 18 hours facilitate complete crystallization of the product. The reaction mixture is briefly heated to about 50° C. and then filtered warm using fritted glass under a dry nitrogen atmosphere to protect the hygroscopic product from moisture. The white solid is washed twice with warm absolute ethanol, then diethylether (room temp.) and dried on the filter by sucking nitrogen or dry air through it. The solid is fully dried by placing it in a vacuum oven overnight (50° C., 25 torr). The yield is 65.9 g (95%) of an off-white, fine crystalline powder.

HPLC analyses after 100-mmole, 200-mmole and 300-mmole addition of sultone shows the presence of two monoalkylated products and one dialkylated product along with unreacted trimethylethylenediamine even during the early stages of reaction. It appears that there is little discrimination in the alkylation of the two nitrogen atoms of the starting diamine. Furthermore, there is little discrimination in the dialkylation rates between the two monoalkylated intermediates. There is little evidence of the formation of the trialkylated product, even at later stages of the reaction. HPLC analysis of the final crystals show a purity of about 93%. The product purity is largely dependent on the purity of the starting diamine.

Recrystallization is accomplished by suspending 50.3 g of the dried, crude product in 1000 mL of stirring absolute ethanol. Slightly less than one equivalent 138 mmole) of a suitable base (LiOH.H$_2$O, 5.79 g) is added portionwise, and the mixture is stirred at room temperature for 2 hours. 2.5 g activated carbon (Darco KB, 100 mesh) is added and the mixture is stirred for one hour longer. The mixture is then filtered through Celite® over fine filter-paper using a Buechner funnel (Celite® 545, Whatman #5). To the clear, stirring filtrate solution is added methanesulfonic acid (about 13.5 g, fw=96.10) in a dropwise fashion until the mixture is acidic (pH=1-2 using pH paper). The resulting white mixture is stirred for two hours at 50° C. The warm mixture is filtered, washed (absolute ethanol, then ether) and dried as before yielding 46.8 g (93%) of a white crystalline solid. The HPLC purity is about 98%. A second recrystallization, conversion to the soluble basic form followed by crystallization of the acidic form from absolute ethanol by the addition of acid, is carried out with a recovery of about 96% and purity of about 99%. Formic acid or 48% aqueous HBr may be used instead of methanesulfonic acid.

Modifications: The same method with little modification is used to carry out N,N'-dialkylation of N-methylpiperazine, N-methylhomopiperazine, N'-ethyl-N,N-dimethylethylenediamine, N'-benzyl-N,N-dimethylethylenediamine, N,N,N'-trimethyltrimethylenediamine. 1,4-butanesultone is readily substituted for propanesultone. With some modifications, bromoalkanesulfonic acids and their salts, bromoalkanephosphonic acids and their salts/esters as well as bromoalkanoic acids and their salts/esters are successfully used as alkylating agents.

EXAMPLE 4 (Method 4a)

Preparation of N-(2-hydroxy-3-trimethylammoniumpropyl)diethylamine chloride (10, fw=224.78)

These reactions use a concentrated (70-75%) aqueous solution of technical grade 2,3-epoxypropyl-trimethylammonium chloride (GMAC). It is important to have fresh preparations of this material with known concentration and known purity. Generally, these reactions are clean and very efficient (good yield and good purity). However, impurities in GMAC lead to loss of yield and degradation of purity. The impurities themselves, even if inert, inhibit crystallization and complicate purification. Technical grade material can vary in purity between 75-95% (determined by HPLC, not titration); only material with actual purity in the range 90-95% is used. As long as the actual GMAC concentration (determined by HPLC) is in the range of 70-75%, and the actual value is known to the nearest 0.2%, it is acceptable. Good quality GMAC should be stored cold (4° C.) and used within 2 months of analysis. For these reactions, GMAC concentration is 72.9% and GMAC purity is 92%.

329.13 g freshly distilled diethylamine (4.5 mole, fw=73.14) is placed in a 2 Liter flask equipped with a mechanical stirrer and then cooled to 5° C. 667.2 g GMAC (4.4 mole, fw=151.64, 915.2 g 72.9%) in water is added slowly in a dropwise fashion to the stirred amine. The temperature is carefully monitored, and the addition rate is adjusted to maintain the reaction temperature below 10° C. After complete addition of GMAC (about 3 hours), the reaction mixture is stirred overnight (18 hours) at room temperature. From time-to-time, absolute ethanol is added to (1) maintain a single liquid phase and to (2) reduce the viscosity to facilitate stirring; in this reaction, about 400 mL absolute ethanol is added. The reaction mixture is heated at 50° C. for about two hours, and then the solvents (water, ethanol, excess amine) are removed under vacuum using a rotary evaporator until the reaction product is nearly dry. The light amber reaction mass is dissolved in a minimum amount of hot acetonitrile (750-950 mL). The hot solution is rapidly filtered through sintered-glass and then slowly cooled to room temperature (about 4 hours) during which time white crystals begin to form. If crystals do not spontaneously form, the reaction flask is scratched with a stainless steel spatula or seed crystals of the same purified product are added. Usually crystal formation begins with 1-2 hours, but can take as long as two days without seed crystals. The mixture is then allowed to stand at 4° C. overnight (18 hours) producing a white crystalline mass. The white crystals are collected by filtration through sintered-glass, washed with acetone and then dried on the filter by sucking nitrogen or dry air through it. The solid is fully dried by placing it in a vacuum oven overnight (50° C., 25 torr) and stored over $P_2O_5$ in a glass desiccator. The yield is 614 g (62%) of a white deliquescent, crystalline solid with a typical purity of 92-96% (HPLC). Recrystallization of 500 g of this material from minimum amount of hot acetonitrile using the same procedure afforded 418 g (88% recrystallization yield) of a product that is 98-99% pure.

Hydrochloride Adduct (Method 4b) (fw=261.24): This procedure is the same as Method 4a with the addition of HCl near the end and crystallization of the more easily handled hydrochloride adduct.

329.13 g freshly distilled diethylamine (4.5 mole, fw=73.14) is placed in a 3 Liter flask equipped with a mechanical stirrer and then cooled to 5° C. 682.4 g GMAC (4.5 mole, fw=151.64, 936.1 g 72.9%) in water is added slowly in a dropwise fashion to the stirred amine. The temperature is carefully monitored, and the addition rate is adjusted to maintain the reaction temperature below 10° C. After complete addition of GMAC (about 3 hours), the reaction mixture is stirred overnight (18 hours) at room temperature. From time-to-time, absolute ethanol is added during the course of the reaction to (1) maintain a single liquid phase and to (2) reduce the viscosity for facile stirring; in this reaction, a total of about 400 mL absolute ethanol is added. The reaction mixture is heated at 50° C. for about two hours, and the mixture is allowed to cool to room temperature. 400 mL 37% reagent hydrochloric acid (fw=36.46, den.=1.20 g/mL, 4.87 mole) is added portionwise to the stirring solution over a period of 60 minutes; a mild exotherm is observed. All solvents (water, ethanol, excess acid) are removed under vacuum using a rotary evaporator until the reaction product is nearly dry. The light amber reaction mass is dissolved in a minimum amount of hot absolute ethanol/isopropanol (50/50 v/v) (1.5-1.9 L). The hot solution is rapidly filtered through sintered-glass and then slowly cooled to room temperature (about 4 hours) during which time white crystals begin to form. If crystals do not spontaneously form, the reaction flask is scratched with a stainless steel spatula or seed crystals of the same purified product are added. Usually crystal formation begins with 1-2 hours, but can take longer without seed crystals. After standing at room temperature for about 42 hours, the mixture is then allowed to stand at 4° C. for 48 hours producing a white crystalline mass. The white crystals are collected by filtration through sintered-glass, washed with acetone and then dried on the filter by passing nitrogen or dry air through it. The solid is fully dried by placing it in a vacuum oven overnight (50° C., 25 torr) and stored over $P_2O_5$ in a glass desiccator. The yield is 846 g (72%) of a white deliquescent, crystalline solid with a typical purity of 90-95% (HPLC). Recrystallization of 500 g of this material from a minimum amount of hot absolute ethanol/isopropanol containing added gaseous HCl (pH<1.0 with pH paper) using the analogous procedure above afforded 398 g (86% recrystallization yield) of a product that is 98.5-99.5% pure.

Modifications: Methods 4a and 4b are used with a wide range of secondary amines and are carried out on small scale (0.5 mole) and/or large scale (4.5 mole): dimethylamine (40% aqueous, 30% in absolute ethanol), ethyl methyl amine, N-methyl-2-methoxyethylamine, diethylamine, pyrrolidine, piperidine, morpholine, 4-hydroxy-piperidine (50% in absolute ethanol), N-methylethanolamine, N-ethylethanolamine, N-isopropylethanolamine, diethanolamine, N-acetylpiperazine (50% in absolute ethanol), bis(2-methoxyethyl)amine. Recrystallization solvents for the unprotonated amine-quats are hot acetonitrile or hot acetonitrile/2-butanone (75/25 v/v). Recrystallization solvents for the hydrochloride adducts are hot absolute ethanol or hot absolute ethanol/isopropanol (50/50 v/v).

Method 4b is also used with primary amines used in excess (2×): methylamine (40% aqueous, 30% absolute ethanol), ethylamine (70% aqueous, 50% absolute ethanol), isopropylamine, ethanolamine, 2-methoxyethylamine. The excess, unreacted primary amine can be recycled for subsequent use.

EXAMPLE 5a (METHOD 5a)

Preparation of
N-(2-trimethylammoniumethyl)dimethylamine
chloride (27, fw=166.70)

348.63 g freshly distilled N,N,N',N'-tetramethylethylene-diamine (3.0 mole, fw=116.21) and 750 mL acetone are placed in a 1.7 Liter heavy-walled, glass pressure vessel that is equipped with a magnetic stirring-bar, thermocouple and pressure head with relief valve. Methyl chloride gas is periodically vented into the closed, stirring reaction mixture at 5 psig so as to maintain a mild exotherm below 35° C. The amount of methyl chloride addition to the system is periodically measured by gravimetrically monitoring the additional weight gain with time. The sealed reaction vessel can be disconnected from the gas source. The initial weight of the closed vessel and contents are measured before methyl chloride addition, and subsequent weight measurements indicate the weights of added methyl chloride. Addition of methyl chloride is also measured by loss of weight of the pressurized cylinder of methyl chloride. The two methods of measurement usually give about the same value to within ±0.5 g. Over a period of 3-6 hours, a total of 121.1 g of methyl chloride (2.4 mole, fw=50.49) is added. During this time a white crystalline solid begins to form. The reaction mixture is stirred at room temperature overnight (18 hours), the reaction vessel is vented in a hood, and then the reaction mixture is filtered through sintered-glass. The crude product is suspended in a minimum amount of hot acetonitrile (~600 mL). The hot stirring mixture is allowed to slowly cool, and when the temperature reaches 65° C., it is quickly filtered through sintered-glass to remove some of the dimethylated product. The mixture is further cooled and allowed to stand at room temperature for 24 hours. The mixture is filtered to obtain the first crop of crystals. In this example, there is no solvent removal at this point (see below). 300 mL acetone is added to the filtrate that is then allowed to stand at 4° C. for 24 hours to obtain a second crop of crystals. The cold acetonitrile/acetone mixture is filtered through sintered glass, and the two crops of crystals are combined to yield 328.0 g (82%) of a hygroscopic white crystalline solid with purity (HPLC) of 90-94%. The principal impurity is the inert dimethylated byproduct. One or two recrystallizations from hot acetonitrile or hot isopropanol leads to pure material (98-99%).

EXAMPLE 5b (METHOD 5b)

Preparation of 4-(N-ethylisopropylamino)-1,1-di-ethyl-piperidinium bromide (74, fw=307.33)

14.23 g Freshly distilled 4-(isopropylamino)piperidine (100 mmole, fw=142.25), 28.43 g diisopropylethylamine (DIPEA, 220 mmole, fw=129.25) and 75 mL acetonitrile are placed in a 200 mL heavy-walled, glass pressure vessel that is equipped with a magnetic stirring-bar, thermocouple and pressure head with relief valve. 35.96 g ethyl bromide (330 mmole, fw=108.97) is added to the stirring mixture and pressure vessel is sealed. Initially there is a mild exotherm. The reaction mixture is heated and stirred at 40° C. for 24 hours, and then it is cooled to room temperature. During cooling, white crystals of DIPEA hydrobromide begin to form. The reaction vessel is vented in a hood, and then the reaction mixture is filtered through sintered-glass to remove the unwanted solid. The solvent is removed on a rotary evaporator, and then just enough 50% aqueous NaOH is added (~28 g) until the mixture is strongly basic. The liquid (acetonitrile, water, DIEPA) is removed using a rotary evaporator and then a vacuum pump (0.5 torr). The residue is twice extracted with 100 mL hot acetonitrile, and the liquids are combined. Anhydrous magnesium sulfate (~15 g) is added, the liquid is filtered and then placed on a rotary evaporator to remove most of the solvent. Small amounts of acetonitrile are added back to ensure a homogeneous solution, and then peroxide-free diethylether is added to induce crystallization. The mixture is allowed to stand at room temperature for about 4 hours and then at 4° C. overnight. The cold acetonitrile/ether mixture is filtered through sintered glass, washed with ether and then dried by passing dry $N_2$ through the filter. The off-white solid is dried in a vacuum oven overnight yielding 22.1 g (72%) of a sticky, white crystalline solid with purity (HPLC) of about 97%. Recrystallization from acetonitrile/isopropanol/ether mixtures yields a purified product (~99%). This reaction illustrates a method to carry out multiple alkylations of primary and secondary amines in the presence of a strong, soluble, nonreactive base. Despite the excess alkylating agent, there was no evidence (HPLC) of the tetraalkylated impurity in the reaction mixture or in the final trialkylated product.

Modifications: Method 5 is a general method for monoalkylation of wide variety of symmetric tertiary diamines and, in some cases, unsymmetric tertiary diamines. Under more forcing conditions (time, temperature), this method also works well for dialklyation of symmetric and unsymmetric diamines; in this case, solvents such as acetonitrile, absolute ethanol or mixtures thereof are used. Smaller tertiary diamines (dimethylpiperazine, tetramethylethylene-diamine) lead to higher yields and purities. Longer diamines (tetramethylhexamethylenediamine) produce higher amounts of dialkylation, require more recrystallization and lead to lower yields of pure monoalkylated product. In the cases where dialkylation is more problematic, lesser amounts of methyl chloride are used, and the unreacted diamine is recycled. In some cases, the solvent is changed to diethyl ether/acetone (50/50 v/v) and the level of dialkylation is reduced. When the filtrate solution is being prepared to obtain a second batch of crystals by cooling, sometimes the filtrate is first reduced in volume by about half; sometimes 100-900 mL acetone is added. Sometimes both procedures are carried out—partial acetonitrile removal and acetone addition.

EXAMPLE 6 (METHOD 6)

Preparation of N,N,N',N'-tetramethyl-N-(3-sulfopro-pyl)-1,3-propanediamine Inner salt (57, fw=252.38)

273.50 g freshly distilled N,N,N',N'-tetramethyl-1,3-pro-panediamine (2.1 mole, fw=130.24) and 600 mL acetone are placed in a 2 L flask that is equipped with a mechanical stirrer and a thermometer. A solution of 244.28 g 1,3-propanesul-tone (2.0 mole, fw=122.14) in 200 mL acetone is slowly added over a period of about three hours to the stirring amine solution. A mild exotherm is observed (~10° C.), and a white crystalline solid comes out of solution. The mixture is stirred overnight (18 hours) at room temperature, filtered through sintered-glass, washed with small amounts of acetone and dried on the filter.

Procedure (a): The white solid is dissolved in a minimum amount of hot acetonitrile (~1400 mL), and then the hot solution is filtered through a Celite® pad to remove the poorly soluble dialkylated byproduct. The hot filtrate is cooled to room temperature for about three (3) hours and then allowed to stand at 4° C. for 48 hours. The white crystals are collected by filtration through sintered-glass, washed with acetone and then dried on the filter by passing dry nitrogen or dry air through it. The solid is fully dried by placing it in a vacuum oven overnight (50° C., 15 torr). The yield is 308 g (61%) of a white crystalline solid with a typical purity of ~96% (HPLC). Recrystallization of 300 g of this material from a minimum amount of hot acetonitrile using the same procedure above afforded 259 g (90% recrystallization yield) of a product that is 98-99% pure.

Procedure (b): The white solid is suspended in 700 mL warm (60° C.) absolute ethanol, and gaseous HCl is carefully bubbled through the mixture until it is acidic (pH<2.0 by pH paper). The mixture is briefly heated to about 75° C. and then filtered through a Celite® pad to remove the poorly soluble dialkylated byproduct. The hot filtrate is cooled to room temperature for about three (3) hours and then allowed to stand at 4° C. for 48 hours. The white crystals of the hydrochloride salt (fw=288.84) are collected by filtration through sintered-glass, washed with acetone and then dried on the filter by passing dry nitrogen or dry air through it. The solid is fully dried by placing it in a vacuum oven overnight (50° C., 15 torr) and stored over $P_2O_5$ in a glass desiccator. The yield is 416 g (72%) of a white crystalline solid with a typical purity of ~97% (HPLC). Recrystallization of 400 g of this material from a minimum amount of hot acetonitrile using the same procedure above afforded 326 g (84% recrystallization yield) of a product that is 98-99% pure.

Procedure (c): The white solid is suspended in 700 mL warm (60° C.) absolute ethanol, and gaseous HCl is carefully bubbled through the mixture until it is acidic (pH<2.0 by pH paper). The mixture is briefly heated to about 75° C. and then filtered through a Celite® pad to remove the poorly soluble dialkylated byproduct. Enough $LiOH.H_2O$ is added portionwise to the stirring warm (60° C.) filtrate until the pH is basic (pH>11.0 by pH paper). The neutral free amine is poorly soluble in absolute ethanol and crystallizes out of solution. The mixture is cooled to room temperature, stirred overnight (18 hours) and finally allowed to stand at 4° C. for 24 hours. The white solid collected by filtration through sintered-glass, washed with acetone and then dried on the filter by passing dry nitrogen or dry air through it. The solid is fully dried by placing it in a vacuum oven overnight (50° C., 15 torr). The yield is 403 g (80%) of a white crystalline solid with a typical purity of ~96% (HPLC). Recrystallization of 400 g of this material is accomplished by suspending it in warm absolute ethanol, converting to the soluble hydrochloride salt, filtering the warm solution, converting back to the neutral free amine with base and crystallizing from cold ethanol. This procedure affords 349 g (91% recrystallization yield) of a product that is 98-99% pure.

EXAMPLE 7 (METHOD 7)

Preparation of N-(2-hydroxy-3-trimethylammonium-propyl)-N-(2-hydroxyethyl)homotaurine inner salt (51, fw=252.38)

Step 1 (Method 7a): N-j-hydroxyethyl)homotaurine, inner salt (fw=183.23) 219.89 g freshly distilled ethanolamine (3.6 mole, fw=61.08) and 1200 mL absolute ethanol are placed in a dry 2 L Erlenmeyer flask that is equipped with a large magnetic stirring bar and a thermometer. 146.57 g liquified (mp=31° C.) 1,3-propanesultone (1.2 mole, fw=122.14) is slowly added over a period of about three (3) hours to the vigorously stirring amine solution. Periodic use of a cooling bath coupled with slow addition of sultone allows the temperature of the exothermic reaction to be maintained in the range 20-30° C. The mixture is stirred for two more hours at room temperature. Finally methanesulfonic acid (~231 g, 2.4 mole, fw=96.11) is added dropwise to the stirring mixture until it becomes acidic (pH<2.0, pH paper). The mixture is then stirred at room temperature for 2 hours and overnight (18 hours) at 4° C. Upon acidification, the product comes out of solution as a colorless oil that converts into a white crystalline solid upon stirring (<1 hour if seeded or 2-24 hours if not seeded). The liquid is removed by decanting or filtering, and 1000-1200 mL absolute ethanol is added. This mixture is vigorously stirred for 6 hours at room temperature, filtered through sintered-glass under a blanket of $N_2$ or dry air, washed with absolute ethanol and acetone and dried on the filter.

The product is suspended in about 800 mL absolute ethanol, and about one equivalent of a soluble base (triethylamine, $LiOH.H_2O$, tetramethylguanidine etc) is added dropwise until most of the taurine is dissolved. The mixture (room temperature) is filtered to remove salts and other insolubles, and about one equivalent of a soluble acid (methanesulfonic, gaseous HCl) is added dropwise until the pH is acidic. White crystals of the product begin to crystallize from solution, and the mixture is stirred overnight at room temperature. The white crystals are collected by filtration through sintered-glass, washed with absolute ethanol and acetone and then dried on the filter by passing dry nitrogen or dry air through it. The solid is fully dried by placing it in a vacuum oven overnight (50° C., 15 torr). The yield is 196 g (89%) of a white crystalline solid with a typical purity of ~99% (HPLC). The purification by crystallization is based on the fact that the starting amine (free and protonated) and the dialkylated byproduct (free and protonated) are both soluble in basic and acidic absolute ethanol. In contrast, the product is soluble in basic absolute ethanol but poorly soluble in acidic absolute ethanol. Furthermore, sodium salts (NaCl, NaBr, etc.), if present, have limited solubility in basic and acidic absolute ethanol.

Modifications: This method is used with a range of primary amines: methylamine (40% aqueous, 30% in absolute ethanol), ethylamine (70% aqueous, 50% absolute ethanol), isopropylamine, 2-methoxyethylamine, glycinamide. If aqueous solutions of primary amines are used, then aqueous solutions of a strong acid (conc. HCl) can be used. In this case, the solvents (water, ethanol) are completely removed under reduced pressure, and the residue is dissolved/suspended in absolute ethanol. When volatile amines are used, an appropriate base (e.g., $Et_3N$, $LiOH.H_2O$, 50% aqueous NaOH) is added at the end of the reaction sequence, and then the solvent and unreacted amine are removed under vacuum. The reaction mixture is dissolved in absolute ethanol, the solution filtered, and then methanesulfonic acid (or other acid) is added. In this case, much less acid is needed because much of the unreacted amine is removed. In this preparation, an excess (3×) of the amine is used to retard dialkylation. The excess unreacted amine is easily recovered for reuse if needed. Other alkylating agents work fine. 1,4-Butanesultone can be used without modifications. Sodium 3-chloro-2-hydroxypropanesulfonate has limited but sufficient solubility in absolute ethanol; reaction times are typically 12-24 hours with stirring at room temperature. The low solubility of sodium 2-bromoethanesulfonate in absolute ethanol requires that ethanol/water (70/30 v/v) be used; in addition a 10-20% excess is needed owing to its partial hydrolysis in the reaction solvent.

Step 2 (Method 7b): 183.23 g N-(2-hydroxyethyl)homotaurine, inner salt (1.0 mole, fw=183.23) is dissolved in a solution of 142.2 g diisopropylethylamine (1.1 mole, fw=129.25) and 700 mL absolute ethanol contained in a 2 L Erlenmeyer flask that is equipped with a mechanical stirrer and a thermometer. 151.6 g GMAC (1.0 mole, fw=151.64, 208.1 g 72.9%) in water is added slowly in a dropwise fashion to a cold (5-10° C.), vigorously stirred N-hydroxyethyl-homotaurine solution over a period of about three (3) hours. During the course of the reaction, a white crystalline solid or a clear oily liquid (which later solidifies) separates from solution. The temperature is carefully monitored, and the addition rate is adjusted to maintain the reaction temperature below 10° C. After complete addition of GMAC, the reaction mixture is stirred overnight (18 hours) at room temperature. Finally, the reaction mixture is heated at 50° C. for about 1-2 hours, and then the solvents (water, ethanol) are removed under vacuum using a rotary evaporator until the reaction mixture is nearly dry. The reaction mass is re-suspended in hot absolute ethanol (750 mL), the pH is verified to be >10.0 (pH paper), and the mixture is vigorously stirred as it cools to room temperature (~2 hours) to facilitate crystallization. The white crystals are collected by filtration through sintered-glass, washed with absolute ethanol and acetone and then dried on the filter by sucking nitrogen or dry air through it.

The product is recrystallized by suspending it in 750 mL absolute ethanol and adding enough methanesulfonic acid (76-92 g) or other acid such as gaseous HCl to form the protonated product which is soluble in ethanol. The solution is filtered through a Celite® pad on a Buechner filter, and then a base (80-102 g $Et_3N$ or other soluble hydroxide) is added in a dropwise manner leading to crystallization of the deprotonated product. The reaction mixture is stirred at room temperature for about 3 hours, filtered through sintered-glass, washed with absolute ethanol and acetone and finally dried on the filter by passing dry nitrogen or dry air through it. The solid is fully dried by placing it in a vacuum oven overnight (50° C., 15 torr). The yield is 192 g (76%) of the dry white microcrystalline solid which has a typical purity of 98-99% (HPLC). The purification by crystallization is based on the fact that the starting taurine and the dialkylated byproduct are both soluble in basic absolute ethanol. In contrast, the product is soluble in acidic absolute ethanol but poorly soluble in basic absolute ethanol. Furthermore, sodium salts (NaCl, NaBr, etc.), if present, have limited solubility in basic and acidic absolute ethanol.

Modifications: This is a general method for making a range of compounds from N-monosubstituted taurines, homotaurines, related aminoalkanesulfonic acids and aminoalkanoic acids when the monosubstitution is a neutral, uncharged group (not anionic, not cationic). If the monosubstitution contains a carboxamide moiety, care is taken not to hydrolyze it in overly acidic or overly basic conditions. In place of GMAC, bromoalkyl quaternary ammonium salts are also successfully used.

Step 3 (Method 7C): N-(3-trimethylammonium-2-hydroxypropyl)ethanolamine chloride hydrochloride (78a) is prepared by Method 4b above. 249.19 g of this compound (1.0 mole, fw=249.19) is dissolved in a solution of 122.8 g diisopropylethylamine (0.95 mole, fw=129.25) and 750 mL absolute ethanol contained in a 2 L Erlenmeyer flask that is equipped with a mechanical stirrer and a thermometer. 122.14 g liquified (mp=31° C.) 1,3-propanesultone (1.0 mole, fw=122.14) is slowly added over a period of about three (3) hours to the vigorously stirring solution of the secondary amine. Periodic use of a cooling bath coupled with slow addition of sultone allows the temperature of the exothermic reaction to be maintained in the range 20-30° C. The reaction mixture is stirred overnight (18 hours) at room temperature, and then more diisopropylethylamine (~6 g) is added dropwise until the point of incipient precipitation of the product. The reaction mixture is allowed to stir at room temperature for an additional 4-6 hours. The product is then brought out of solution (colorless oil or white solid) by addition of sufficient base (~130 g $iPr_2NEt$; or alternatively tetramethylguanidine, $Et_3N$, 50% aqueous NaOH, NaOEt, LiOEt, $LiOH.H_2O$) so that the solution is basic (pH>10.0, pH paper). The reaction mixture is again stirred overnight (18 hours) at room temperature leading to the formation of a white, crystalline product. The product is collected by filtration through sintered-glass, washed with absolute ethanol and acetone and then dried on the filter by sucking nitrogen or dry air through it. It is recrystallized according to Method 7a—Step 2. The reaction mixture is filtered through sintered-glass, washed with absolute ethanol and acetone and finally dried on the filter by passing dry nitrogen or dry air through it. The solid is fully dried by placing it in a vacuum oven overnight (50° C., 15 torr). The yield is 215 g (85%) of a dry white microcrystalline solid that has a typical purity of 98-99% (HPLC).

Modifications: This is a general method for this class of zwitterionic amines. Other alkylating agents work similarly. 1,4-butanesultone can be used without modifications. Sodium 3-chloro-2-hydroxypropanesulfonate has limited but sufficient solubility in absolute ethanol; reaction times are extended by 12-24 hours at room temperature. The low solubility of sodium 2-bromoethanesulfonate in absolute ethanol requires that ethanol/water (70/30 v/v) be used; in addition a 10-20% excess is needed owing to its partial hydrolysis in the reaction solvent. Alternative organic and inorganic bases besides diisopropylethylamine are also used. In addition to the N-(2-hydroxyethyl) derivative above, a range of starting materials, secondary amine-quat compounds, can be used that contain N-methyl, N-ethyl, N-isopropyl, N-(2-methoxyethyl) groups.

EXAMPLE 8 (METHOD 8)

Preparation of 1,1,5,9-tetramethyl-2-hydroxy-5,9-bis (2-sulfoethyl)-1,5,9-triazanonane di-inner salt (82, fw=419.57)

Step 1 (Method 8a): N,N'-dimethyl-N,N'-bis(2-sulfoethyl)-1,3-propanediamine, di-inner salt (fw=318.42, [185305-85-5])

102.18 g freshly distilled N,N'-dimethyl-1,3-propanediamine (1.0 mole, fw=102.18, [111-33-1]) and 1500 mL ethanol/water (70/30 v/v) are placed in a 3 L Erlenmeyer flask that is equipped with a mechanical stirrer and a thermometer. 258.5 g Diisopropylethylamine (2.0 mole, fw=129.25) and 422.1 g 2-bromoethanesulfonic acid, sodium salt (2.0 mole, fw=211.01) are added portionwise over a period of about seven (7) hours to the vigorously stirring diamine solution. The reaction mixture is stirred at room temperature for about 42 hours and monitored periodically by HPLC. The reaction rate is limited by the solubility of the sodium salt of the sulfonic acid. Once the reaction is come to completion (~42 hours) and the bromoethylsulfonate is consumed, the amount of additional alkylating agent that is needed to complete the reaction is estimated from the HPLC data. Then additional diisopropylethylamine (0.3 mole, ~39 g) and bromoethylsulfonate (0.3 mole, ~64 g) are added because some bromoethylsulfonate is lost to hydrolysis. The reaction mixture is stirred again at room temperature for about 22 hours. This process is repeated until all of the starting amine has been cleanly dialkylated with little evidence of trialkylation. The reaction mixture is heated to 60° C. for about 1 hour and then filtered to remove any solids. The solvent (water, ethanol) is removed under vacuum until the residue is nearly dry. The residue is dissolved/suspended in 1500 mL absolute ethanol, the pH is verified to be basic (pH>10.0, pH paper), the mixture is stirred at 70° C. for about 3 hours and then allowed to cool to room temperature while stirring. The reaction mixture is filtered again to remove solids, and then methanesulfonic acid (~220 g, fw=96.11) is added portionwise to the stirring mixture until it becomes acidic (pH<2.0, pH paper). During acidification, the product comes out of solution, initially as a sticky solid and then as fine white crystals. The mixture is then stirred at room temperature for 3 hours and overnight (18 hours) at 4° C. The reaction mixture is filtered through sintered-glass under a blanket of $N_2$ or dry air, washed with absolute ethanol and acetone and dried on the filter.

The product is recrystallized by suspending the solid in 1200 mL stirring absolute ethanol and adding enough base ($Et_3N$) until most is dissolved. The solution is filtered to remove solids and enough acid (methanesulfonic acid or gaseous HCl) is added to the filtrate in a portionwise manner until the pH is acidic (pH<2.0, pH paper). Addition of acid causes a mass of white microcrystals to come out of solution. The mixture is stirred at room temperature overnight (18 hours), filtered through sintered-glass under a blanket of dry $N_2$ or dry air, washed with absolute ethanol and acetone and dried on the filter. The solid is fully dried by placing it in a vacuum oven overnight (50° C., 15 torr). The yield is 252 g (79%) of a dry white microcrystalline solid that has no detectable impurity (>99%, HPLC).

Step 2 (Method 8b): 1-benzyl-1,1,5,9-tetramethyl-3-hydroxy-5,9- bis(2-sulfoethyl)-1,5,9-triazanonane, di-inner salt (fw=509.69):

251.6 g freshly crystallized N,N'-dimethyl-N,N'-bis(2-sulfoethyl)trimethylene-diamine, di-inner salt (0.79 mole, fw=318.42, [185305-85-5]) is dissolved in a stirring mixture of 1000 mL ethanol/water (80/20 v/v) and diisopropylethylamine (0.80 mole, 103.4 g, fw=129.25) at room temperature. Over a period of about six (6) hours, 198.15 g carefully recrystallized N-(3-chloro-2-hydroxypropyl)benzyldimethylammonium chloride (0.75 mole, "benzyl reagens", >99.5% purity, FW=264.20, [67304-25-0]) and 100.9 g diisopropylethylamine are individually added portionwise to the stirring reaction mixture at ambient temperature. A mild exotherm is observed. The temperature is slowly increased to about 60° C. over 60 minutes, and the temperature is maintained at that temperature overnight (~18 hours). The reaction is followed by HPLC to monitor the disappearance of the benzyl reagents starting material. The solvent is completely removed under vacuum using a rotary evaporator, 850 mL absolute ethanol is added, the pH is adjusted (if needed) so that is basic (pH>9.5, pH paper), and the mixture is stirred at 60° C. for one hour. The mixture is allowed to cool to about 30° C., and then it is filtered using fritted-glass and washed with absolute ethanol and acetone. The white solid is suspended in 800 mL stirring absolute ethanol at 40° C., and methanesulfonic acid (~72 g) is added dropwise until most or all of the product is dissolved. The mixture is filtered warm to remove undissolved solid, and then base is added dropwise to the stirring filtrate until it is basic (pH>9.5, pH paper) during which time which crystals of the product crystallize out of solution. The solution is cooled at 4° C. overnight and then filtered through sintered-glass, washed with absolute ethanol and acetone and then dried on the filter. The solid is fully dried by placing it in a vacuum oven overnight (50° C., 15 torr). The yield is 322 g (81%) of a dry white microcrystalline solid that has a typical purity of ~94% (HPLC). Recrystallization from hot absolute ethanol gave a product with purity >98% (90% recrystallization yield).

Step 3 (Method 8c): 1,1,5,9-tetramethyl-3-hydroxy-5,9-bis(2-sulfoethyl)-1,5,9-triazanonane di-inner salt (fw=419.57)

305.8 g 1-benzyl-1,1,5,9-tetramethyl-3-hydroxy-5,9- bis (2-sulfoethyl)-1,5,9-triazanonane, di-inner salt (fw=509.69), 9.61 g methanesulfonic acid (0.10 mole, fw=96.11) and 900 mL ethanol/water (90/10 w/w) are placed in a 1.7 liter heavy-walled glass pressure vessel equipped with a magnetic stirring-bar, thermocouple and pressure head with relief valve. Catalyst (6.0 g 5% Pd/C) is added to the mixture, the pressure container is sealed and then pressurized to 35 psig with hydrogen gas ($H_2$) and vented three times. Finally, the stirring mixture is pressurized and maintained at 35 psig hydrogen with a temperature of 40° C. for about four (4) hours. The stirring reaction is continued overnight (~18 hours) at ambient temperature with 35 psig $H_2$. The pressure bottle is vented, the reaction mixture is filtered through a Celite® pad to remove the insoluble catalyst, and the volume of the filtrate is reduced to about 800 mL using a rotary evaporator. This solution is heated to 60° C., base is added (~13 g diisopropylethylamine) until the pH is about neutral (pH=7.0, pH paper). The product begins to come out of solution as white crystals. The mixture is slowly cooled to room temperature (~3 hours), and the mixture is then allowed to stand at 4° C. overnight (18 hours). The white crystals are collected by filtration through sintered-glass, washed with acetone and then dried on the filter by sucking nitrogen or dry air through it. A second crop of crystals is obtained as follows. The filtrate is reduced in volume to about 500 mL, the pH is checked and adjusted if needed (pH~7.0), the mixture is seeded with crystals of the product, cooled to 4° C. overnight and filtered and washed as before. The solid is fully dried by placing it in a vacuum oven overnight (50° C., 15 torr) and stored over $P_2O_5$ in a glass desiccator. The total yield is 237 g (94%) of a white crystalline solid with a typical purity of 98-99% (HPLC). Recrystallization of the product is usually not needed.

EXAMPLE 9 (METHOD 9)

Preparation of (3-trimethylammoniumpropyl) dimethylamine chloride hydrochloride (29a, fw=217.19)

30.53 g (3-aminopropyl)trimethylammonium chloride (200 mmole, fw=152.67) is carefully added portionwise to 48.5 g 95% formic acid (1000 mmole, fw=46.03). The warm mixture is magnetically stirred in a 250 mL Erlenmeyer flask under a nitrogen atmosphere and then cooled to room temperature using external cooling. 40.6 g 37% formaldehyde (500 mmole, fw=30.03) is added to the reaction mixture which is heated at 65° C. overnight (18 hours). When the temperature reaches about 50° C., bubbles of $CO_2$ begin to come out of solution. The temperature of the reaction mixture is then raised to 95° C. for one (1) hour and then allowed to cool to room temperature. Finally, about 22 g of 37% hydrochloric acid (220 mmole, fw=36.46) is added in a dropwise fashion to the stirring mixture until it becomes acidic (pH<2.0, pH paper). The solvent and unreacted starting materials are completely removed under vacuum using a rotary evaporator. The mixture is suspended in about 100 mL absolute ethanol, heated at 70° C. for 30 minutes, filtered through sintered-glass, cooled to room temperature and then the solvent is again completely removed under vacuum. Finally, the mixture is dissolved in a minimum amount (80-100 mL) of a hot mixture of absolute ethanol/isopropanol (50/50 v/v), rapidly filtered through sintered-glass, cooled to room temperature and then gaseous HCl is carefully added until the pH is acidic (pH<1.0, pH paper). The mixture is allowed to stand overnight and then filtered to obtain the first crop of crystals. 50 mL acetone is then added to the filtrate, the mixture is allowed to stand at room temperature for 2 hours and then at 4° C. overnight (18 hours). The mixture is filtered again to obtain a second crop of a white microcrystalline product. The two crops are combined, washed with isopropanol/acetone (50/50 v/v), then with acetone followed by diethylether. The somewhat hygroscopic product is dried by passing dry nitrogen through it followed by drying in a vacuum oven at 50° C. overnight (18 hrs). This procedure yields a product (38.6 g, 89%) that is 96-98% pure by HPLC. Recrystallization from dry, hot ethanol/isopropanol containing HCl produces a product that is ~99% pure by HPLC.

Modifications: Reasonable results are obtained if 200 mmole of (2-aminoethyl)-trimethylammonium chloride•hydrochloride is used as the starting material. In this case, 200 mmole of NaOH (50% aqueous) in also added at the beginning. This is a general technique (Eschweiler-Clarke methylation) for methylation of primary and secondary amines. In the case of secondary amines, half the amounts of formic acid and formaldehyde solution are added; sometimes some additional water is needed for adequate solubility.

EXAMPLE 10 (METHOD 10)

Preparation of
N-(3-trimethylammoniumpropyl)-diethylamine
bromide hydrobromide (17, fw=334.14)

26.10 g (3-bromopropyl)trimethylammonium bromide (100 mmole, fw=261.01) is suspended in 200 mL stirring acetonitrile (magnetic stirring) in a 500 mL Erlenmeyer flask. 21.95 g diethylamine (300 mmole, fw=73.14) is added and the suspension is stirred at ambient temperature overnight (18 hrs). During this time, the reaction mixture becomes homogeneous. The reaction is heated to 55° C. for two hours to drive the reaction to completion. The reaction mixture is cooled to room temperature, gaseous HBr is added until the mixture becomes acidic (pH<2.0, pH paper), and the product crystallizes as white crystals. If crystallization does not occur or if a clear oil forms, the inner side of the glass flask is scratched to induce crystallization or seed crystals are added, and then the mixture is stirred at ambient temperature for about three hours during which time crystals begin to form. 200 mL acetone is added to the stirring mixture, and then it is stirred overnight (18 hours) at 4° C. to complete the crystallization. The mixture is filtered, and the white crystalline product is washed with 25 mL acetone. The product is dried by passing dry nitrogen through it followed by drying in a vacuum oven at 50° C. overnight (18 hrs). This process yields a white microcrystalline product (30.4 g, 91% yield) that is typically 96-98% pure by HPLC.

Recrystallization is accomplished using hot mixture of absolute ethanol and isopropanol (50/50 v/v). 30.0 g crude hydrobromide product is dissolved in a minimum amount of hot ethanol/isopropanol (about 45 mL). Gaseous HBr is carefully bubbled into the warm solvent solution until the solution is strongly acidic (pH<2.0, pH paper), and then continued for 1-2 minutes. Bubbling gaseous HBr into absolute ethanol is a strongly exothermic process. The covered flask is allowed to cool to room temperature over a period of about 3 hours. Beautiful white crystals form. The flask is then cooled overnight at 4° C. The white crystals are quickly filtered at ambient temperature using a sintered-glass filter, washed with 25 mL acetone/isopropanol (50/50 v/v) and then with pure acetone and diethyl ether. The product is dried in a vacuum oven overnight at 50° C. and stored over $P_2O_5$ in a glass desiccator. This recrystallization method produces 26.1 g (87% recrystallization yield) purified product with HPLC purity of 99-F % when initial purity is >95%.

EXAMPLE 11

N,N,N',N'-tetramethyl-N-(3-phosphonopropyl)-1,3-propanediammonium di-Inner salt (60, fw=252.38)

Method 11a: Preparation of N,N,N',N'-tetramethyl-N-(3-diethylphosphonopropyl)-1,3-propanediamine diethyl ester bromide•hydrobromide (79a, fw=470.24).

260.5 g freshly distilled N,N,N',N'-tetramethyl-1,3-propanediamine (2.0 mole, fw=130.24) and 520 mL acetone are placed in a 2 L flask that is equipped with a mechanical stirred and a thermometer. The temperature is maintained at about 45° C. A solution of 259.1 g diethyl 3-bromopropanephosphonate (1.0 mole, fw=259.09) in 260 mL acetone is slowly added over a period of about seven (7) hours to the stirring amine solution. A sticky, white crystalline solid or clear viscous oil comes out of solution several minutes into the reaction. The mixture is stirred overnight (18 hours) at room temperature and them cooled briefly to 4° C. Either the solid is filtered through sintered-glass or the reaction liquid is decanted from the viscous oil. The solvent can be removed from the filtrate solution or supernatant solution, and the excess, unreacted diamine can be recovered. The crude product is dissolved in a minimum amount of hot absolute ethanol (450-500 mL). The solution is filtered while hot, and gaseous HBr is very carefully bubbled into the mixture until the solution is slightly acidic (pH=4-5, pH paper). The solution is allowed to cool to room temperature, and then it is cooled to 4° C. and allowed to stand overnight. 400 mL cold acetone/diethyl ether (50/50 v/v) is added and the mixture is allowed to stand at 4° C. for three (3) more hours. The reaction mixture is quickly filtered at ambient temperature using a sintered-glass filter, and the solid mass is washed with diethyl ether. The deliquescent white solid is dried in a vacuum oven overnight at 50° C. and stored over $P_2O_5$ in a glass desiccator. This method produces about 430 g of crude product that is 94-98% pure by HPLC.

Method 11b 423.3 g of the above product (0.90 mole, fw=470.24) and 900 mL 37% hydrochloric acid are placed in a 1.7 Liter heavy-walled, glass pressure vessel that is equipped with a magnetic stirring-bar and a threaded Teflon cap. The mixture is heated to 80° C., stirred for about 21 hours, filtered through sintered-glass and cooled to room temperature. The solvent and volatile acid are removed under vacuum using a rotary evaporator. 800 mL absolute ethanol is added, and the mixture is briefly heated to near boiling with stirring and finally cooled to room temperature. The ethanol and other volatiles are completely removed again under vacuum. The pale yellow residue is dissolved in a minimum amount of hot absolute ethanol (400-500 mL), and then triethylamine is added dropwise with stirring until the pH of the solution is near neutral (pH=7.0, pH paper). The mixture is cooled to room temperature and then allowed to stand overnight (18 hours) at 4° C. A white crystalline solid forms. The white crystals are obtained by rapid filtration at ambient temperature using a sintered-glass filter and washed with acetone/diethyl ether (50/50 v/v). The product is initially dried by passing dry nitrogen through the filter bed and then dried in a vacuum oven overnight at 50° C. This hydrolysis method and crystallization produces about 202 g (89%) of purified product with HPLC purity of 98-99%.

Modifications: 48% aqueous HBr can be used instead of 37% HCl for hydrolysis of the phosphonate ester. This is a general method for preparation of phosphonoalkyl substituted amine-quat compounds. The use of the more expensive dibenzyl esters of phosphonic acids allows convenient removal of benzyl groups by mild catalytic hydrogenation.

EXAMPLE 12 (METHOD 12)

Preparation of N-(3-trimethylammoniumpropyl)-dimethylamine hydroxide (29d, fw=350.56)

108.6 g recrystallized N-(3-trimethylammoniumpropyl) dimethylamine chloride hydrochloride (500 mmole, 29a, fw=217.19) is dissolved in 425 mL degassed, deionized water under a $CO_2$-free, $N_2$ atmosphere in a glass-free, polypropylene flask. 117.0 g Silver oxide (505 mmole, fw=231.74) is added to the solution, and it is vigorously stirred with a mechanical polypropylene propeller at room temperature for 48 hours. The mixture is filtered through a polypropylene filter/felt in a polypropylene Buechner filter into a polypropylene receiving flask under a blanket of nitrogen gas. The water-clear solution is placed on a rotary evaporator, and the water is partially removed under vacuum over a period of 36-48 hours while the product (viscous liquid) is maintained at about 50° C. using an external heating bath. Acid-base titration (hydroxide) and HPLC analysis (cation) show the final solution to contain 36% of the quat hydroxide; titration shows residual $Ag^+$ and $Cl^-$ to be less than 10 ppm. The solution is stored at ambient temperature in a sealed, clean polypropylene container. Yield is nearly quantitative.

Modifications: This method is generally applicable to most amine-quat buffers described here. Generally, buffers that contain amide groups or 2-hydroxyethyl groups have limited stability under strongly basic conditions. These same buffer compounds as chloride/bromide salts are suitable for conversion to hydroxide salts using ion-exchange, electrolysis and electrodialysis methods.

EXAMPLE 13 (METHOD 13)

Preparation of Bis[N-(3-trimethylammoniumpropyl)-dimethylamine]carbonate (29e, fw=162.28)

108.6 g recrystallized N-(3-trimethylammoniumpropyl) dimethylamine chloride hydrochloride (500 mmole, fw=217.19) is dissolved in 425 mL degassed, deionized water under a $CO_2$-free, $N_2$ atmosphere in a glass-free, polypropylene flask. 139.0 g silver oxide (600 mmole, fw=231.74) is added to the solution, and it is vigorously stirred with a mechanical polypropylene propeller at room temperature for 48 hours. The mixture is filtered through a polypropylene filter/felt in a polypropylene Buechner filter into a polypropylene receiving flask under a blanket of nitrogen gas. $CO_2$ gas is slowly bubbled through the stirring filtrate to convert the hydroxide to the carbonate. A pH meter with a calibrated glass-electrode is used to periodically monitor the pH of the solution. The reaction is considered to be complete when the final pH is 11.9±0.1. At this pH, the reaction with carbon dioxide is much slower, because the reaction of carbonate with $CO_2$ is slow while the reaction of hydroxide with $CO_2$ is fast. This water-clear solution is placed on a rotary evaporator, and the water is partially removed under vacuum over a period of 36-48 hours while the product (viscous liquid) is maintained at about 50° C. using an external heating bath. Acid-Base titration (carbonate) and HPLC analysis (cation) show the final solution to contain 38% of the quat carbonate; atomic absorption shows residual $Ag^+$ and $Cl^-$ to be less than 1 ppm. The solution is stored at ambient temperature in a sealed, clean polypropylene container. Yield is nearly 100%.

EXAMPLE 14

Microbial Growth-Inhibition Assays

Microbial growth inhibition assays are carried out 96-well plates with well volume of 400 µL. In the present inventors' hands, data obtained in this manner are almost equivalent to that obtained in traditional shake flasks while data collection is more accurate and convenient. Two calibrated plate readers are used so that two plates, corresponding to a single organism, could be read at the same time. Each plate contains 80 cells for one organism and four buffers each at five concentrations (25, 50, 100, 225, 500 mM) with each buffer-concentration combination (20) being replicated four-fold. Each of these cells contained 50 µL of a fresh, calibrated cell culture plus 250 µL fresh sterile cell culture. In addition, each plate contained eight identical cells with 250 µL sterile, buffer-free growth medium plus 50 µL fresh cell culture and eight cells with 300 µL sterile growth medium and no organism. Microbial growth is measured by light-scattering/absorbance measurements at 600 nm every 15-60 minutes for the prescribed period. Every 15 minutes, each plate undergoes agitation/vibration which resuspends the organisms and promotes aeration; this process is repeated just prior to each absorbance reading. For each medium, six bottles of sterile media are prepared, one for each buffer concentration (0, 30, 60, 120, 270, 600 mM) so that when each is diluted in the plate, the desired concentrations will be obtained. The media components (see below), added buffer and water are mixed, and the pH is adjusted to the proper value. Each bottle of medium is heat sterilized (121° C., 15 psig, 20 minutes), cooled and, if necessary, the pH is readjusted to the proper value in a sterile fashion with 37% HCl or 50% NaOH.

Based upon prior experience with these organisms, a series of microbial growth measurements are carried out to determine optimal growth conditions. Four different media compositions unique to each organism each at four pH values (6.0, 6.5, 7.0, 7.5) are measured at three temperatures (23° C., 30° C., 37° C.). Fortunately, combinations of near optimal growth conditions have been found so that the same pH of 7.0±0.1 could be used for all four organisms that are listed below:

| Organism | ATCC Num. | Temp. (° C.) | pH | Time | Medium | Initial Culture (cfu/mL) |
|---|---|---|---|---|---|---|
| E. coli | ATCC 13525 | 37 ± 1 | 7.0 ± 0.1 | 36 hr. | TS broth | $1.7 \times 10^{10}$ |
| P. fluorescens | ATCC 19020 | 30 ± 1 | 7.0 ± 0.1 | 48 hr. | PM broth | $2.1 \times 10^{10}$ |
| Pichia pastoris | ATCC 20864 | 30 ± 1 | 7.0 ± 0.1 | 45 hr. | ME broth | $1.3 \times 10^{10}$ |
| S. cerevisiae | ATCC 18824 | 30 ± 1 | 7.0 ± 0.1 | 33 hr. | ME broth | $5.2 \times 10^{7}$ |

E. coli: Escherichia coli
P. fluorescens: Pseudomonas fluorescens
P. pastoris: Pichia pastoris (also called Komagataella pastoris)
S. cerevisiae: Saccharyomyces cerevisiae Compositions of growth media are listed below for one liter of medium. pH is adjusted to 7.0±0.1 both before and after heat sterilization. Similar growth results are obtained when the added cationic buffer is added before heat-sterilization and after heat-sterilization via sterile filtration. Several useful growth media containing methanol are known for Pichia, but ME broth is equally good under the current conditions, and then evaporation of methanol is not a problem. Amounts below are given as g/L in sterilized growth medium.
Modified ME broth: 15.0 g glucose
    5.0 g meat peptone
    20.0 g malt extract
    2.0 g $(NH_4)_2SO_4$
Modified TS broth: 2.5 g glucose
    17.0 g casein peptone
    3.0 g soy peptone
    5.0 g NaCl
    2.5 g $K_2HPO_4$
Modified PM broth: 2.5 g glucose
    10.0 g meat peptone
    10.0 g casein peptone
    10.0 g glycerin
    1.5 g $K_2HPO_4$
    0.5 g $NH_4Cl$
    0.5 g $MgSO_4.7H_2O$ The buffers in these tests are DEAGA, MEAGA, MOGA, DIMEGA, DEGA, TRIS, MES and TAPS. The structures of DEAGA, MEAGA, MOGA, DIMEGA and DEGA, all of which are within the scope of the present invention, are provided herein. TRIS, MES and TAPS are conventional buffers known in the art.

The bacterial and yeast strains are grown up and counted several times in each respective growth medium obtain fresh, stable, reproducible cultures of known density as a function of time. Microbial counting is carried out in the usual fashion by using serial dilutions followed by plate counting. Each culture is diluted and plated three times, and the values are averaged. When a culture reaches the proper microbial density (cfu/mL), two 96-well plates are quickly loaded as described above, and plate reading is started using two matched plate readers.

The growth results are shown in FIGS. 1-4, which are graphs depicting the comparative growth of four different species of microorganisms in growth media containing the above-identified buffers within and not within the scope of the present invention, at various buffer concentrations.

FIG. 1 is a graph depicting the growth of Escherichia coli in the presence of varying concentrations of buffers within the scope of the present invention, DEAGA, MEAGA, MOGA, DIMEGA and DEGA, and not within the scope of the present invention, TRIS, MES and TAPS.

Figure 2:
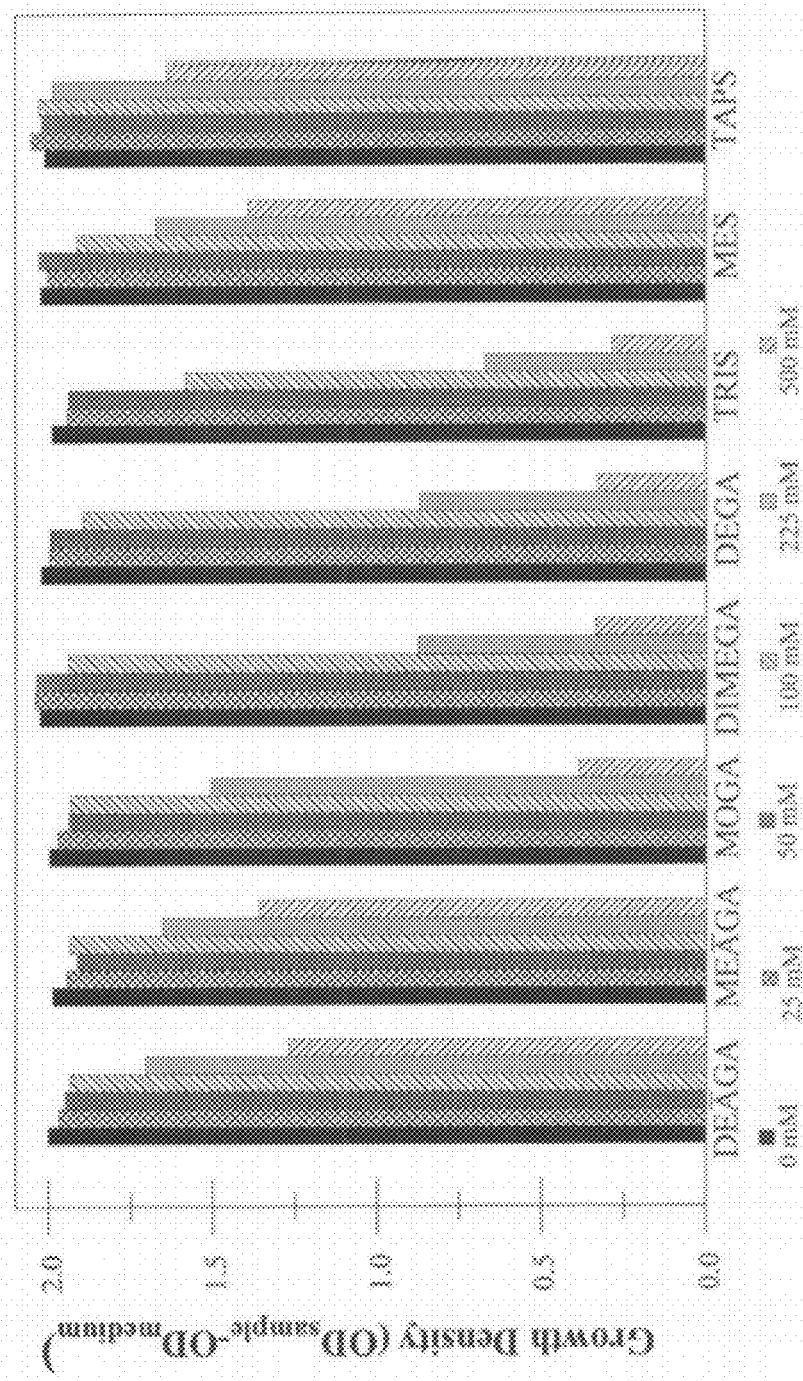

FIG. 2 is a graph depicting the growth of Pseudomonas fluorescens in the presence of varying concentrations of buffers within the scope of the present invention, DEAGA, MEAGA, MOGA, DIMEGA and DEGA, and not within the scope of the present invention, TRIS, MES and TAPS.

Figure 3:
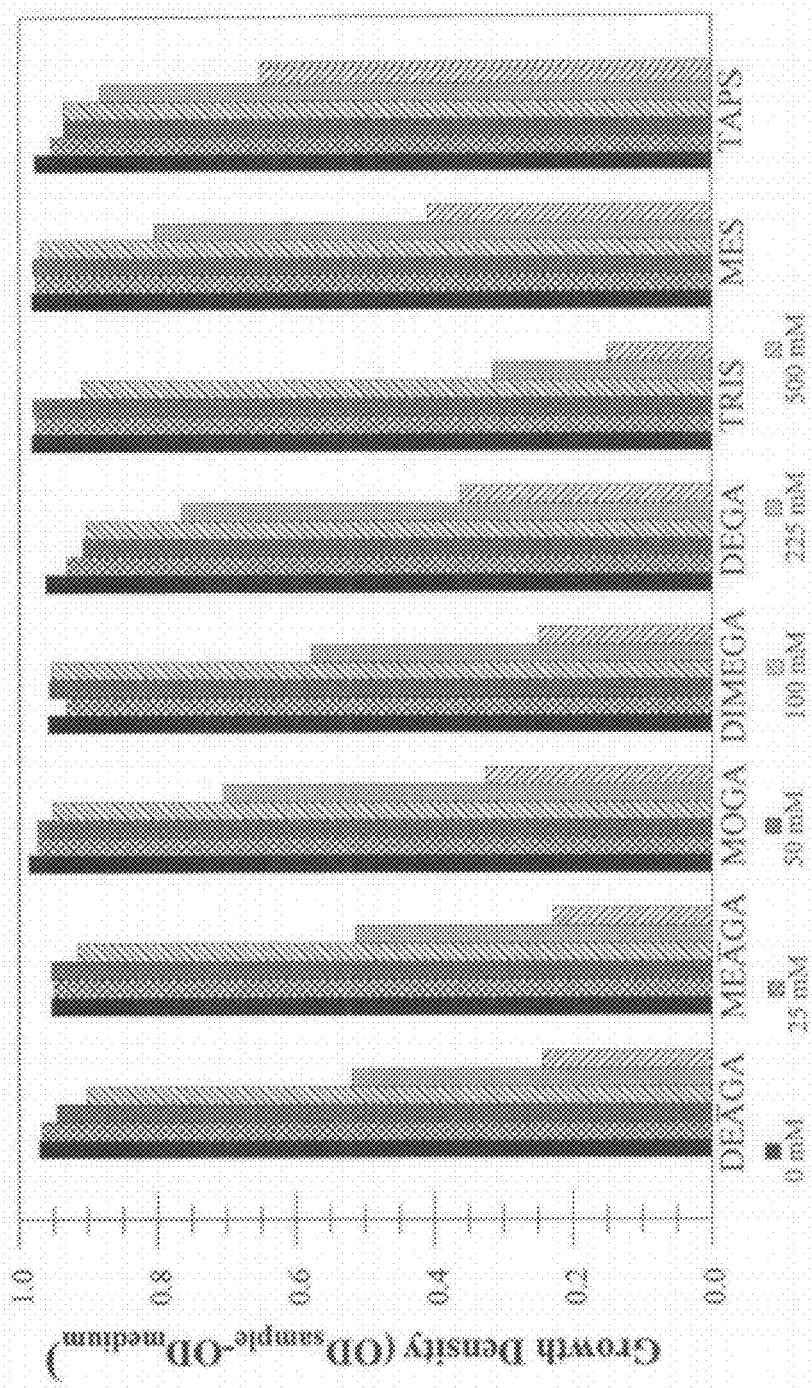

FIG. 3 is a graph depicting the growth of Pichia pastoris in the presence of varying concentrations of buffers within the scope of the present invention, DEAGA, MEAGA, MOGA, DIMEGA and DEGA, and not within the scope of the present invention, TRIS, MES and TAPS.

Figure 4:
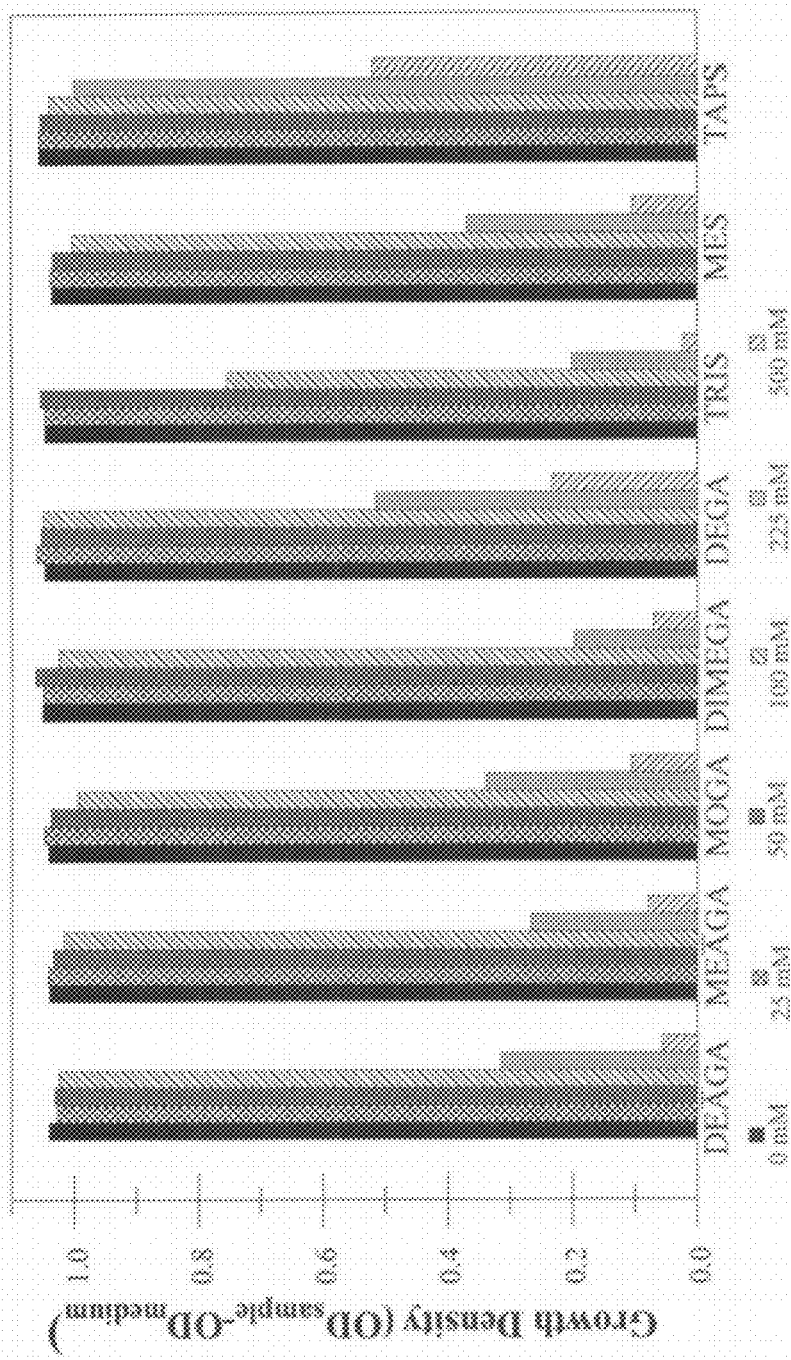

FIG. 4 is a graph depicting the growth of Saccharyomyces cerevisiae in the presence of varying concentrations of buffers within the scope of the present invention, DEAGA, MEAGA, MOGA, DIMEGA and DEGA, and not within the scope of the present invention, TRIS, MES and TAPS.

Caution must be exercised in the interpretation of comparative biological studies of this type. In this case, comparison of different buffers with different $pK_a$ values at the same pH means that some buffers are primarily in the basic form (MES, DEAGA), some are primarily in the acidic form (TAPS, DEGA) and some are in between. Furthermore, some buffers are cationic, some are anionic, some are neutral and some are neutral-zwitterionic. However, an even worse situation would arise by comparing the growth of same organism at various pH values each where $pH=pK_a$ for each respective buffer.

Bearing in mind the foregoing cautions, some useful generalizations about the microbial growth results can be made.

(a) There is no indication of acute toxicity for any of eight buffers (5 cationic) in any of the three growth media.

(b) The five cationic buffers are fully compatible with all three growth media with no evidence of precipitation, color formation or odor formation either before or after sterilization.

(c) The cationic buffers are tolerant to standard autoclaving conditions and to sterile filtration methods.

(d) Of the three standard buffers tested, growth inhibition at higher concentrations always follows the order TRIS>MES>TAPS with TAPS being consistently the best of all eight buffers tested.

(e) Escherichia is unique; there are small differences, but in general there is little growth inhibition by any buffer at any concentration.

(f) In contrast, Saccharyomyces is most sensitive to high concentrations of all buffers.

(g) All four organisms show that the five cationic buffers as a whole are similar to each other, being better than TRIS ($1^+$/0) and about the same as MES ($0/1^-$) and not a good as TAPS ($0/1^-$).

(h) All five cationic buffers show no significant growth inhibition for any of the organisms at concentrations of 100 mM or less.

(i) Pseudomonas shows significant discrimination between the cationic buffers: DEAGA and MEAGA are clearly better than DIMEGA and DEGA with MOGA being in between, and all 5 cationic buffers being better than TRIS.

(j) Comparison of buffers with similar $pK_a$ values shows no new trends, only reinforcement of trends already noted above: DEAGA (6.1) and MES (6.1) have about the same behavior, DIMEGA (7.9) is better than TRIS (8.1), TAPS (8.4) is better than DEGA (8.5).

EXAMPLE 15

Precision Measurements of $pK_a$-Values for pH-Buffers

High purity analytical quality reagents are used in these studies: potassium chloride, potassium hydroxide, primary standard potassium acid phthalate (KAP, Baker), 18 megohm deionized doubly-distilled water ($CO_2$-free). The buffers as hydrochloride or hydrobromide salts are carefully recrystallized from organic solvents that contained a small excess of gaseous hydrogen chloride or hydrogen bromide until the purity, as measured by HPLC, was 99.5% or greater. They are dried in a vacuum oven at 50° C. for 18-24 hours and stored in a glass desiccator over $P_2O_5$. The only remaining impurities are inert water/solvent and traces of residual HCl or HBr. Most buffers are stable in atmospheric air; a few are somewhat hygroscopic. During the weighing of the buffer compounds, care is taken to prevent or minimize absorption of atmospheric moisture. Solutions containing 10 mM buffer and 80 mM KCl are carefully prepared using degassed, deionized water and standardized volumetric flasks. Six independent pH titrations are carried out for each buffer compound using 100 mM carbonate-free KOH that is carefully standardized against KAP. Titrations are carried out using a Mettler-Toledo (Columbus, Ohio) Model T50 Automatic Titrator equipped with a 75 mL jacketed glass titration cell, Model DG-115-SC combination pH electrode (Ag/AgCl reference) and a precision 10 mL automatic burette.

The titrator is controlled and data collected by LabX Titration software, version 2.5. The titration cell is thermostatically controlled at 10.00±0.05° C., 25.00±0.05° C. or 40.00±0.05° C. Temperatures are measured using a NIST-traceable mercury thermometer. Titrations are adjusted so that the endpoint is close to 5 mL delivery point of the burette. Incremental titrations are carried out with increment volume of 100 μl and with continuous stirring; the system is allowed to settle after each incremental addition (10-30 sec) before a reading is recorded. Accurate, NIST-traceable buffers (±0.001 pH unit) with accurately known values at 2, 4, 7, 10, 12 in the temperature range 10-40° C. are used (Oakton Instruments, Vernon Hills, Ill.). The electrode is calibrated at pH=2, 4, 10 and 12. The pH=7 buffer is independently measured. If the pH=7 measurement is accurate to ±0.002 pH unit, a titration is carried out; if not, the calibration is repeated. A pH calibration is carried out before each titration experiment. For buffers with $pK_a$ values less than 3.5 or greater than 10.5, concentrations (buffer, KOH, KCl) were increased by 5-fold or 10-fold. Under these conditions, only one or two titrations were carried out, and the $pK_a$ value was estimated to ±0.2 logK unit. The experimental titrimetric data are analyzed using the PKAS software package of Martell and Motekaitis (Martell, A. E.; Motekaitis, R. J., Determination and Use of Stability Constants, 2nd ed., VCH Publishers, New York, 1992; ISBN 1-56081-5116-7.). An open source g77 Fortran compiler for Fortran 77 (downloaded from www.neng.usu/cee/faculty/gurro/Classes/ Classes_Fall2002/Fortran77/Fortran77Course.html) is used to run the PKAS software on a desktop PC computer. Data from each run are transferred (cut/paste) from the titrator software into a formatted Excel spreadsheet, and then transferred (cut/paste) in a properly formatted form into a data input file for PKAS. For every titration, the concentration of the buffer is refined as well as the amount of residual strong acid. In the $pK_a$ range 3.5-10.5, data points used in the $pK_a$ refinement are restricted to the 0.1-1.2 equivalence range when they are available. For selected compounds, accurate, fully refined $pK_a$ results with confidence limits are given below.

TABLE 2

Measured pH Values

| Buffer | Meas. $pK_a$ | Predicted $pK_a$ | Std Dev[c] | Avg GOF[b] | Sigma Range[b] | Buffer Conc. Multiplier | Resid.[a] $H^+$ |
|---|---|---|---|---|---|---|---|
| MOGA HCl | 5.597 | 5.6 | ±0.006 | ±0.002 | 0.3-0.6 | 0.967 | 0.03% |
| DEAGA HCl | 6.049 | 6.1 | ±0.007 | ±0.002 | 0.3-0.7 | 0.977 | 0.02% |
| MEAGA HCl | 7.097 | 7.0 | ±0.004 | ±0.008 | 1.0-1.7 | 0.984 | 0.02% |
| DIMEGA HCl | 7.894 | 7.9 | ±0.002 | ±0.002 | 0.2-0.4 | 0.994 | 0.07% |
| PIGA HCl | 8.277 | 8.3 | ±0.004 | ±0.009 | 0.8-1.0 | 0.944 | 0.04% |
| DEGA HCl | 8.467 | 8.5 | ±0.002 | ±0.002 | 0.2-0.4 | 0.983 | 0.03% |
| Carnitine HCl | 3.825 | 3.8 | ±0.005 | ±0.003 | 0.5-0.8 | 0.985 | 0.02% |
| MES | 6.088 | 6.1[d] | ±0.005 | ±0.003 | 0.6-0.9 | 0.996 | <0.01% |
| MOPS | 7.099 | 7.0[d] | ±0.003 | ±0.003 | 0.6-1.2 | 0.999 | <0.01% |
| TAPS | 8.410 | — | ±0.002 | ±0.003 | 0.7-0.8 | 0.998 | <0.01% |

[a]100 * (moles of excess $H^+$)/(moles of buffer
[b]See ref. 3; GOF = Goodness-Of-Fit
[c]Calc. from six repeated experiments
[d]add 0.2 because no quat

EXAMPLE 16

Approximate Measurements of $pK_a$-Values for pH Buffers

This method is used when nonreactive impurities are >5% (HPLC), when reactive impurities are >1% (HPLC), when insufficient buffer is available or when noticeably poor curve fitting is seen in the above method. The experimental method is nearly the same as the above method, but the experimental volume-pH data are processed differently. Usually, only one or two titrations are carried out. The $pK_a$ is estimated to be the same as the pH of the titration curve at the half-equivalence point. The estimated $pK_a$ values can be as good at ±0.1 or as poor as ±0.5 depending on the nature and amounts of impurities.

EXAMPLE 17

HPLC Analysis of Buffer Purity

Method 17a—Weak Mixed-Mode—Cation Exchange-Reversed Phase: Purity analyses were carried out using Waters Corp. (Milford, Mass.) gradient HPLC equipped with a Waters 996 PDA detector in tandem with a Dionex/ESA Biosciences (Chelmsford, Mass.) Corona Plus CAD detector and a 5 µm, 100 Å, 4.6×150 mm PrimeSep 200 mixed-mode chromatography column (SIELC Technologies, Prospect Heights, Ill.). Cationic buffers and most of their impurities have little UV absorption so the CAD detector is needed; however, bromide anion and some buffer impurities absorb in UV.

---

Sample Injection: 5 µL of 5 mg/mL sample solution in A buffer
Flow-Rate: 1.0 mL/min.
A buffer: 95% H$_2$0 + 5% CH$_3$CN (v/v) with 0.2% (v/v) trifluoroacetic acid.
B buffer: 25% H$_2$0 + 75% CH$_3$CN (v/v) with 0.2% (v/v) trifluoroacetic acid.
Gradient Method:   100% A                     0-1 min
                   100% A to 50% A/50% B      1-21 min
                   50% A/50% B                21-26 min
                   50% A/50% B to 100% B      26-27 min
                   100% B                     27-30 min

---

Method 17b—Strong Mixed-Mode—Cation Exchange-Reversed Phase: Purity analyses were carried out using Waters Corp. (Milford, Mass.) gradient HPLC equipped with a Waters 996 PDA detector in tandem with a Dionex/ESA Biosciences (Chelmsford, Mass.) Corona Plus CAD detector and a 5 µm, 100 Å, 4.6×150 mm PrimeSep A mixed-mode chromatography column (SIELC Technologies, Prospect Heights, Ill.).

---

Sample Injection: 5 µL of 5 mg/mL sample solution in A buffer
Flow-Rate: 1.0 mL/min.
A buffer: 100% H$_2$0 + 0% CH$_3$CN (v/v) with 0.2% (v/v) trifluoroacetic acid.
B buffer: 25% H$_2$0 + 75% CH$_3$CN (v/v) with 0.2% (v/v) trifluoroacetic acid.
Gradient Method:   100% A                0-1 min
                   100% A to 100% B      1-21 min
                   100% B                21-26 min

---

Method 17c—HILIC: Purity analyses were carried out using Waters Corp. (Milford, Mass.) gradient HPLC equipped with a Waters 996 PDA detector in tandem with a Dionex/ESA Biosciences (Chelmsford, Mass.) Corona Plus CAD detector and a 5 µm, 100 Å, 4.6×250 mm Obelisc N chromatography column (SIELC Technologies, Prospect Hts., Ill.).

---

Sample Injection: 5 µL of 5 mg/mL sample solution in A buffer
Flow-Rate: 1.0 mL/min.
A buffer: 25% H$_2$0 + 75% CH$_3$CN (v/v) with 0.1% (v/v) trifluoroacetic acid.
B buffer: 70% H$_2$0 + 30% CH$_3$CN (v/v) with 0.1% (v/v) trifluoroacetic acid.
Gradient Method:   100% A               0-10 min
                   100% A to 100% B     10-20 min
                   100% B               20-25 min

---

Structures and names of exemplary buffer compounds in accordance with various embodiments of the present invention are shown on the following pages. All of the buffer compounds are identified by name and some are identified by a compound number and an acronym, the acronym created in accordance with common practices in the buffer art.

Exemplary reactions and compounds in accordance with various embodiments of the present invention are shown in Table 1 below. The compound numbers in Table 1 correspond to the compound numbers in the preceding pages showing the structures and names of the compounds. The Method numbers correspond to the Examples having the same number.

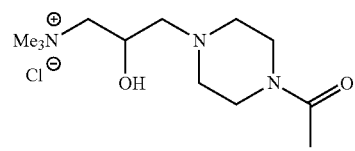

40

APAGA
N-(2-Hydroxy-3-trimethylammonium-propyl)-N'-acetylpiperazine Chloride

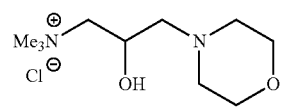

1

MOGA
N-(2-Hydroxy-3-trimethylammonium-propyl)morpholine Chloride

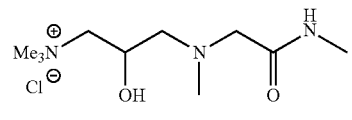

41

MAGGA
N-(2-Hydroxy-3-trimethylammonium-propyl)-N,N'-dimethylglycinamide Chloride

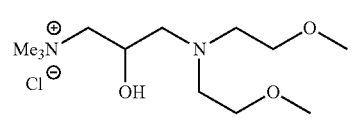

2

BIMEGA
N-(2-Hydroxy-3-trimethylammonium-propyl)-bis(2-methoxyethyl)amine Chloride

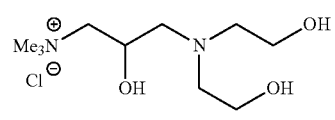

3

DEAGA
N-(2-Hydroxy-3-trimethylammonium-propyl)diethanolamine Chloride

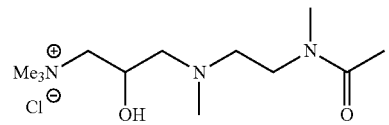

42

DIMAEGA
N-(2-Hydroxy-3-trimethylammonium-propyl)-N,N'-dimethyl-N'-acetyl-ethylenediamine Chloride

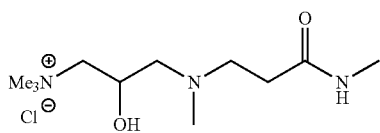

MALAGA
N-(2-Hydroxy-3-trimethylammonium-
propyl)-N,N'-dimethyl-β-alanamide
Chloride

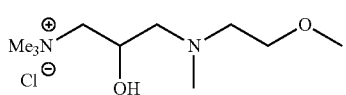

MEMGA
N-(2-Hydroxy-3-trimethylammonium-
propyl)-N-methyl-2-methoxyethylamine
Chloride

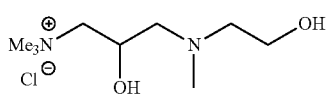

MEAGA
N-(2-Hydroxy-3-
trimethylammonium-
propyl)-N-methylethanolamine Chloride

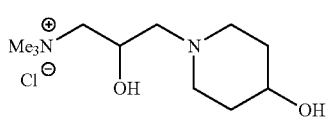

OPIGA
N-(2-Hydroxy-3-
trimethylammonium-
propyl)piperidine Chloride

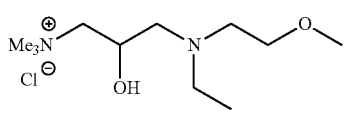

MEEGA
N-(2-Hydroxy-3-trimethylammonium-
propyl)-N-ethyl-2-methoxyethylamine
Chloride

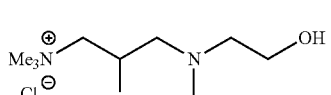

TEAGA
N-(2-Hydroxy-3-trimethylammonium-
propyl)-N-ethylethanolamine Chloride

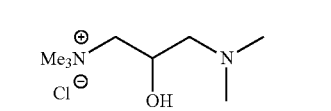

DIMEGA
N-(2-Hydroxy-3-trimethylammonium-
propyl)dimethylamine Chloride

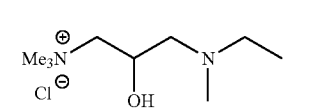

EMGA
N-(2-Hydroxy-3-trimethylammonium-
propyl)dimethylamine Chloride

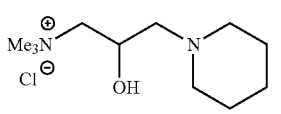

PIGA
N-(2-Hydroxy-3-trimethylammonium-
propyl)piperidine Chloride

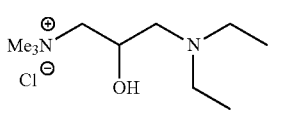

DEGA
N-(2-Hydroxy-3-trimethylammonium-
propyl)diethylamine Chloride

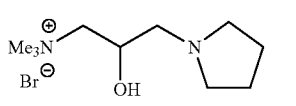

PYRGA
N-(3-Trimethylammoniumpropyl)
pyrrolidine Bromide

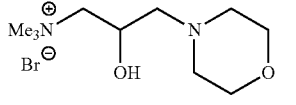

MOPA
N-(3-Trimethylammoniumpropyl)
morpholine Bromide

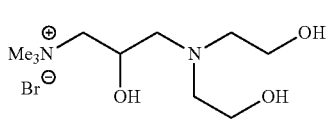

DEAPA
N-(3-Trimethylammoniumpropyl)-
diethanolamine Bromide

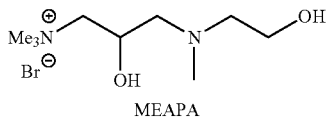

MEAPA
N-(3-Trimethylammoniumpropyl)-
N-methylethanolamine Bromide

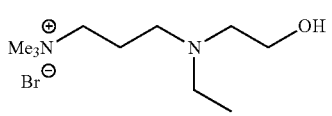

TEAPA
N-(3-Trimethylammoniumpropyl)-
N-ethylethanolamine Bromide

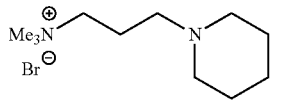

PIPA
N-(3-Trimethylammoniumpropyl)-
piperidine Bromide

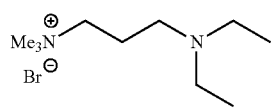

DEPA
N-(3-Trimethylammoniumpropyl)-
diethylamine Bromide

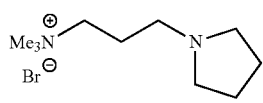

PYRPA
N-(3-Trimethylammoniumpropyl)-
pyrrolidine Bromide

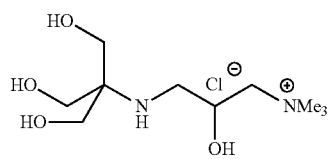

TRIGA
N-(2-Hydroxy-3-trimethylammonium-
propyl)-tris(hydroxymethyl)-
aminomethane Chloride

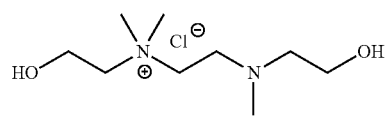

TIMDOD
3,3,6-Trimethyl-3,6-diazaoctane-1,8-diol Chloride

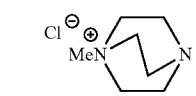

MEDBOC
N-Methyldiazobicyclooctane
Chloride

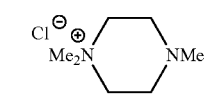

TIMEP
1,1,4-Trimethylpiperazinium
Chloride

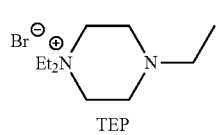

TEP
1,1,4-Triethylpiperazinium
Bromide

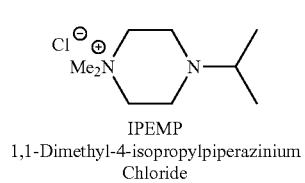

IPEMP
1,1-Dimethyl-4-isopropylpiperazinium
Chloride

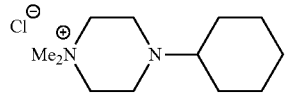

CHEMP
1,1-Dimethyl-4-cyclohexylpiperazinium
Chloride

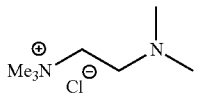

DIMEQ
N-(2-Trimethylammonium-ethyl)-
dimethylamine Chloride

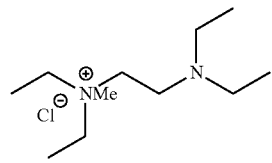

TEEQ
N-(2-Diethylmethylammonium-ethyl)-
diethylamine Chloride

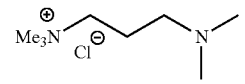

DIMEPA
N-(3-Trimethylammoniumpropyl)-
dimethylamine Chloride

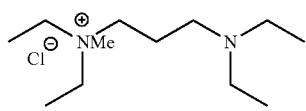

TEPA
N-(3-Diethylmethylammoniumpropyl)-
diethylamine Chloride

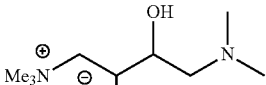

TEMBOQ
N-(4-Trimethylammonium-2,3-dihydroxy-
butyl)dimethylamine Chloride

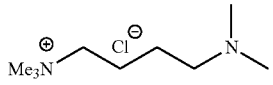

DIMEBA
N-(4-Trimethylammoniumbutyl)-
dimethylamine Chloride

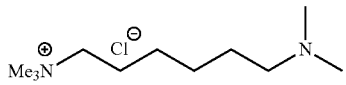

DIMEXAN
N-(6-Trimethylammoniumhexyl)-
dimethylamine Chloride

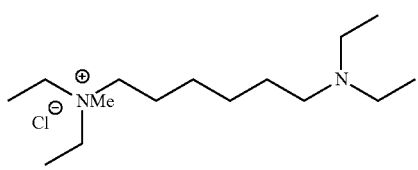

TEXA
N-(6-Diethylmethylammoniumhexyl)
diethylamine Chloride

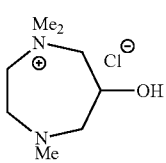

TIMOHOP
1,1,4-Trimethyl-6-hydroxy-
homopiperazinium Chloride

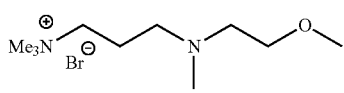

MEMPA
N-(3-Trimethylammoniumpropyl)-
N-methyl-2-methoxyethylamine
Bromide

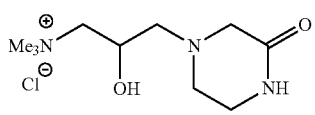

OPAGA
N-(2-Hyroxy-3-trimethylammonium-
propyl)-ketopiperazine Chloride

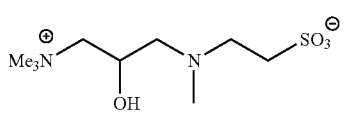

N-(2-Hydroxy-3-
trimethylammonium-
propyl)-N-methyltaurine

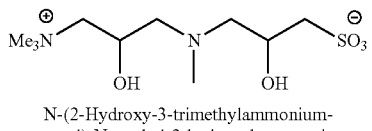

N-(2-Hydroxy-3-trimethylammonium-
propyl)-N-methyl-2-hydroxyhomotaurine

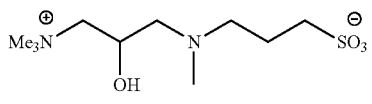

N-(2-Hydroxy-3-trimethylammonium-
propyl)-N-methylhomotaurine

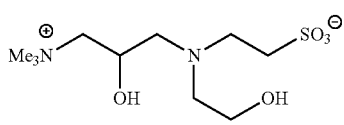

N-(2-Hydroxy-3-trimethylammonium-
propyl)-N-(2-hydroxyethyl)taurine

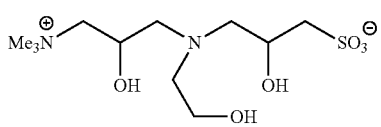

N-(2-Hydroxy-3-trimethylammoniumpropyl)-
N-(2-hydroxyethyl)-2-hydroxyhomotaurine

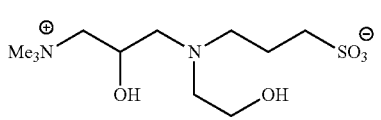

N-(2-Hydroxy-3-trimethylammonium-
propyl)-N-(2-hydroxyethyl)homotaurine

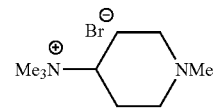

TEMAP
4-(Trimethylammonium)-
1-methylpiperidine Bromide

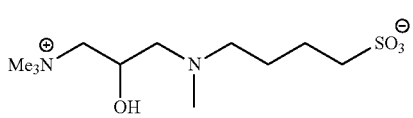

N-(2-Hydroxy-3-trimethylammonium-
propyl)-N-(4-sulfoethyl)methylamine

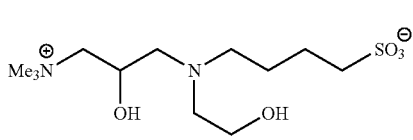

N-(2-Hydroxy-3-trimethylammonium-
propyl)-N-(4-sulfobutyl)ethanolamine

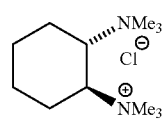

PEMDAC
trans-1-Dimethylamino-2-trimethyl-
ammoniumcyclohexane Chloride

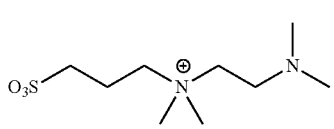

N,N,N',N'-Tetramethyl-N-(3-sulfo-
propyl)ethylenediamine Inner Salt

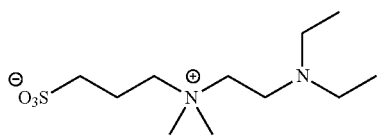

N,N',-Diethyl-N,N'-dimethyl-N-(3-sulfo-
propyl)ethylenediamine Inner Salt

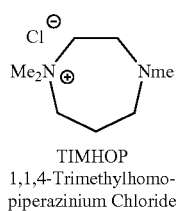

TIMHOP
1,1,4-Trimethylhomo-
piperazinium Chloride

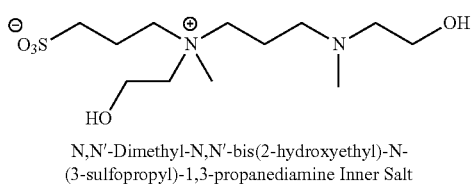

N,N'-Dimethyl-N,N'-bis(2-hydroxyethyl)-N-
(3-sulfopropyl)-1,3-propanediamine Inner Salt

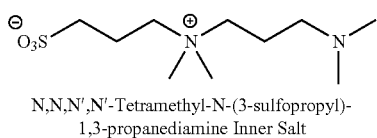

N,N,N',N'-Tetramethyl-N-(3-sulfopropyl)-
1,3-propanediamine Inner Salt

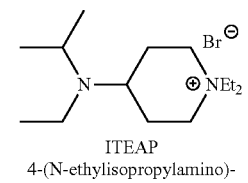

ITEAP
4-(N-ethylisopropylamino)-
1,1-diethylpiperidinium Bromide

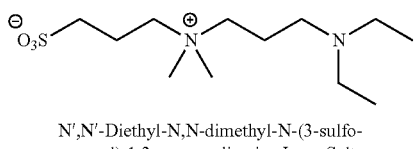

N',N'-Diethyl-N,N-dimethyl-N-(3-sulfo-
propyl)-1,3-propanediamine Inner Salt

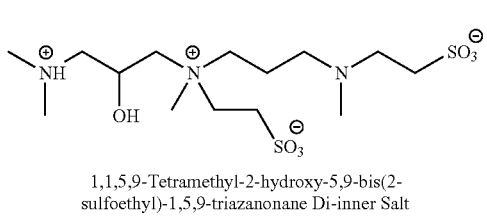

1,1,5,9-Tetramethyl-2-hydroxy-5,9-bis(2-
sulfoethyl)-1,5,9-triazanonane Di-inner Salt

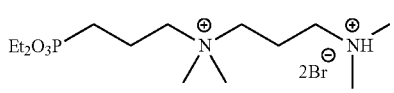

N,N,N',N'-Tetramethyl-N-(3-diethylphosphono-
propyl)-1,3-propanediammonium Dibromide

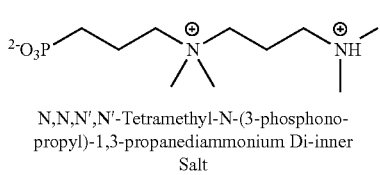

N,N,N',N'-Tetramethyl-N-(3-phosphono-
propyl)-1,3-propanediammonium Di-inner
Salt

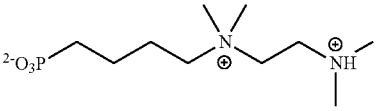

N,N,N',N'-Tetramethyl-N-(4-phosphono-
butyl)ethylenediammonium Di-inner Salt

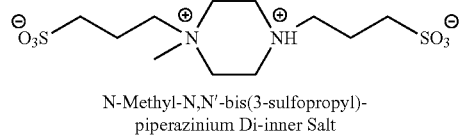

N-Methyl-N,N'-bis(3-sulfopropyl)-
piperazinium Di-inner Salt

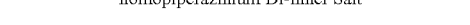

N-Methyl-N,N'-bis(3-sulfopropyl)-
homopiperazinium Di-inner Salt

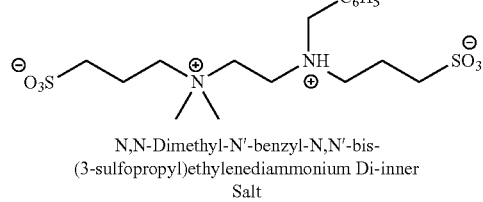

N,N-Dimethyl-N'-benzyl-N,N'-bis-
(3-sulfopropyl)ethylenediammonium Di-inner
Salt

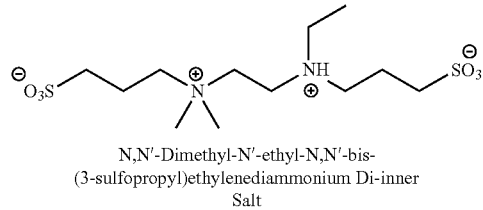

N,N'-Dimethyl-N'-ethyl-N,N'-bis-
(3-sulfopropyl)ethylenediammonium Di-inner
Salt

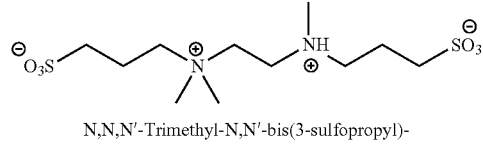

N,N,N'-Trimethyl-N,N'-bis(3-sulfopropyl)-
ethylenediammonium Di-inner Salt

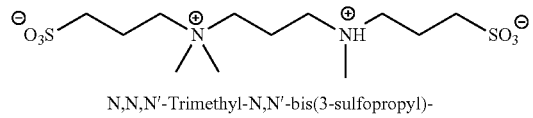

N,N,N'-Trimethyl-N,N'-bis(3-sulfopropyl)-
1,3-propanediammonium Di-inner Salt

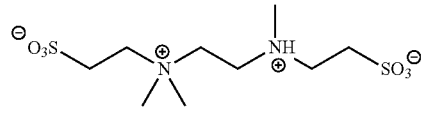

N,N,N'-Trimethyl-N,N'-bis(2-sulfoethyl)-
ethylenediammonium Di-inner Salt

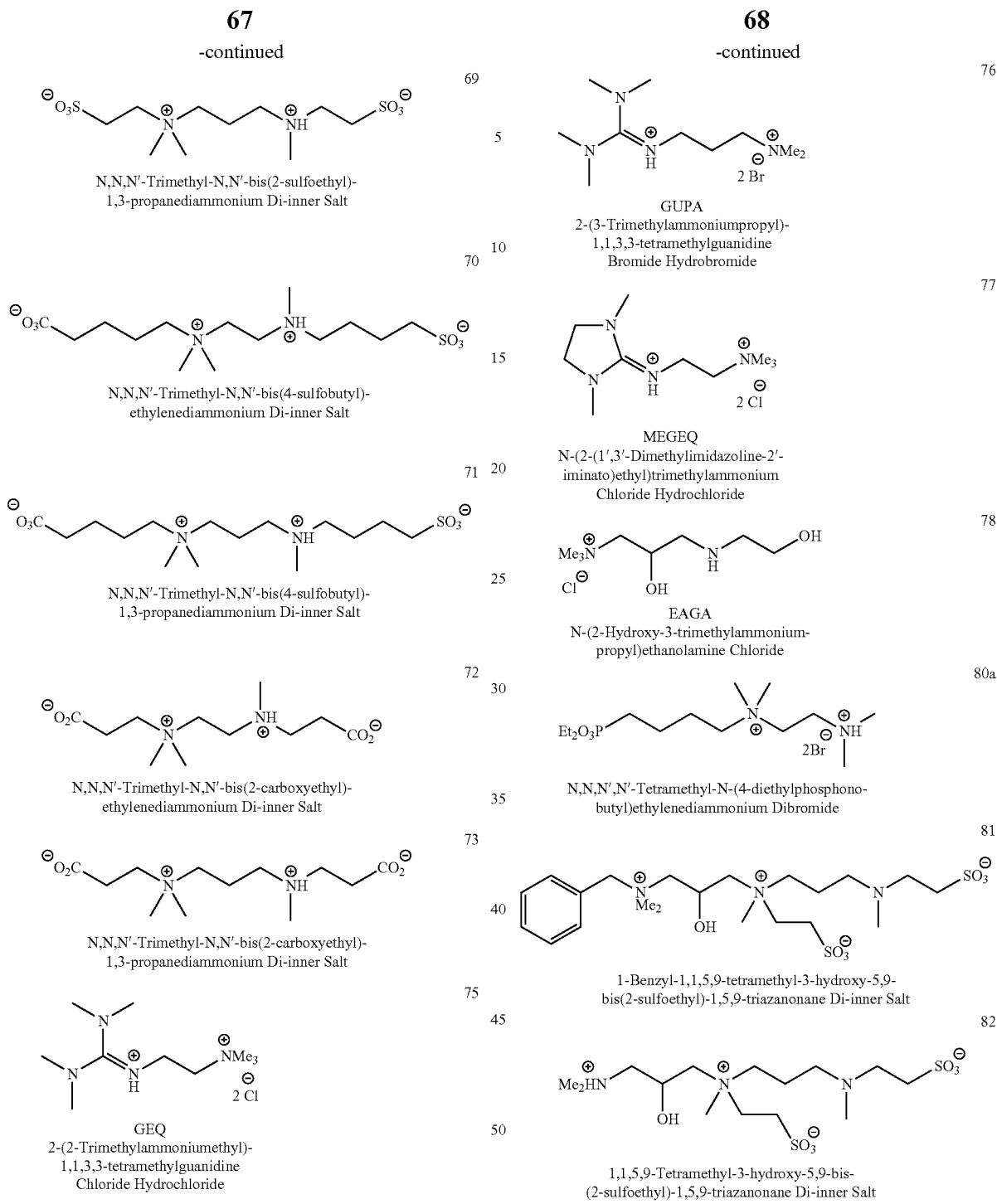
TABLE 1
Reactions and Compounds
| Cmpd | Method | Amine | Alkylating Agent | Est. pK$_a$ | Chemical Formula | Molecular Weight |
|---|---|---|---|---|---|---|
| 1 | 4 | Morpholine [110-91-8] | gmac | — | C$_{10}$H$_{23}$N$_2$O$_2$Cl | 238.76 |
| 1a | | 1•HCl | | ~5.6 | C$_{10}$H$_{24}$N$_2$O$_2$Cl$_2$ | 275.22 |
| 2 | 4 | Bis(2-methoxyethyl)amine [111-95-5] | gmac | — | C$_{12}$H$_{28}$N$_2$O$_3$Cl | 283.83 |
| 2a | | 2•HCl | | ~5.9 | C$_{12}$H$_{29}$N$_2$O$_3$Cl$_2$ | 320.29 |
| 3 | 4 | Diethanolamine [111-42-2] | gmac | — | C$_{10}$H$_{25}$N$_2$O$_3$Cl | 256.78 |
| 3a | | 3•HCl | | ~6.1 | C$_{10}$H$_{26}$N$_2$O$_3$Cl$_2$ | 293.24 |

TABLE 1-continued

Reactions and Compounds

| Cmpd | Method | Amine | Alkylating Agent | Est. p$K_a$ | Chemical Formula | Molecular Weight |
|---|---|---|---|---|---|---|
| 4 | 4 | N-Methyl(2-methoxyethyl)amine [38256-93-8] | gmac | — | $C_{10}H_{25}N_2O_2Cl$ | 240.78 |
| 4a | | 4•HCl | | ~7.0 | $C_{10}H_{26}N_2O_2Cl_2$ | 277.24 |
| 5 | 4 | N-Methylethanolamine [109-83-1] | gmac | — | $C_9H_{23}N_2O_2Cl$ | 226.75 |
| 5a | | 5•HCl | | ~7.1 | $C_9H_{24}N_2O_2Cl_2$ | 263.21 |
| 6 | 4 | N-Ethyl-2-methoxyethylamine [34322-82-2] | gmac | — | $C_{11}H_{27}N_2O_2Cl$ | 254.81 |
| 6a | | 6•HCl | | ~7.3 | $C_{11}H_{28}N_2O_2Cl_2$ | 291.27 |
| 7 | 4 | N-Ethylethanolamine [110-73-6] | gmac | — | $C_{10}H_{25}N_2O_2Cl$ | 240.78 |
| 7a | | 7•HCl | | ~7.4 | $C_{10}H_{26}N_2O_2Cl_2$ | 277.24 |
| 8 | 4 | Dimethylamine [124-40-3] | gmac | — | $C_8H_{21}N_2OCl$ | 196.73 |
| 8a | | 8•HCl | | ~7.9 | $C_8H_{22}N_2OCl_2$ | 233.19 |
| 8 | 5 | N,N,N',N'-Tetramethyl-2-hydroxy-1,3-diaminopropane [5866-51-8] | $CH_3Cl$ | — | $C_8H_{21}N_2OCl$ | 196.73 |
| 9 | 4 | Piperidine [110-89-4] | gmac | — | $C_{11}H_{25}N_2OCl$ | 236.79 |
| 9a | | 9•HCl | | ~8.3 | $C_{11}H_{26}N_2OCl_2$ | 273.25 |
| 10 | 4 | Diethylamine [109-89-7] | gmac | — | $C_{10}H_{25}N_2OCl$ | 224.78 |
| 10a | | 10•HCl | | ~8.5 | $C_{10}H_{26}N_2OCl_2$ | 261.24 |
| 11 | 4 | Pyrrolidine [123-75-1] | gmac | — | $C_{10}H_{23}N_2OCl$ | 222.76 |
| 11a | | 11•HCl | | ~8.7 | $C_{10}H_{24}N_2OCl_2$ | 259.22 |
| 12 | 10 | Morpholine [110-91-8] | bptab | — | $C_{10}H_{23}N_2OBr$ | 267.22 |
| 12a | | 12•HBr | | ~5.8 | $C_{10}H_{24}N_2OBr_2$ | 348.13 |
| 13 | 10 | Diethanolamine [111-42-2] | bptab | — | $C_{10}H_{25}N_2O_2Br$ | 285.23 |
| 13a | | 13•HBr | | ~6.3 | $C_{10}H_{26}N_2O_2Br_2$ | 366.14 |
| 14 | 10 | N-Methylethanolamine [109-83-1] | bptab | — | $C_9H_{23}N_2OBr$ | 255.20 |
| 14a | | 14•HBr | | ~7.3 | $C_9H_{24}N_2OBr_2$ | 336.12 |
| 15 | 10 | N-Ethylethanolamine [110-73-6] | bptab | — | $C_{10}H_{25}N_2OBr$ | 269.23 |
| 15a | | 15•HBr | | ~7.6 | $C_{10}H_{26}N_2OBr_2$ | 350.14 |
| 16 | 10 | Piperidine [110-89-4] | bptab | — | $C_{11}H_{25}N_2Br$ | 281.24 |
| 16a | | 16•HBr | | ~8.5 | $C_{11}H_{26}N_2Br_2$ | 362.15 |
| 17 | 10 | Diethylamine [109-89-7] | bptab | — | $C_{10}H_{25}N_2Br$ | 253.23 |
| 17a | | 17•HBr | | ~8.7 | $C_{10}H_{26}N_2Br_2$ | 334.14 |
| 18 | 10 | Pyrrolidine [123-75-1] | bptab | — | $C_{10}H_{23}N_2Br$ | 251.21 |
| 18a | | 18•HBr | | ~8.9 | $C_{10}H_{24}N_2Br_2$ | 332.13 |
| 19 | 4 | Tris(hydroxymethyl)aminomethane [77-86-1] | gmac | — | $C_{10}H_{25}N_2O_4Cl$ | 272.77 |
| 19a | | 19•HCl | | ~5.8 | $C_{10}H_{26}N_2O_4Cl_2$ | 309.24 |
| 20 | 5 | N,N'-Dimethyl-N,N'-bis(2-hydroxyethyl)ethylenediamine [14037-83-3] | $CH_3Cl$ | — | $C_9H_{23}N_2O_2Cl$ | 271.20 |
| 20a | | 20•HCl | | ~5.2 | $C_9H_{24}N_2O_2Cl_2$ | 352.12 |
| 21 | 5 | 1,4-Diazabicyclo[2.2.2]octane [280-57-9] | $CH_3Cl$ | — | $C_6H_{15}N_2Cl$ | 150.66 |
| 21a | | 21•HCl | | ~3.1 | $C_6H_{16}N_2Cl_2$ | 187.12 |
| 22 | 5 | 1,4-Dimethylpiperazine [106-58-1] | $CH_3Cl$ | — | $C_7H_{17}N_2Cl$ | 164.68 |
| 22a | | 22•HCl | | ~4.3 | $C_7H_{18}N_2Cl_2$ | 201.14 |
| 23 | 5 | 1,4-Diethylpiperazine [6483-50-7] | $C_2H_5Br$ | — | $C_{10}H_{23}N_2Br$ | 164.68 |
| 23a | | 23•HBr | | ~4.6 | $C_{10}H_{24}N_2Br_2$ | 201.14 |
| 24 | 5 | 1-Methyl-4-isopropylpiperazine [13480-33-6] | $CH_3Cl$ | — | $C_9H_{21}N_2Cl$ | 164.68 |
| 24a | | 24•HCl | | ~5.0 | $C_9H_{22}N_2Cl_2$ | 201.14 |
| 25 | 5 | 1-Methyl-4-cyclohexylpiperazine [7560-86-3] | $CH_3Cl$ | — | $C_{12}H_{25}N_2Cl$ | 232.80 |
| 25a | | 25•HCl | | ~5.2 | $C_{12}H_{26}N_2Cl_2$ | 269.26 |
| 26 | 5/8c$^a$ | 4-(dimethylamino)-1-benzylpiperidine [64168-08-7] | $CH_3Br$ (2 eq) | — | $C_9H_{21}N_2Br$ | 237.19 |
| 26a | | 26•HBr | | ~6.2 | $C_9H_{22}N_2Br_2$ | 318.11 |
| 27 | 5 | N,N,N',N'-Tetramethylethylenediamine [110-18-9] | $CH_3Cl$ | — | $C_7H_{19}N_2Cl$ | 166.70 |
| 27a | | 27•HCl | | ~6.1 | $C_7H_{20}N_2Cl_2$ | 203.16 |
| 27b | 12 | 27 as the hydroxide salt | | — | $C_7H_{20}N_2O$ | 148.25 |
| 27c | 13 | 27 as the hemicarbonate salt | | — | $C_{15}H_{38}N_4O_3$ | 322.50 |
| 28 | 5 | N,N,N',N'-Tetraethylethylenediamine [150-77-6] | $CH_3Cl$ | — | $C_{11}H_{27}N_2Cl$ | 222.81 |
| 28a | | 28•HCl | | ~6.7 | $C_{11}H_{28}N_2Cl_2$ | 259.27 |
| 29 | 5 | N,N,N',N'-Tetramethyl-1,3-diaminopropane [110-95-2] | $CH_3Cl$ | — | $C_8H_{21}N_2Cl$ | 180.73 |
| 29a | | 29•HCl | | ~8.1 | $C_8H_{22}N_2Cl_2$ | 217.19 |
| 29b | 10 | Dimethylamine [124-40-3] | bptab | — | $C_8H_{21}N_2Br$ | 225.18 |
| 29c | | 29b•HBr | | ~8.1 | $C_8H_{22}N_2Br_2$ | 306.09 |
| 29a | 9 | N-(3-Aminopropyl)trimethylammonium chloride [19223-69-9] | fo + fa (xs) | ~8.1 | $C_8H_{22}N_2Cl_2$ | 217.19 |
| 29d | 12 | 29 as hydroxide salt | | — | $C_8H_{22}N_2O$ | 162.28 |
| 29e | 13 | 29 as hemicarbonate salt | | — | $C_{17}H_{42}N_4O_3$ | 350.56 |
| 30 | 5 | N,N,N',N'-Tetraethyl-1,3-diaminopropane [60558-96-5] | $CH_3Cl$ | — | $C_{12}H_{29}N_2Cl$ | 236.84 |
| 30a | | 30•HCl | | ~8.7 | $C_{12}H_{30}N_2Cl_2$ | 273.30 |
| 31 | 5 | N,N,N',N'-Tetramethyl-1,4-diamino-2,3-dihydroxybutane [84808-89-9] | $CH_3Cl$ | — | $C_9H_{23}N_2O_2Cl$ | 271.20 |
| 31a | | 31•HCl | | ~8.7 | $C_9H_{24}N_2O_2Cl_2$ | 352.12 |
| 32 | 5 | N,N,N',N'-Tetramethyl-1,4-diaminobutane [111-51-3] | $CH_3Cl$ | — | $C_9H_{23}N_2Cl$ | 239.20 |
| 32a | | 32•HCl | | ~8.9 | $C_9H_{24}N_2Cl_2$ | 320.12 |
| 33 | 5 | N,N,N',N'-Tetramethyl-1,6-diaminohexane [111-18-2] | $CH_3Cl$ | — | $C_{11}H_{27}N_2Cl$ | 267.26 |
| 33a | | 33•HCl | | ~9.5 | $C_{11}H_{28}N_2Cl_2$ | 348.17 |
| 34 | 5 | N,N,N',N'-Tetraethyl-1,6-hexanediamine [7136-51-8] | $CH_3Cl$ | — | $C_{15}H_{35}N_2Cl$ | 323.37 |
| 34a | | 34•HCl | | ~10.1 | $C_{15}H_{36}N_2Cl_2$ | 404.28 |
| 35 | 5 | trans-1,2-bis(dimethylamino)cyclohexane [53152-69-5] | $CH_3Cl$ | — | $C_{11}H_{25}N_2Cl$ | 220.79 |

TABLE 1-continued

Reactions and Compounds

| Cmpd | Method | Amine | Alkylating Agent | Est. pK$_a$ | Chemical Formula | Molecular Weight |
|---|---|---|---|---|---|---|
| 35a | | 35•HCl | | ~3.8 | C$_{11}$H$_{26}$N$_2$Cl$_2$ | 257.25 |
| 36 | 5 | 1,4-Dimethylhomopiperazine [61134-91-6] | CH$_3$Cl | — | C$_8$H$_{19}$N$_2$Cl | 178.71 |
| 36a | | 36•HCl | | ~6.2 | C$_8$H$_{20}$N$_2$Cl$_2$ | 215.17 |
| 37 | 5 | 1,4-Dimethyl-6-hydroxyhomopiperazine [33468-98-3] | CH$_3$Cl | — | C$_8$H$_{19}$N$_2$OCl | 194.71 |
| 37a | | 37•HCl | | ~5.8 | C$_8$H$_{20}$N$_2$OCl$_2$ | 231.17 |
| 38 | 10 | N-Methyl(2-methoxyethyl)amine [38256-93-8] | bptab | — | C$_{10}$H$_{25}$N$_2$OBr | 269.23 |
| 38a | | 38•HBr | | ~7.2 | C$_{10}$H$_{26}$N$_2$OBr$_2$ | 350.15 |
| 38b | 12 | 38 as the hydroxide salt (31% aqueous) | | — | C$_{10}$H$_{26}$N$_2$O$_2$ | 206.33 |
| 38c | 13 | 38 as the hemicarbonate salt (34% aqueous) | | — | C$_{21}$H$_{50}$N$_4$O$_5$ | 438.66 |
| 39 | 4 | 2-oxopiperazine [5625-67-2] | gmac | — | C$_{10}$H$_{22}$N$_3$O$_2$Cl | 251.76 |
| 39a | | 39 HCl | | ~4.4 | C$_{10}$H$_{23}$N$_3$O$_2$Cl$_2$ | 288.22 |
| 40 | 4 | N-Acetylpiperazine [13889-98-0] | gmac | — | C$_{12}$H$_{26}$N$_3$O$_2$Cl | 279.81 |
| 40a | | 40•HCl | | ~5.0 | C$_{12}$H$_{27}$N$_3$O$_2$Cl$_2$ | 316.27 |
| 41 | 4 | N,N'-Dimethylglycinamide [44565-47-1] | gmac | — | C$_{10}$H$_{24}$N$_3$O$_2$Cl | 253.77 |
| 41a | | 41•HCl | | ~5.6 | C$_{10}$H$_{25}$N$_3$O$_2$Cl$_2$ | 290.24 |
| 42 | 4 | N-Acetyl-N,N'-dimethylethylenediamine [27725-41-3] | gmac | — | C$_{12}$H$_{28}$N$_3$O$_2$Cl | 281.83 |
| 42a | | 42•HCl | | ~6.5 | C$_{12}$H$_{29}$N$_3$O$_2$Cl$_2$ | 318.29 |
| 43 | 4 | N,N'-Dimethyl-β-alanamide [50836-82-3] | gmac | — | C$_{11}$H$_{26}$N$_3$O$_2$Cl | 267.80 |
| 43a | | 43•HCl | | ~6.7 | C$_{11}$H$_{27}$N$_3$O$_2$Cl$_2$ | 304.26 |
| 44 | 4 | 4-Hydroxypiperidine [106-52-5] | gmac | — | C$_{11}$H$_{25}$N$_2$O$_2$Cl | 252.79 |
| 44a | | 44•HCl | | ~7.1 | C$_6$H$_{16}$N$_2$Cl$_2$ | 289.25 |
| 45 | 4 | N-Ethylmethylamine [627-78-2] | gmac | — | C$_9$H$_{23}$N$_2$OCl | 210.75 |
| 45a | | 45•HCl | | ~8.2 | C$_7$H$_{18}$N$_2$Cl$_2$ | 247.21 |
| 46 | 7b | N-Methyltaurine [107-86-6] | gmac | ~6.4 | C$_9$H$_{22}$N$_2$O$_4$S | 254.35 |
| 47 | 7b | N-Methyl-2-hydroxyhomotaurine [7013-34-5] | gmac | ~7.1 | C$_{10}$H$_{24}$N$_2$O$_5$S | 284.38 |
| 48 | 7b | N-Methylhomotaurine [163221-06-5] | gmac | ~7.3 | C$_{10}$H$_{24}$N$_2$O$_4$S | 268.38 |
| 49 | 7b | N-(2-Hydroxyethyl)taurine [29706-49-8] | gmac | ~5.5 | C$_{10}$H$_{24}$N$_2$O$_5$S | 284.38 |
| 50 | 7b | N-(2-Hydroxyethyl)-2-hydroxyhomotaurine [725202-09-05] | gmac | ~6.2 | C$_{11}$H$_{26}$N$_2$O$_6$S | 314.40 |
| 51 | 7b/7c | N-(2Hydroxyethyl)homotaurine [1119-23-9] | gmac | ~6.4 | C$_{11}$H$_{26}$N$_2$O$_5$S | 298.40 |
| 52 | 7b | N-(4-sulfobutyl)methylamine [89282-74-6] | gmac | ~8.0 | C$_{11}$H$_{26}$N$_2$O$_4$S | 282.40 |
| 53 | 7b/7c | N-(2-Hydroxyethyl)-N-(4-sulfobutyl)amine [54960-64-4] | gmac | ~7.1 | C$_{12}$H$_{28}$N$_2$O$_5$S | 312.43 |
| 54 | 6 | N,N,N',N'-Tetramethylethylenediamine [110-18-9] | ps | ~6.1 | C$_9$H$_{22}$N$_2$O$_3$S | 238.35 |
| 55 | 6 | N',N'-Diethyl-N,N-dimethylethylenediamine [123-10-4] | ps | ~6.7 | C$_{11}$H$_{26}$N$_2$O$_3$S | 266.41 |
| 56 | 6 | N,N'-Dimethyl-N,N'-bis(2-hydroxyethyl)-1,3-diaminopropane [10394-83-9] | ps | ~7.3 | C$_{12}$H$_{28}$N$_2$O$_5$S | 312.43 |
| 57 | 6 | N,N,N',N'-Tetramethyl-1,3-diaminopropane [110-95-2] | ps | ~8.1 | C$_{10}$H$_{24}$N$_2$O$_3$S | 252.38 |
| 58 | 6 | N',N'-Diethyl-N,N-dimethyl-1,3-diaminopropane [62478-82-4] | ps | ~8.7 | C$_{12}$H$_{28}$N$_2$O$_3$S | 280.43 |
| 59 | 8b/8c | N,N'-Dimethyl-N,N'-bis(2-sulfoethyl)-1,3-diaminopropane [185305-85-5] | brc | ~6.5, 8.0 | C$_{14}$H$_{33}$N$_3$O$_7$S$_2$ | 419.56 |
| 60 | 11b | 79a | HCl[b] | ~6.8, 8.2 | C$_{10}$H$_{25}$N$_2$O$_3$P | 252.30 |
| 61 | 11b | 80a | HCl[b] | ~6.0, 7.4 | C$_{10}$H$_{25}$N$_2$O$_3$P | 252.30 |
| 62 | 3 | 1-Methylpiperazine [109-01-3] | ps (2 eq) | ~3.7 | C$_{11}$H$_{24}$N$_2$O$_6$S$_2$ | 344.45 |
| 63 | 3 | 1-Methylhomopiperazine [4318-37-0] | ps (2 eq) | ~5.6 | C$_{12}$H$_{26}$N$_2$O$_6$S$_2$ | 358.48 |
| 64 | 3 | N,N-Dimethyl-N'-benzylethylenediamine [103-55-9] | ps (2 eq) | ~4.6 | C$_{17}$H$_{30}$N$_2$O$_6$S$_2$ | 422.57 |
| 65 | 3 | N,N-Dimethyl-N'-ethylethylenediamine [204-646-0] | ps (2 eq) | ~5.8 | C$_{12}$H$_{28}$N$_2$O$_6$S$_2$ | 360.49 |
| 66 | 3 | N,N,N'-Trimethylethylenediamine [142-25-6] | ps (2 eq) | ~5.5 | C$_{11}$H$_{26}$N$_2$O$_6$S$_2$ | 346.47 |
| 67 | 3 | N,N,N'-Trimethyl-1,3-diaminopropane [4543-96-8] | ps (2 eq) | ~7.5 | C$_{12}$H$_{28}$N$_2$O$_6$S$_2$ | 360.49 |
| 68 | 3 | N,N,N'-Trimethylethylenediamine [142-25-6] | bes (2 eq) | ~4.6 | C$_9$H$_{22}$N$_2$O$_6$S$_2$ | 318.41 |
| 69 | 3 | N,N,N'-Trimethyl-1,3-diaminopropane [4543-96-8] | bes (2 eq) | ~6.6 | C$_{10}$H$_{24}$N$_2$O$_6$S$_2$ | 322.44 |
| 70 | 3 | N,N,N'-Trimethylethylenediamine [142-25-6] | bs (2 eq) | ~6.2 | C$_{13}$H$_{30}$N$_2$O$_6$S$_2$ | 374.52 |
| 71 | 3 | N,N,N'-Trimethyl-1,3-diaminopropane [4543-96-8] | bs (2 eq) | ~8.2 | C$_{14}$H$_{32}$N$_2$O$_6$S$_2$ | 388.55 |
| 72 | 3 | N,N,N'-Trimethylethylenediamine [142-25-6] | bp (2 eq) | ~6.2 | C$_{11}$H$_{22}$N$_2$O$_4$ | 246.31 |
| 73 | 3 | N,N,N'-Trimethyl-1,3-diaminopropane [4543-96-8] | bp (2 eq) | ~8.2 | C$_{12}$H$_{24}$N$_2$O$_4$ | 260.34 |
| 74 | 5b | 4-(isopropylamino)piperidine [534595-53-4] | C$_2$H$_5$Br (3 eq) | — | C$_{14}$H$_{31}$N$_2$Br | 307.33 |
| 74a | | 74•HBr | | ~7.4 | C$_{14}$H$_{32}$N$_2$Br$_2$ | 388.24 |
| 75 | 2 | N-(2-Aminoethyl)trimethylammonium chloride [339-67-5] | tmcfc | ~11.9 | C$_{10}$H$_{26}$N$_4$Cl$_2$ | 267.21 |
| 76 | 1 | 1,1,3,3-Tetramethylguanidine [80-70-6] | bptab | ~12.9 | C$_{11}$H$_{28}$N$_4$Br$_2$ | 376.18 |
| 77 | 2 | N-(2-Aminoethyl)trimethylammonium chloride [339-67-5] | cdmic | ~11.1 | C$_{10}$H$_{24}$N$_4$Cl$_2$ | 267.21 |
| 78 | 4 | Ethanolamine [141-43-5] | gmac | — | C$_8$H$_{21}$N$_2$O$_2$Cl | 212.72 |
| 78a | | 78•HCl | | ~7.8 | C$_8$H$_{22}$N$_2$O$_2$Cl$_2$ | 249.18 |
| 79a | 11a | N,N,N',N'-Tetramethyl-1,3-diaminopropane [110-95-2] | debpp | ~8.1 | C$_{20}$H$_{35}$N$_2$O$_3$PBr$_2$ | 542.31 |
| 80a | 11a | N,N,N',N'-Tetraethylethylenediamine [150-77-6] | debbp | ~6.1 | C$_{20}$H$_{35}$N$_2$O$_3$PBr$_2$ | 542.31 |
| 81 | 8b | N,N'-dimethyl-N,N'-bis(2-sulfoethyl)trimethylenediame di-inner salt [185305-85-5] | brc | ~6.1 | C$_{21}$H$_{39}$N$_3$O$_7$S$_2$[c] | 509.69 |
| 82 | 8c | 81 | H$_2$/Pd | ~6.5, 8.0 | C$_{14}$H$_{33}$N$_3$O$_7$S$_2$[c] | 419.57 | aNo acid added during hydrogenation reaction (debenzylation)
bAcid hydrolysis of phosphonate ester
cMixture of diastereomers
gmac = N-(Glycidyl)trimethylammonium chloride [3033-77-0]
bptab = N-(3-Bromopropyl)trimethylammonium bromide [3779-42-8]
tmcfc = N,N,N',N'-tetramethylchloroformamidinium chloride [13829-06-6]
cdmic = 2-Chloro-1,3-dimethylimidazolinium chloride [37091-73-9]
fo + fa = formaldehyde [50-00-0] and formic acid [64-18-6]

TABLE 1-continued

Reactions and Compounds

| Cmpd | Method | Amine | Alkylating Agent | Est. pK$_a$ | Chemical Formula | Molecular Weight |
|---|---|---|---|---|---|---|

CH$_3$Cl = Methyl chloride [74-87-3]
CH$_3$Br = Methyl bromide [74-83-9]
C$_2$H$_5$Br = Ethyl bromide [74-96-4]
ps = 1,3-Propanesultone [1120-71-4]
bs = 1,4-Butanesultone [1633-83-6]
bes = 2-Bromoethanesulfonic acid, sodium salt [4263-52-9]
chps = 3-Chloro-2-hydroxypropanesulfonic acid, sodium salt [143218-48-8]
bp = 3-Bromopropanoic acid [590-92-1]
debpp = Diethyl 3-Bromopropanephosphonate [1186-10-3]
debbp = Diethyl 4-Bromobutanephosphonate [2004-10-25]
brc = N-(3-Chloro-2-hydroxypropyl)benzyldimethylammonium chloride ("benzyl reagens") [67304-25-0]
bpbdab = N-(3-Bromopropyl)benzyldimethylammonium bromide [113222-03-6]
HCl = Hydrochloric Acid [7647-01-0]

All of the compositions and processes disclosed and claimed herein can be made and executed by those of ordinary skill in the art without undue experimentation in light of the present disclosure and based upon the knowledge of such persons. While the compositions and processes of this invention have been described in terms of certain preferred embodiments, it will be apparent to those of ordinary skill in the art that variations may be applied to the compositions and/or processes and in the steps or in the sequence of steps of the processes described herein without departing from the concept, spirit and scope of the invention. More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method of buffering a chemical or biological composition, comprising adding to the composition an effective buffering amount of at least one protonated or un-protonated amine-quaternary ammonium compound having a general formula:

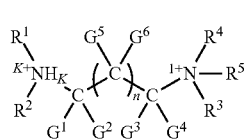

(Cl)$_d$ wherein:

n has integer values in the range 0-4, k is 0 for the un-protonated compound and k is 1 for the protonated compound;

each $G^1$, $G^3$ and $G^5$ is a chemical moiety independently selected from —H, —CH$_3$, —C$_2$H$_5$, or is a component of a cyclic chemical moiety, each $G^2$ and $G^4$ is a chemical moiety independently selected from —H, —CH$_3$, —CH$_2$OH, —C$_2$H$_5$, —CO$_2$H, —SO$_3$H, —PO$_3$H$_2$, —CO$_2^-$, —SO$_3^-$, —PO$_3$H$^-$, and —PO$_3^{2-}$, or is a component of the cyclic chemical moiety, each $G^6$ is a chemical moiety independently selected from —H, —CH$_3$, —CH$_2$OH, —C$_2$H$_5$, —OH, —OCH$_3$, —CO$_2$H, —SO$_3$H, —PO$_3$H$_2$, —CO$_2^-$, —SO$_3^-$, —PO$_3$H$^-$, and —PO$_3^{2-}$, or is a component of the cyclic chemical moiety and each $R^1$, $R^2$, $R^3$, $R^4$ and $R^5$ is a chemical moiety independently selected from —CH$_3$, —C$_2$H$_5$, —CH(CH$_3$)$_2$, -cyclohexyl, —C$_2$H$_4$OH, —C$_2$H$_4$OCH$_3$, —(CH$_2$)$_{2-3}$NHC(O)CH$_3$, —(CH$_2$)$_{2-3}$N(CH$_3$)C(O)CH$_3$, —(CH$_2$)$_{1-3}$C(O)NH$_2$, —(CH$_2$)$_{1-3}$C(O)NHCH$_3$, —(CH$_2$)$_{1-3}$C(O)N(CH$_3$)$_2$, —CH$_2$(CG$^5$G$^6$)$_m$SO$_3^-$, —CH$_2$(CG$^5$G$^6$)$_m$CO$_2^-$, —CH$_2$(CG$^5$G$^6$)$_m$CO$_2$H, —CH$_2$(CG$^5$G$^6$)$_m$PO$_3^{2-}$, —CH$_2$(CG$^5$G$^6$)$_m$PO$_3$H$^-$, —CH$_2$(CG$^5$G$^6$)$_m$PO$_3$H$_2$ with m being 0, 1, 2 or 3, or is a component of the cyclic chemical moiety, or $R^5$ is a chemical moiety —[CG$^7$G$^8$-(CG$^7$G$^9$)$_r$-CG$^7$G$^8$-H$_j$NR$^6$R$^7$]$^{j+}$, wherein each $G^7$ is a chemical moiety independently selected from —H, —CH$_3$, —C$_2$H$_5$, each $G^8$ is a chemical moiety independently selected from —H, —CH$_3$, —CH$_2$OH, —C$_2$H$_5$, —CO$_2$H, —SO$_3$H, —PO$_3$H$_2$, —CO$_2^-$, —SO$_3^-$, —PO$_3$H$^-$, and —PO$_3^{2-}$, $G^9$ is a chemical moiety independently selected from —H, —CH$_3$, —CH2, —OH, —C$_2$H$_5$, —OH, —OCH$_3$, —CO$_2$H, —SO$_3$H, —PO$_3$H$_2$, —CO$_2^-$, —SO$_3^-$, —PO$_3$H$^-$, and —PO$_3^{2-}$, r has integer values in the range 0-4, and j is 0 or 1, and each $R^6$ and $R^7$ is a chemical moiety independently selected from —CH$_3$, —C$_2$H$_5$, —CH(CH$_3$)$_2$, -cyclohexyl, —C$_2$H$_4$OH, —C$_2$H$_4$OCH$_3$, —(CH$_2$)$_{2-3}$NHC(O)CH$_3$, —(CH$_2$)$_{2-3}$N(CH$_3$)C(O)CH$_3$, —(CH$_2$)$_{1-3}$C(O)NH$_2$, —(CH$_2$)$_{1-3}$C(O)NHCH$_3$, —(CH$_2$)$_{1-3}$C(O)N(CH$_3$)$_2$, —CH$_2$(CG$^5$G$^6$)$_m$SO$_3^-$, —CH$_2$(CG$^5$G$^6$)$_m$CO$_2^-$, —CH$_2$(CG$^5$G$^6$)$_m$CO$_2$H, —CH$_2$(CG$^5$G$^6$)$_m$PO$_3^{2-}$, —CH$_2$(CG$^5$G$^6$)$_m$PO$_3$H$^-$, —CH$_2$(CG$^5$G$^6$)$_m$PO$_3$H$_2$, with m being 0, 1, 2 or 3;

wherein when the compound comprises the cyclic chemical moiety, the cyclic chemical moiety is one or more selected from (a), (b), (c), (d), (e), (f) and (g):

(a) one or more pair of $R^1$ and $R^2$, $R^3$ and $R^4$, $R^3$ and $R^5$, and/or $R^4$ and $R^5$, forms a single chemical moiety such that the pair is individually and independently —CH$_2$CH$_2$CH$_2$CH$_2$—, —CH$_2$CH(OH)CH(OH)CH$_2$—, —CH$_2$CH$_2$CH$_2$CH$_2$CH$_2$—, —CH$_2$CH$_2$OCH$_2$CH$_2$—, —CH$_2$CH$_2$CH(OH)CH$_2$CH$_2$—, —CH$_2$CH$_2$N(C(O)G$^1$)CH$_2$CH$_2$—, —CH$_2$C(O)N(G$^1$)CH$_2$CH$_2$—, —CH$_2$CH(OH)CH(OH)CH$_2$—, =C(NG$^1_2$)$_2$,

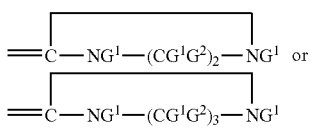

(b) one or more pair of $R^1$ and $R^3$, $R^1$ and $R^4$, $R^1$ and $R^5$, $R^2$ and $R^3$, $R^2$ and $R^4$ and/or $R^2$ and $R^5$ forms a single chemical moiety such that the pair is individually and independently —$(CG^1G^2)_g$- with n being 0 or 1 and g being 2 or 3;

(c) one or more pair of $G^1$ and $G^3$, $G^2$ and $G^4$, $G^1$ and $G^4$ and/or $G^2$ and $G^3$ forms a single chemical moiety such that the pair is individually and independently —$(CG^1G^6)_q$- with q having integer values 0-4 and the sum of q and n having integer values 3-4, and, when q=0, —$(CG^1G^6)_0$- is a single carbon-carbon bond between the carbon atoms to which the pair is attached in the general formula;

(d) one or more pair of $G^1$ and $G^2$, $G^3$ and $G^4$, and/or $G^5$ and $G^6$ forms a single chemical moiety such that the pair is individually and independently —$(CG^1G^6)_w$- with w having integer values 4-5;

(e) one or more pair of $R^1$ and $G^3$, $R^1$ and $G^4$, $R^2$ and $G^3$, $R^2$ and $G^4$, $R^3$ and $G^1$, $R^3$ and $G^2$, $R^4$ and $G^1$, $R^4$ and $G^2$, $R^5$ and $G^1$, and/or $R^5$ and $G^2$ forms a single chemical moiety such that the pair is individually and independently —$(CG^1G^2)_s$- with s having integer values 1-3, n having integer values 0-2 and the sum of s and n having integer values 2-3;

(f) one or more pair of $R^1$ and $G^5$, $R^1$ and $G^6$, $R^2$ and $G^5$, $R^2$ and $G^6$, $R^3$ and $G^5$, $R^3$ and $G^6$, $R^4$ and $G^5$, $R^4$ and $G^6$, $R^5$ and $G^5$, and/or $R^5$ and $G^6$ forms a single chemical moiety such that the pair is individually and independently —$(CG^1G^2)_v$- with v having integer values 0-3, n having integer values 1-4 and the sum of v and n having integer values 3-4 and, when v=0, —$(CG^1G^2)_0$- is a single carbon-carbon bond between the carbon atoms to which the pair is attached in the general formula; and (g) one or more pair of $R^1$ and $G^1$, $R^1$ and $G^2$, $R^2$ and $G^1$, $R^2$ and $G^2$, $R^3$ and $G^3$, $R^3$ and $G^4$, $R^4$ and $G^3$, $R^4$ and $G^4$, $R^5$ and $G^3$, and/or $R^5$ and $G^4$ forms a single chemical moiety such that the pair is individually and independently —$(CG^1G^2)_u$- with u having integer values 3-4;

wherein CI is a non-interfering counter-ion or mixture of non-interfering counter-ions as needed to maintain electroneutrality, with the charge on the amine-quaternary ammonium compound being equal to the value of quantity (j+k−z+1) wherein z equals the absolute value of the numerical sum of all negative charges on each —$CO_2^-$, —$SO_3^-$, —$PO_3H^-$, and —$PO_3^{2-}$ moiety contained within the $R^1$, $R^2$, $R^3$, $R^4$, $R^5$, $R^6$, $R^7$, $G^2$, $G^4$, $G^6$ $G^8$ and/or $G^9$ present, and wherein d equals |j+k−z+1| for monovalent counter-ions, |j+k−z+1|/2 for divalent counter-ions, |j+k−z+1|/3 for trivalent counter-ions, |j+k−z+1|/4 for tetravalent counter-ions and the sign of (z−j−k+1) reflects the charge on the counter-ion(s), except that when (j+z−k+1) is zero, d is zero and no separate counter-ion is present.

2. A method as defined in claim 1 wherein CI is a non-interfering anion or a mixture of non-interfering anions selected from Cl$^-$, Br$^-$, I$^-$, OH$^-$, F$^-$, OCH$_3^-$, HCO$_2^-$, CH$_3$CO$_2^-$, CF$_3$CO$_2^-$, NO$_3^-$, ClO$_4^-$, BF$_4^-$, PF$_6^-$, HSO$_4^-$, HCO$_3^-$, H$_2$PO$_4^-$, CH$_3$OCO$_2^-$, CH$_3$OSO$_3^-$, CH$_3$SO$_3^-$, CF$_3$SO$_3^-$, H$_2$PO$_3^-$, CH$_3$PO$_3$H$^-$, HPO$_3^{2-}$, CH$_3$PO$_3^{2-}$, CO$_3^{2-}$, SO$_4^{2-}$, HPO$_4^{2-}$ and PO$_4^{3-}$.

3. A method as defined in claim 1 wherein CI is a non-interfering cation or a mixture of non-interfering cations selected from: Li$^+$, Na$^+$, K$^+$, Rb$^+$, Cs$^+$, NH$_4^+$, Ag$^+$, Ti$^+$, Mg$^{2+}$, Ca$^{2+}$, Sr$^{2+}$, Ba$^{2+}$, VO$^{2+}$, Mn$^{2+}$, Fe$^{2+}$, Co$^{2+}$, Ni$^{2+}$, Cu$^{2+}$, Zn$^{2+}$ Cd$^{2+}$, Hg$^{2+}$, Eu$^{2+}$, UO$_2^{2+}$, Pb$^{2+}$, Al$^{3+}$, Ga$^{3+}$, Y$^{3+}$, BiO$^{3+}$, La$^{3+}$, Ce$^{3+}$, Pr$^{3+}$, Nd$^{3+}$, Sm$^{3+}$, Eu$^{3+}$, Gd$^{3+}$, Tb$^{3+}$, Dy$^{3+}$, Ho$^{3+}$, Er$^{3+}$, Tm$^{3+}$, Yb$^{3+}$, Lu$^{3+}$ and Th$^{4+}$.

4. A method as defined in claim 1 wherein CI is a non-interfering cation or a mixture of non-interfering cations selected from: a protonated primary alkyl or hydroxyalkyl amine, a protonated secondary alkyl or hydroxyalkyl amine, a protonated tertiary alkyl or hydroxyalkyl amine, a diprotonated alkyl, alkylene, hydroxyalkyl or hydroxyalkylene diamine, a quaternary alkyl or hydroxyalkyl ammonium compound, an alkyl or hydroxyalkyl sulfonium compound, an alkyl or hydroxyalkyl sulfoxonium compound, a quaternary alkyl or hydroxyalkyl phosphonium compound and a di-quaternary alkyl, alkylene, hydroxyalkyl or hydroxyalkylene ammonium compound, wherein the foregoing alkyl, alkylene, hydroxyalkyl and hydroxyalkylene groups contain one to three carbon atoms, and wherein the cation or the mixture of cations is not a compound as defined in claim 1.

5. A method as defined in claim 1 wherein CI is a non-interfering buffering anion, a mixture of non-interfering buffering anions, a non-interfering buffering cation or a mixture of non-interfering buffering cations, with pKa value(s) in the range 2-12, and wherein CI is not an amine-quaternary ammonium compound as defined in claim 1.

6. A method as defined in claim 1 wherein CI is a non-interfering buffering anion, a mixture of non-interfering buffering anions, a non-interfering buffering cation or a mixture of non-interfering buffering cations, with pKa value(s) in the range 1-13, and wherein CI is an amine-quaternary ammonium compound as defined in claim 1, and has a charge conferring electroneutrality on the compound.

7. A method as defined in claim 1 wherein the compound comprises the cyclic moiety as defined in (a), wherein the cyclic moiety has one of the following structures:

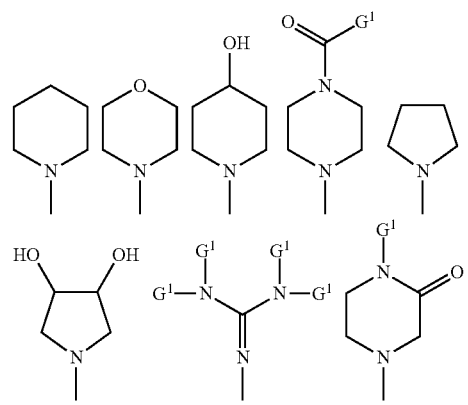

wherein $G^1$ and other components of the compound are as defined as in claim 1.

8. A method as defined in claim 1 wherein the compound comprises the cyclic moiety as defined in (a), wherein the cyclic moiety has one of the following structures:

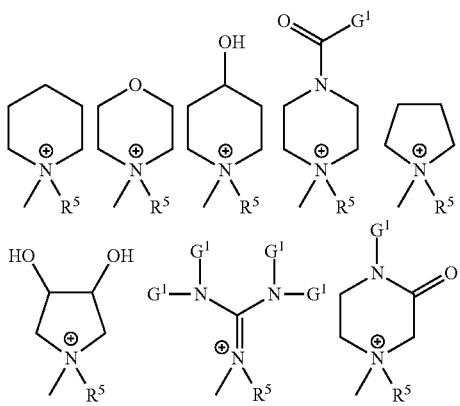

wherein $G^1$ and other components of the compound are as defined as in claim 1.

9. A method as defined in claim 1 wherein the compound comprises the cyclic moiety as defined in (b), wherein the compound has one of the following structures:

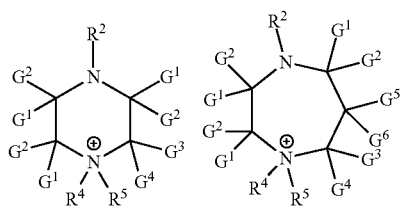

wherein each of $G^1$, $G^1$, $G^2$, $G^3$, $G^4$, $G^5$, $R^2$, $R^4$ and $R^5$ is independently defined as in claim 1.

10. A method as defined in claim 1 wherein the compound comprises the cyclic moiety as defined in (c), wherein the compound has one of the following structures:

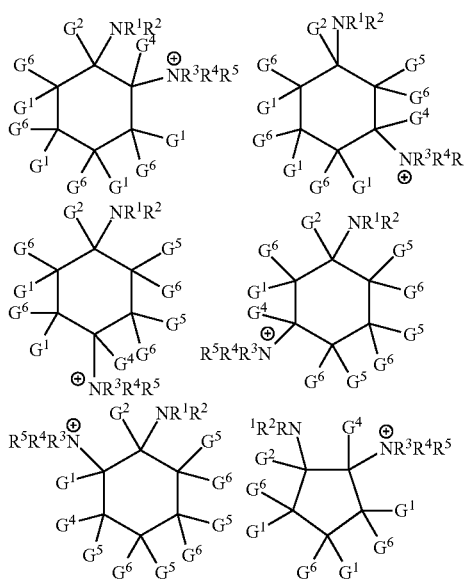

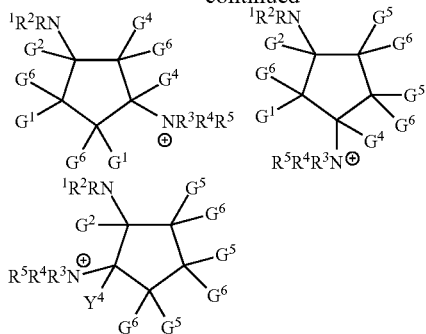

wherein each of $G^1$, $G^1$, $G^2$, $G^3$, $G^4$, $G^5$, $G^6$, $R^1$, $R^2$, $R^3$, $R^4$ and $R^5$ is independently defined as in claim 1.

11. A method as defined in claim 1 wherein the compound comprises the cyclic moiety as defined in (e) wherein the compound has one of the following structures:

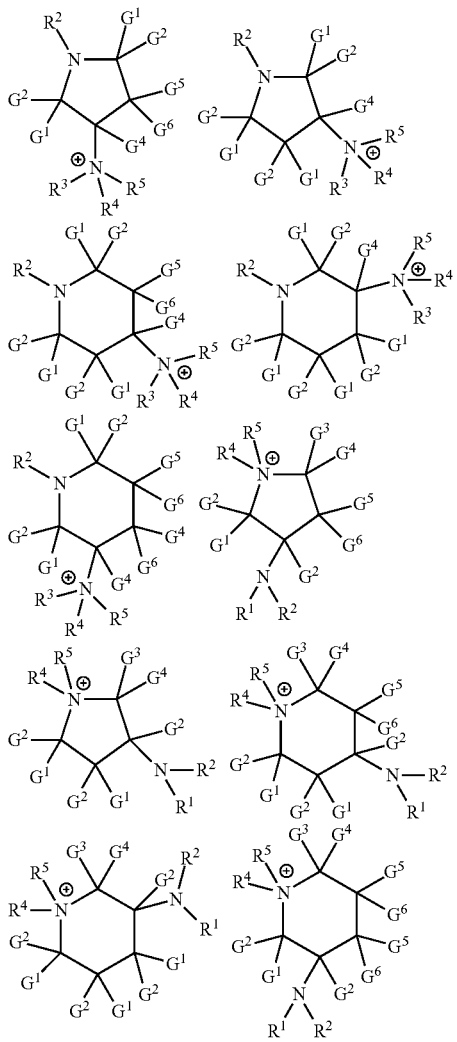

wherein each of $G^1$, $G^1$, $G^2$, $G^3$, $G^4$, $G^5$, $G^6$, $R^1$, $R^2$, $R^3$, $R^4$ and $R^5$ is independently defined as in claim 1.

* * * * *